United States Patent
Skowerski et al.

(10) Patent No.: US 11,976,085 B2
(45) Date of Patent: May 7, 2024

(54) PROCESS FOR PRODUCING RUTHENIUM COMPLEXES AND INTERMEDIATES THEREOF AND THEIR USE IN OLEFIN METATHESIS

(71) Applicant: APEIRON SYNTHESIS S.A., Wroclaw (PL)

(72) Inventors: Krzysztof Skowerski, Jablonowo Pomorskie (PL); Rafal Gawin, Warsaw (PL)

(73) Assignee: Aperion Synthesis S.A., Wroclaw (PL)

( * ) Notice: Subject to any disclaimer, the term of this patent is extended or adjusted under 35 U.S.C. 154(b) by 0 days.

(21) Appl. No.: 17/513,752

(22) Filed: Oct. 28, 2021

(65) Prior Publication Data
US 2022/0073549 A1   Mar. 10, 2022

Related U.S. Application Data

(63) Continuation of application No. 15/764,123, filed as application No. PCT/IB2016/054486 on Jul. 27, 2016, now Pat. No. 11,192,911.

(30) Foreign Application Priority Data

Sep. 30, 2015 (PL) .......................... 414234

(51) Int. Cl.
   *C07F 15/00* (2006.01)
   *B01J 31/22* (2006.01)
   *C07C 6/02* (2006.01)

(52) U.S. Cl.
   CPC ....... *C07F 15/0046* (2013.01); *B01J 31/2208* (2013.01); *B01J 31/2273* (2013.01); *B01J 31/2278* (2013.01); *B01J 31/2295* (2013.01); *C07C 6/02* (2013.01); *B01J 2231/54* (2013.01); *B01J 2231/543* (2013.01); *B01J 2531/821* (2013.01); *B01J 2540/44* (2013.01); *C07C 2531/22* (2013.01)

(58) Field of Classification Search
   None
   See application file for complete search history.

(56) References Cited

U.S. PATENT DOCUMENTS

| | | |
|---|---|---|
| 6,613,910 B2 | 9/2003 | Grubbs et al. |
| 6,818,586 B2 | 11/2004 | Grubbs et al. |
| 6,867,303 B2 | 3/2005 | Grela |
| 7,632,772 B2 | 12/2009 | Zhan |
| 8,067,610 B2 | 11/2011 | Schrodi |

(Continued)

FOREIGN PATENT DOCUMENTS

| | | |
|---|---|---|
| FR | 2947189 | 7/2011 |
| WO | 2011056881 | 5/2011 |
| WO | 2015157736 | 10/2015 |

OTHER PUBLICATIONS

V.M. Marx et al., Angew. Chem. Int. Ed. 2015, 54, 1919-1923, published online Dec. 2014.

(Continued)

*Primary Examiner* — Yun Qian
(74) *Attorney, Agent, or Firm* — Reed Smith LLP; Richard J. Brown

(57) ABSTRACT

The invention provides a new process for producing ruthenium complexes represented by the Formula 1. Invention provides also the use of ruthenium complexes represented by the Formula 1 as precatalysts and/or catalysts in olefin metathesis reactions.

11 Claims, 4 Drawing Sheets

(56) References Cited

U.S. PATENT DOCUMENTS

| | | |
|---|---|---|
| 8,501,973 B2 | 8/2013 | Schrodi |
| 9,249,170 B2 | 2/2016 | Marx et al. |
| 9,328,132 B2 | 5/2016 | Skowerski et al. |
| 9,499,643 B2 | 11/2016 | Maliverney |
| 9,776,178 B2 | 10/2017 | Mauduit |
| 2003/0069374 A1 | 4/2003 | Grubbs et al. |
| 2010/0022789 A1 | 1/2010 | Mignani |

OTHER PUBLICATIONS

M. Evans, N-heterocyclic Carbenes, The Organometallic Reader, Jan. 26, 2012.
W. Zhang et al., J. Organomet. Chem. 2007, 692, 3563-3567.
Notice of Opposition to EP Application 16774982.9 (EP3356379), dated Dec. 8, 2021.
Plaintiff filing for Opposition to EP Application 16774982.9 (EP3356379), dated Dec. 8, 2021.
Communication of information for Opposition to EP Application 16774982.9 (EP3356379), dated Dec. 14, 2021.
Consolidated List of References for Opposition to EP Application 16774982.9 (EP3356379).
International Search Report and Written Opinion of the International Searching Authority, dated Dec. 7, 2016 in corresponding International Patent Application No. PCT/IB2016/054486.
Nolan et al. Organometallics, 29, 3007-3011 (Year: 2010).
Anderson et al. Organometallics, 27, 563-566 (Year: 2008).

Standard curve for substrate (9-DAME):

Standard curve for product (DIESTER-C18):

Standard curve for substrate (1-DECENE):

Standard curve for product (OD-9-ENE):

PROCESS FOR PRODUCING RUTHENIUM COMPLEXES AND INTERMEDIATES THEREOF AND THEIR USE IN OLEFIN METATHESIS

This application is a continuation of U.S. patent application Ser. No. 15/764,123 filed Mar. 28, 2018, which is a National Stage Entry of PCT/I82016/054486 filed Jul. 27, 2016 and claims the benefit of Polish patent application no. PL414234 filed Sep. 30, 2015, under 35 U.S.C. § 119, the entire disclosure of each are incorporated herein by reference.

The invention provides a new process for producing ruthenium complexes and their use in olefin metathesis as precatalysts and/or catalysts. This invention finds its application in the broadly defined organic synthesis using olefin cross-metathesis (CM), ring-closing metathesis (RCM), ring closing enyne metathesis (RCEYM) reactions, in a diastereoselective ring-rearrangement metathesis (DRRM) reaction, in polymerization of olefins in ring-opening metathesis polymerization (ROMP) reactions and an acyclic diene metathesis (ADMET).

Over the last few years a great progress has been made in olefin metathesis applications in organic synthesis [R. H. Grubbs (ed.), A. G. Wenzel (ed.), D. J. O'Leary (ed.), E. Khosravi (ed.), *Handbook of Olefin Metathesis*, 2nd. ed., 3 volumes 2015, John Wiley & Sons, Inc., 1608 pages].

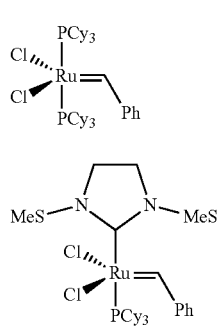

Gru-I

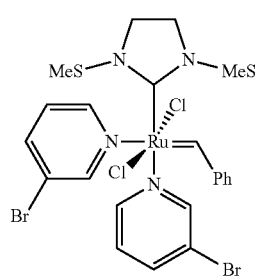

Gru-II

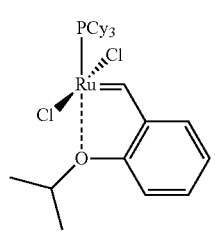

Gru-III

Hov-I

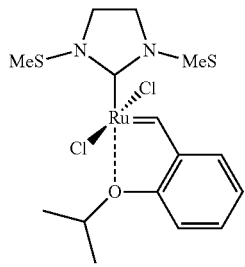

Hov-II

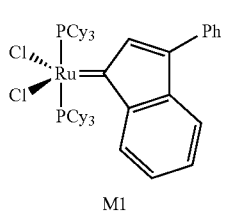

M1 (Ind-I)

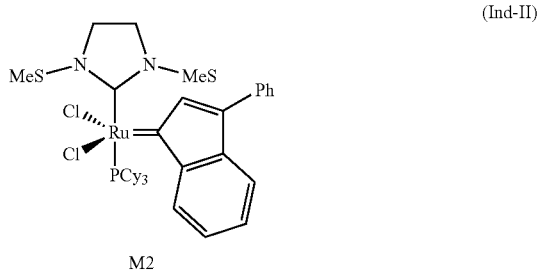

M2 (Ind-II)

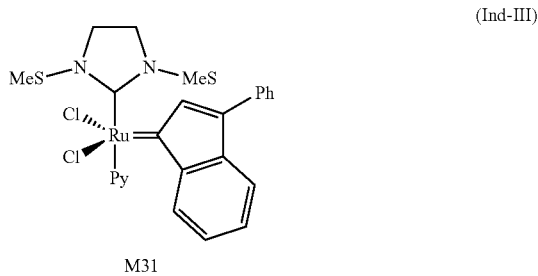

M31 (Ind-III)

Mes = 2,4,6-trimethylphenyl   Cy = cyclohexyl   Py = pyridine

In the prior art there are known dozens of commercially available ruthenium carbene complexes acting as precatalysts and/or catalysts, characterised by both high activity in various types of metathesis reactions, and a broad tolerance of functional groups. The above combination of properties determines the suitability of this type of precatalysts and/or catalysts in the organic synthesis. The most prevalent in the literature ruthenium complexes in olefin metathesis reactions are 1st, 2nd and 3rd generation Grubbs-type ruthenium complexes (Gru-I, Gru-II and Gru-III), Hoveyda-type complexes (Hov-I and Hov-II) and indenylidene complexes (Ind-I, Ind-II and Ind-III), [Grubbs et al. *Chem. Rev.* 2010, 110, 1746-1787; Nolan et al. *Chem. Commun.* 2014, 50, 10355-10375]. In other cases, the majority of olefin metathesis catalyst structures are derived from the above-mentioned ruthenium complexes.

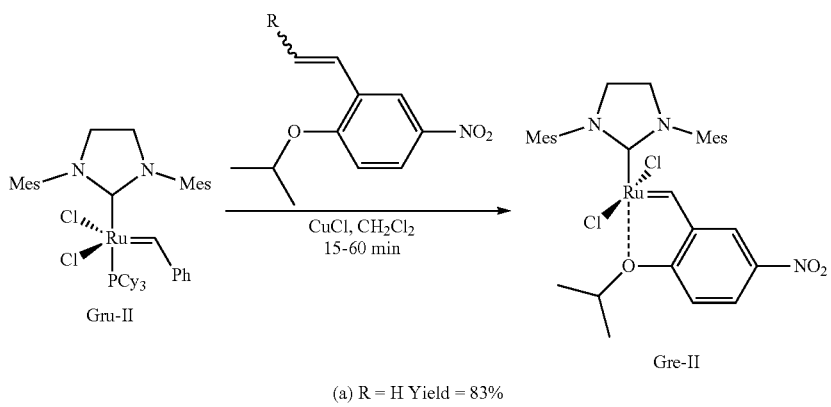

(a) R = H Yield = 83%

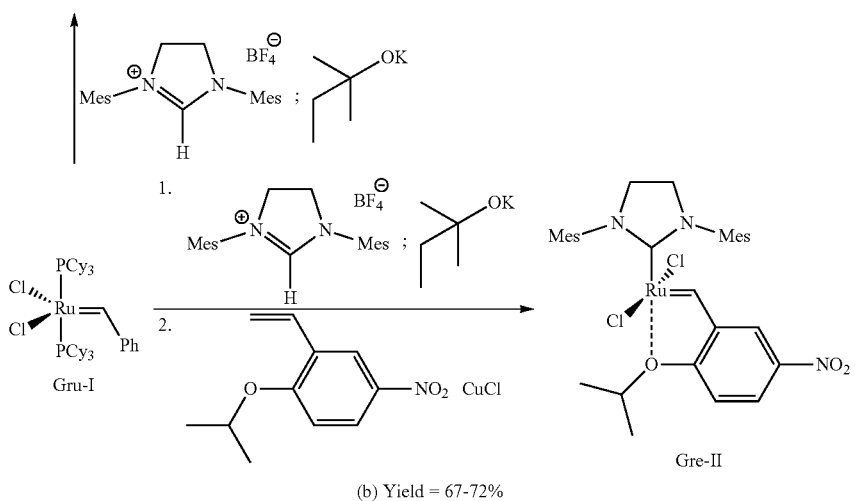

(b) Yield = 67-72%

In the prior art there are known few methods of second generation Hoveyda-type precatalyst preparation [K. Grela, et al., *Organometallics*, 2007, 26, 1096-1099]. They involve contacting second generation Grubbs-type complexes (Gru-II) with 1-isopropoxy-5-nitrostyrene, or 1-isopropoxy-4-nitro-2-propenylbenzene in the presence of a copper(I) salt, Path (a). Another method of second generation Hoveyda-type complex preparation is a three-step one-pot procedure, Path (b). It involves in situ N-heterocyclic carbene (NHC) ligand generation, and contacting it with Gru-I complex and then addition of 1-isopropoxy-5-nitrostyrene in the presence of copper(I) chloride. Unfortunately, the use of styrene derivatives in large-scale synthesis is undesirable. Such compounds are obtained using cumbersome Wittig reaction or Stille coupling reaction. Much more desirable on an industrial scale is the use of propenyl derivatives such as 1-isopropoxy-4-nitro-2-propenylbenzene. Propenyl derivatives are obtained in a sequence of reactions: alkylation of a suitable phenol derivative with an ally halide, Claisen rearrangement [3,3], and C=C bond isomerisation.

Alternative synthesis routes of the second generation Hoveyda-type complexes (Hov-II) involve contacting the first generation Hoveyda-type complexes (Hov-I) with NHCs, generated in situ, or provided to the reaction medium in another way, Paths (c), (d), and (e). These methods are complementary to the previously presented but they are not free of important industrial flaws.

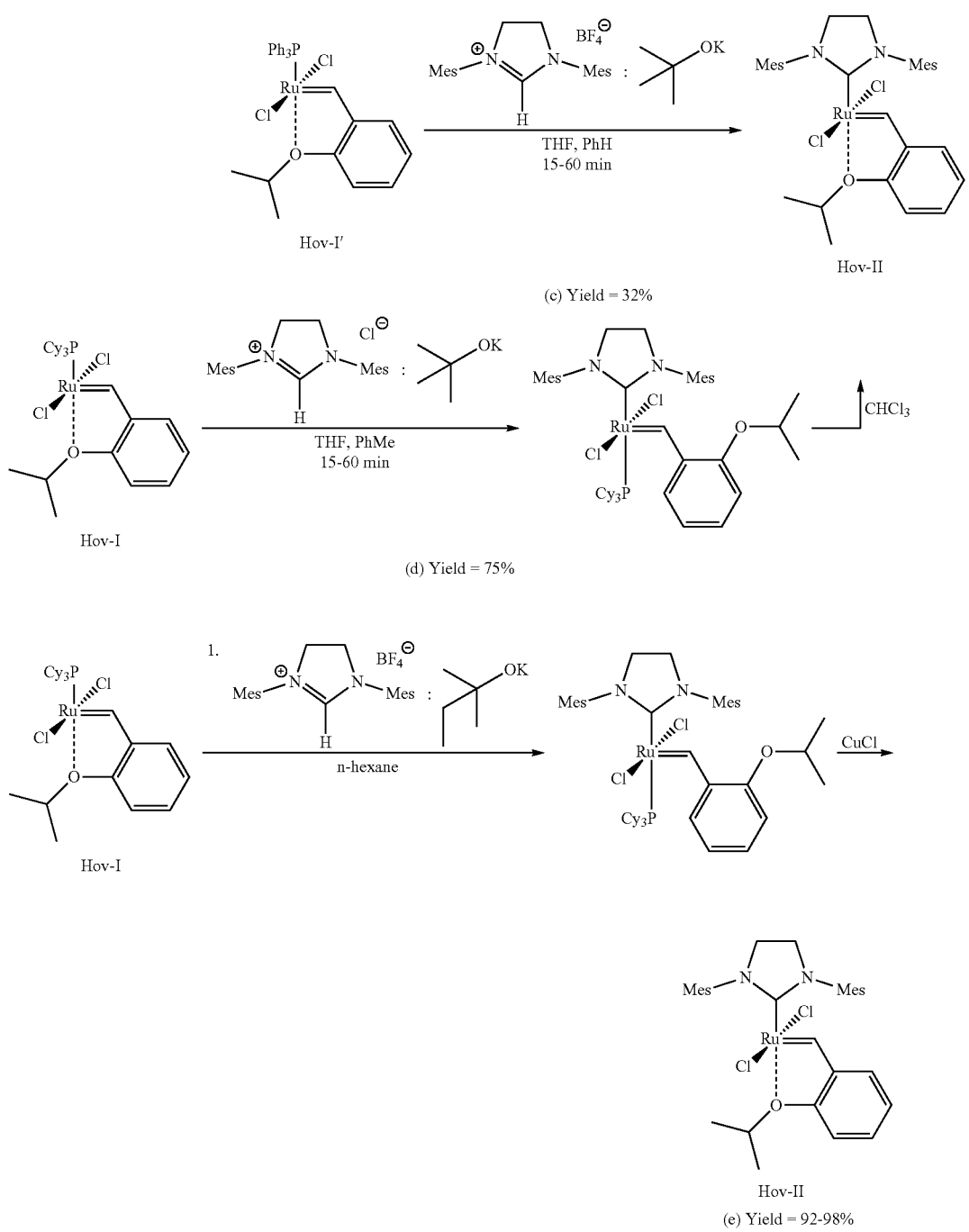

The most important of them is the first generation Hoveyda-type catalyst synthesis (Hov-I) which requires the use of a diazo compound [A H, Hoveyda et al., *J. Am. Chem. Soc.* 1999, 121, 791-799]. Alternatively, Hov-I may be obtained in a reaction of the first generation catalyst containing two phosphine ligands (e.g. Gru-I or Ind-I) with 2-isopropoxystyrene, which synthesis, as mentioned above, is cumbersome, What is important, the first generation catalysts containing two phosphine ligands do not react neither with the easily obtained 2-isopropoxypropenylbenzene not with its substituted in the aromatic ring derivatives.

In practical terms, the use of olefin metathesis reaction particularly on an industrial scale the most important parameters are the turn over number (TON) and the reaction selectivity. One type of olefin metathesis reaction of a huge industrial potential is a cross metathesis with ethylene (Le. ethenolysis), particularly the ethenolysis of unsaturated fatty acid derivatives, The first generation catalysts show relatively good selectivity in the ethenolysis reaction but unsatisfactory efficiency (low TON). On the other hand, the second generation catalysts containing NHC ligands show good efficiency (high TON) but low selectivity, The best ethenolysis reaction results are obtained with complexes containing both CAAC (Cyclic Alkyl Amino Carbene) ligands and Hove yda-type benzylidene ligand (Hov-CAAC).

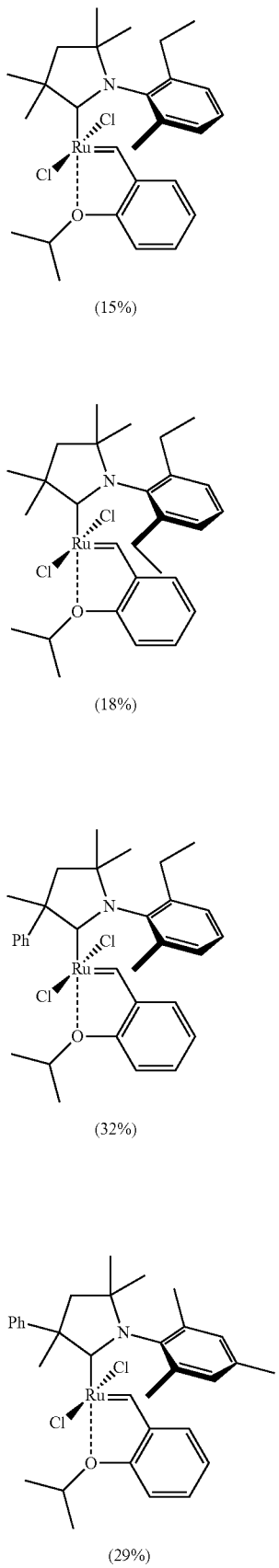

Hov-CAAC-1 (15%)

Hov-CAAC-2 (18%)

Hov-CAAC-3 (32%)

Hov-CAAC-4 (29%)

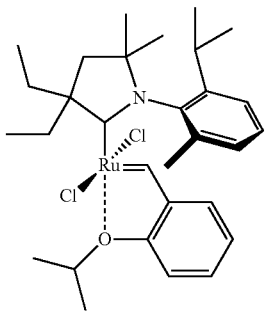

Hov-CAAC-5 (44%)

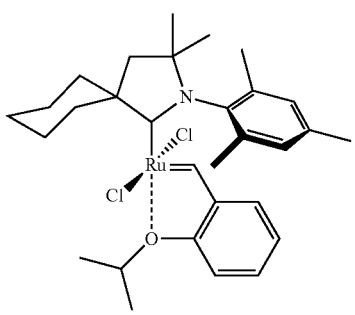

Hov-CAAC-6 (39%)

Known in the prior art Hov-CAAC complex synthesis method involves contacting CAAC ligand (in its pure form or generated in situ) with Hov-I complex, synthesis similar to Paths (c), (d), and (e), This method is unfavourable not only because of cumbersome Hov-I complex synthesis [A H. Hoveyda et al., *J. Am. Chem. Soc.* 1999, 121, 791-799], but also due to its low yields and the use of a glovebox [US2014309433A1; G. Bertrand, and R. H. Grubbs et al., *Angew. Chem. Int. Ed.,* 2015, 54, 1919-1923]. The disadvantage of this synthetic approach is a difficult benzylidene ligand modification, which may affect the activity and efficiency of the target ruthenium complex. Obtaining the second generation Hoveyda-type complexes containing CAAC ligand and modified benzylidene ligand according to a method known in the prior art would require each time a synthesis of a properly modified 2-isopropoxystyrene and then respective first generation Hoveyda-type complex.

In the prior art, there is also known a problem with preparation of precatalysts containing both CAAC-type ligand and modified benzylidene ligand. French patent [FR2947189B1] provides a cumbersome method of the non-activated benzylidene ($=CH-C_6H_4-OCH(CH_3)_2$) ligand replacement in the Hov-CAAC-type precatalyst, which for this reason was contacted with 5 molar equivalents of 1-isopropoxy-5-diethylamino-2-propenylbenzene in the presence of ethylene gas, which served as a reaction activator.

Known is also in the prior art a CAAC carbene reaction with Grubbs-type complex containing both tricyclohexylphosphine and two pyridine ligands Gru-I-Py$_2$, Path (f). Such reaction leads to a phosphine ligand substitution with CAAC carbene and formation of a respective third generation Gru-III-CAAC complex which had unexpectedly low activities in the standard RCM reaction of diene ring closing [G. Bertrand and R. H. Grubbs et al., *Angew. Chem.,* 2007, 119, 7400-7403].

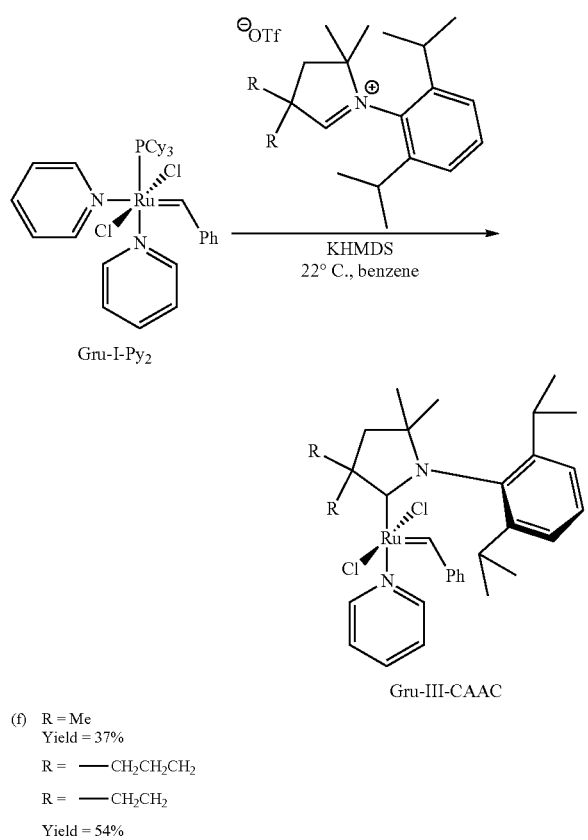

Gru-I-Py$_2$

Gru-III-CAAC (f) R = Me
Yield = 37%

R = —CH$_2$CH$_2$CH$_2$

R = —CH$_2$CH$_2$
Yield = 54%

Above-described most preferable synthesis method of the second generation Hoveyda-type complexes containing NHC ligands in which ruthenium precursor is the first generation complex containing two phosphine ligands never was employed in the Hov-CAAC-type complex synthesis.

Synthesis of the Hov-CAAC-type complexes from the first generation complexes containing two phosphine ligands would be advantageous particularly from the large-scale production aspect. Moreover, it would be particularly advantageous if this three-step synthesis could be performed in a single reaction vessel (one-pot synthesis).

During laboratory studies on the ruthenium complexes it has been surprisingly found that CAAC-type ligands react with the first generation complexes containing two phosphine ligands causing replacement of the both phosphines leading to a complex containing two CAAC ligands. With 1.25 to 2 molar equivalents of the CAAC ligand by TLC analysis one can observe formation of only small amounts of complex containing both one CAAC ligand and one phosphine ligand. It has been surprisingly found that in the presence of a compound which can form complexes with carbenes (e.g. CuCl or other phosphine and/or NHC ligand scavenger) complexes containing two CAAC ligands react with respective propenylbenzene derivatives providing Hov-CAAC-type complexes. Moreover, it has been noted that this reaction can be conducted without isolating the complex containing two CAAC ligands, that is Hov-CAAC-type complex may be easily obtained by multi-step one-pot type procedure, starting from the first generation complex containing two phosphine ligands. The method according to the invention allows avoiding cumbersome Hov-I complex synthesis and allows a simple modification of the benzylidene ligand. Catalytic properties of the complexes obtained could be modulated by choosing the right CAAC ligand, benzylidene ligand or anionic ligands. During studies it has also been noted, that the activity and efficiency of the complexes containing two CAAC ligands depend strongly on structure of the CAAC ligand. Relatively fast-initiating complexes containing two CAAC ligands showed to be perfect catalysts for olefin metathesis.

The present application provides a general and economically advantageous method of Hov-CAAC-type complex synthesis in which ruthenium precursor is any first generation complex containing two phosphine ligands e.g. Gru-I, Ind-I, or Umicore M10™. The invention provides also complexes containing two CAAC ligands, which may serve as precursors in the Hov-CAAC complex synthesis, and also as olefin metathesis catalysts.

The invention will be described in more detail in the preferred embodiment and in embodiments of the invention with reference to the accompanying drawing, in which:

FIG. 1 summarizes commercially available olefin metathesis precatalysts and catalysts, and novel pre catalysts and catalysts of the present invention.

Therefore, the present invention provides a process for producing compound represented by the Formula 1,

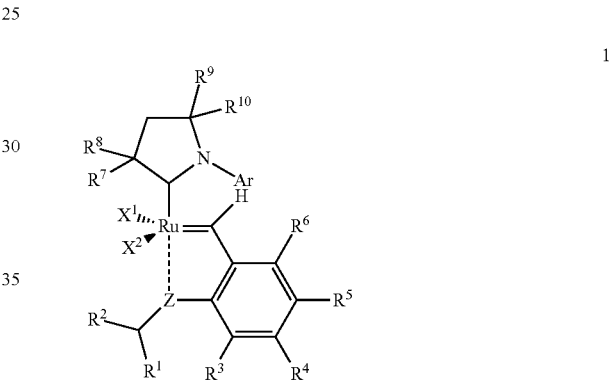

1 wherein:

$X^1$ and $X^2$ are each independently an anionic ligand selected from halogen atoms, —CN, —SCN, —OR', —SR', —O(C=O)R', —O(SO$_2$)R', and —OSi(R')$_3$ group, wherein R' is C$_1$-C$_{12}$ alkyl, C$_3$-C$_{12}$ cycloalkyl, C$_2$-C$_{12}$ alkenyl, C$_5$-C$_{20}$ aryl, which are optionally substituted with at least one C$_1$-C$_{12}$ alkyl, C$_1$-C$_{12}$ perfluoroalkyl, C$_1$-C$_{12}$ alkoxy, C$_5$-C$_{24}$ aryloxy, C$_5$-C$_{20}$ heteroaryloxy, or a halogen atom;

Z is an atom selected from a group of O, S, NR', wherein R' is C$_1$-C$_{12}$ alkyl, C$_3$-C$_{12}$ cycloalkyl, C$_2$-C$_{12}$ alkenyl, C$_5$-C$_{20}$ aryl, which are optionally substituted with at least one C$_1$-C$_{12}$ alkyl, C$_1$-C$_{12}$ perfluoroalkyl, C$_1$-C$_{12}$ alkoxy, C$_5$-C$_{24}$ aryloxy, C$_5$-C$_{20}$ heteroaryloxy, or a halogen atom;

Ar is an aryl group substituted with hydrogen atoms or optionally substituted with at least one C$_1$-C$_{12}$ alkyl, C$_1$-C$_{12}$ perfluoroalkyl, C$_1$-C$_{12}$ alkoxy, C$_5$-C$_{24}$ aryloxy, and C$_5$-C$_{20}$ heteroaryloxy group, or a halogen atom;

$R^1$ and $R^2$ are each independently hydrogen atom, C$_1$-C$_{25}$ alkyl group, C$_1$-C$_{25}$ alkoxy group, C$_2$-C$_{25}$ alkenyl group, C$_1$-C$_{12}$ perfluoroalkyl, C$_5$-C$_{20}$ aryl, C$_5$-C$_{24}$ aryloxy, C$_5$-C$_{20}$ heteroaryloxy, or can be combined together to form substituted or unsubstituted C$_4$-C$_{10}$ cyclic or C$_4$-C$_{12}$ polycyclic system, can be also an ester (—COOR'), amide (—CONR'$_2$), formyl (—CHO), ketone (—COR'), and hydroxamic (—CON(OR)(R) group or a halogen atom, in which R' is C$_1$-C$_{12}$ alkyl, C$_3$-C$_{12}$ cycloalkyl, C$_2$-C$_{12}$ alkenyl, C$_5$-C$_{20}$ aryl, which are optionally substituted with at least one $C_1$-$C_{12}$ alkyl, $C_1$-$C_{12}$ perfluoroalkyl, $C_1$-$C_{12}$ alkoxy, $C_5$-$C_{24}$ aryloxy, $C_5$-$C_{20}$ heteroaryloxy, or a halogen atom;

$R^3$, $R^4$, $R^5$, $R^6$ are each independently hydrogen atom, $C_1$-$C_{25}$ alkyl group, $C_1$-$C_{25}$ alkoxy group, or $C_1$-$C_{25}$ alkenyl group, wherein $R^3$, $R^4$, $R^5$, $R^6$ substituents can be combined together to form substituted or unsubstituted $C_4$-$C_{10}$ cyclic or $C_4$-$C_{12}$ polycyclic system, can also independently be an alkoxy (—OR), sulphide (—SR), sulfoxide (—S(O)R'), sulphonium (—S+R'$_2$), sulphone (—SO$_2$R), sulphonamide (—SO$_2$NR'$_2$), amine (—NR'$_2$), ammonium (—N+R'$_3$), nitre (—NO$_2$), cyano (—CN), phosphonate (—P(O)(OR')$_2$), phosphinate (—P(O)R'(OR')), phosphoninum (—P(OR)$_2$), phosphine (—PR'$_2$), phosphine oxide (—P(O)R'$_2$), phosphonium (-p+R'$_3$), carboxy (—COOH), ester (—COOR'), amide (—CONR'$_2$, or —NR'C(O)R'), formyl (—CHO), and ketone (—COR') group, wherein R' is $C_1$-$C_5$ alkyl, $C_1$-$C_5$ perfluoroalkyl, $C_5$-$C_{24}$ aryl, $C_7$-$C_{24}$ aralkyl, $C_5$-$C_{24}$ perfluoroaryl;

$R^7$, $R^8$, $R^9$, and $R^{10}$ are each independently hydrogen atom, or $C_1$-$C_{25}$ alkyl group, $R^7$ and/or $R^8$ can be combined with $R^9$ and/or $R^{10}$ to form cyclic system, are also independently $C_1$-$C_{12}$ alkyl group, $C_3$-$C_{12}$ cycloalkyl, $C_2$-$C_{12}$ alkenyl, $C_5$-$C_{20}$ aryl, $C_1$-$C_5$ perfluoroalkyl, $C_7$-$C_{24}$ aralkyl, $C_5$-$C_{24}$ perfluoroaryl, which are optionally substituted with at least one $C_1$-$C_{12}$ alkyl, $C_1$-$C_{12}$ perfluoroalkyl, $C_1$-$C_{12}$ alkoxy, $C_5$-$C_{24}$ aryloxy, $C_5$-$C_{20}$ heteroaryloxy, or a halogen atom;

characterised in that the alkylidene ruthenium complex represented by the Formula 2

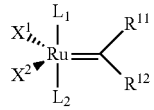

2 wherein:

$L^1$, $L^2$ are each a neutral ligand selected from a group including phosphine, in particular P(R')$_3$, wherein each R' is independently $C_1$-$C_{12}$ alkyl, $C_3$-$C_{12}$ cycloalkyl, $C_5$-$C_{20}$ aryl, $C_7$-$C_{24}$ aralkyl, $C_5$-$C_{24}$ perfluoroaryl, 5-12-membered heteroaryl; two R' can be combined together to form cycloalkyl ring containing phosphorus atom in the ring.

$X^1$, $X^2$ are each an anionic ligand selected independently from a group including halide anions, —CN, —SCN, —OR', —SR', —O(C═O)R', —O(SO$_2$)R', and —OSi(R')$_3$ group, wherein R' is $C_1$-$C_{12}$ alkyl, $C_3$-$C_{12}$ cycloalkyl, $C_2$-$C_{12}$ alkenyl, or $C_5$-$C_{20}$ aryl, which is optionally substituted with at least one $C_1$-$C_{12}$ alkyl, $C_1$-$C_{12}$ perfluoroalkyl, $C_1$-$C_{12}$ alkoxy, $C_5$-$C_{24}$ aryloxy, $C_5$-$C_{20}$ heteroaryloxy, or a halogen atom;

$R^{11}$, $R^{12}$ are each independently hydrogen atom, halogen atom, optionally substituted $C_1$-$C_{25}$ alkyl, optionally substituted $C_1$-$C_{25}$ perfluoroalkyl, optionally substituted $C_2$-$C_{25}$ alkene, optionally substituted $C_3$-$C_7$ cycloalkyl, optionally substituted $C_2$-$C_{25}$ alkenyl, optionally substituted $C_3$-$C_{25}$ cycloalkenyl, optionally substituted $C_2$-$C_{25}$ alkynyl, optionally substituted $C_3$-$C_{25}$ cycloalkynyl, optionally substituted $C_1$-$C_{25}$ alkoxy, optionally substituted $C_5$-$C_{24}$ aryloxy, optionally substituted $C_5$-$C_{20}$ heteroaryloxy, optionally substituted $C_5$-$C_{24}$ aryl, optionally substituted $C_5$-$C_{20}$ heteroaryl, optionally substituted $C_7$-$C_{24}$ aralkyl, optionally substituted $C_5$-$C_{24}$ perfluoroaryl, optionally substituted 3-12-membered heterocycle;

wherein $R^{11}$ and $R^{12}$ substituents can be combined together to form a ring selected from a group including $C_3$-$C_7$ cycloalkyl, $C_3$-$C_{25}$ cycloalkenyl, $C_3$-$C_{25}$ cycloalkynyl, $C_5$-$C_{24}$ aryl, $C_3$-$C_{20}$ heteroaryl, $C_5$-$C_{24}$ perfluoroaryl, 3-12-membered heterocycle, which can be substituted independently with one and/or more substituents selected from a group including hydrogen atom, halogen atom, $C_1$-$C_{25}$ alkyl, $C_1$-$C_{25}$ perfluoroalkyl, $C_2$-$C_{25}$ alkene, $C_3$-$C_7$ cycloalkyl, $C_2$-$C_{25}$ alkenyl, $C_3$-$C_{25}$ cycloalkenyl, $C_2$-$C_{25}$ alkynyl, $C_3$-$C_{25}$ cycloalkynyl, $C_1$-$C_{25}$ alkoxy, $C_5$-$C_{24}$ aryloxy, $C_5$-$C_{20}$ heteroaryloxy, $C_5$-$C_{24}$ aryl, $C_5$-$C_{20}$ heteroaryl, $C_7$-$C_{24}$ aralkyl, $C_5$-$C_{24}$ perfluoroaryl, 3-12-membered heterocycle;

is reacted with carbene represented by the Formula 3

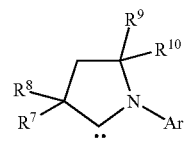

3 wherein:

Ar is an aryl group substituted with hydrogen atoms or optionally substituted with at least one $C_1$-$C_{12}$ alkyl, $C_1$-$C_{12}$ perfluoroalkyl, $C_1$-$C_{12}$ alkoxy, $C_5$-$C_{24}$ aryloxy, $C_5$-$C_{20}$ heteroaryloxy group, or a halogen atom;

$R^7$, $R^8$, $R^9$, and $R^{10}$ are each independently hydrogen atom, or $C_1$-$C_{25}$ alkyl group, $R^7$ and/or $R^8$ can be combined with $R^9$ and/or $R^{10}$ to form cyclic system, can be also independently $C_1$-$C_{12}$ alkyl, $C_3$-$C_{12}$ cycloalkyl, $C_2$-$C_{12}$ alkenyl, $C_5$-$C_{20}$ aryl, $C_1$-$C_5$ perfluoroalkyl, $C_7$-$C_{24}$ aralkyl, and $C_5$-$C_{24}$ perfluoroaryl group, which are optionally substituted with at least one $C_1$-$C_{12}$ alkyl, $C_1$-$C_{12}$ perfluoroalkyl, $C_1$-$C_{12}$ alkoxy, $C_5$-$C_{24}$ aryloxy, $C_5$-$C_{20}$ heteroaryloxy, or a halogen atom;

thus formed reaction mixture is then contacted with the compound represented by the Formula 4

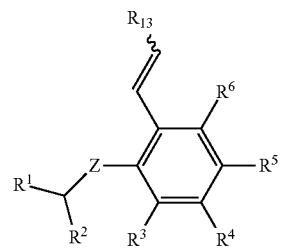

4 wherein:

Z is an atom selected from the group of O, S, NR', wherein R' is $C_1$-$C_{12}$ alkyl, $C_3$-$C_{12}$ cycloalkyl, $C_2$-$C_{12}$ alkenyl, $C_5$-$C_{20}$ aryl, which are optionally substituted with at least one $C_1$-$C_{12}$ alkyl, $C_1$-$C_{12}$ perfluoroalkyl, $C_1$-$C_{12}$ alkoxy, $C_5$-$C_{24}$ aryloxy, $C_5$-$C_{20}$ heteroaryloxy, or a halogen atom;

$R^1$ and $R^2$, are each independently hydrogen atom, $C_1$-$C_{25}$ alkyl group, $C_1$-$C_{25}$ alkoxy group, $C_2$-$C_{25}$ alkenyl group, $C_1$-$C_{12}$ perfluoroalkyl, $C_5$-$C_{20}$ aryl, $C_5$-$C_{24}$ aryloxy, $C_5$-$C_{20}$ heteroaryloxy, or can be combined together to form substituted or unsubstituted $C_4$-$C_{10}$ cyclic or $C_4$-$C_{12}$ polycyclic system, can also be an ester (—COOR'), amide (—CONR'$_2$), formyl (—CHO), ketone (—COR'), and hydroxamic (—CON(OR')(R')) group or a halogen atom, wherein R' is $C_1$-$C_{12}$ alkyl, $C_3$-$C_{12}$ cycloalkyl, $C_2$-$C_{12}$ alkenyl, $C_5$-$C_{20}$ aryl, which are optionally substituted with at least one $C_1$-$C_{12}$ alkyl, $C_1$-$C_{12}$ perfluoroalkyl, $C_1$-$C_{12}$ alkoxy, $C_5$-$C_{24}$ aryloxy, $C_5$-$C_{20}$ heteroaryloxy, or a halogen atom;

$R^3$, $R^4$, $R^5$, $R^6$ are each independently hydrogen atom, $C_1$-$C_{25}$ alkyl group, $C_1$-$C_{25}$ alkoxy group, or $C_2$-$C_{25}$ alkenyl group, wherein $R^3$, $R^4$, $R^5$, $R^6$ substituents can be combined together to form substituted or unsubstituted $C_4$-$C_{10}$ cyclic or $C_4$-$C_{12}$ polycyclic system; can independently also be alkoxy (—OR'), sulphide (—SR'), sulfoxide (—S(O)R'), sulphonium (—S+R'$_2$), sulphone (—SO$_2$R'), sulphonamide (—SO$_2$NR'$_2$), amine (—NR'$_2$), ammonium (—N+R'$_3$), nitro (—NO$_2$), cyano (—CN), phosphonate (—P(O)(OR')$_2$), phosphinate (—P(O)R'(OR')), phosphoninum (—P(OR)$_2$), phosphine (—PR'$_2$), phosphine oxide (—P(O)R'$_2$), phosphonium (-p+R'$_3$), carboxy (—COOH), ester (—COOR'), amide (—CONR'$_2$, or —NR'C(O)R'), formyl (—CHO), ketone (—COR') group, wherein R' is $C_1$-$C_5$ alkyl, $C_1$-$C_5$ perfluoroalkyl, $C_5$-$C_{24}$ aryl, $C_7$-$C_{24}$ aralkyl, $C_5$-$C_{24}$ perfluoroaryl; $R^{13}$ is a hydrogen atom, $C_1$-$C_{25}$ alkyl group, $C_1$-$C_{25}$ alkoxy group, $C_2$-$C_{25}$ alkenyl group, $C_1$-$C_{12}$ perfluoroalkyl, $C_5$-$C_{20}$ aryl, $C_5$-$C_{24}$ aryloxy, $C_5$-$C_{20}$ heteroaryloxy, or can be combined together to form substituted or unsubstituted $C_4$-$C_{10}$ cyclic or $C_4$-$C_{12}$ polycyclic system or a halogen atom;
to form the compound represented by the Formula 1.

Preferably, the reaction mixture is contacted with the compound represented by the Formula 4 in the presence of phosphine ligand PR'$_3$ scavenger and/or CAAC ligand scavenger.

Preferably, carbenes represented by the Formula 3 are provided in the reaction medium by their generation in situ from suitable carbene precursors, CAAC salts represented by the Formula 3a,

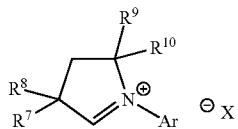

3a wherein:
Ar is an aryl group substituted with hydrogen atoms or optionally substituted with at least one $C_1$-$C_{12}$ alkyl group, $C_1$-$C_{12}$ perfluoroalkyl, $C_1$-$C_{12}$ alkoxy, $C_5$-$C_{24}$ aryloxy, $C_5$-$C_{20}$ heteroaryloxy, or a halogen atom;
$R^7$, $R^8$, $R^9$, and $R^{10}$ are each independently hydrogen atom or $C_1$-$C_{25}$ alkyl group, $R^7$ and/or $R^8$ can be combined with $R^9$ and/or $R^{10}$ to form cyclic system, can be also independently $C_1$-$C_{12}$ alkyl, $C_3$-$C_{12}$ cycloalkyl, $C_2$-$C_{12}$ alkenyl, $C_5$-$C_{20}$ aryl, $C_1$-$C_5$ perfluoroalkyl, $C_7$-$C_{24}$ aralkyl, and $C_5$-$C_{24}$ perfluoroaryl group, which are optionally substituted with at least one $C_1$-$C_{12}$ alkyl, $C_1$-$C_{12}$ perfluoroalkyl, $C_1$-$C_{12}$ alkoxy, $C_5$-$C_{24}$ aryloxy, $C_5$-$C_{20}$ heteroaryloxy, or a halogen atom;
X— is a halide anion, or BF$_4$—, PF$_6$—, ClO$_4$—, CF$_3$SO$_2$O—.
involving contacting the compound represented by the Formula 3a with a suitable base selected from potassium N,N'-bis(trimethylsilyl)amide, lithium N,N'-bis(trimethylsilyl)amide, sodium N,N'-bis(trimethylsilyl)amide, potassium tert-amylate, potassium tert-butoxide, and sodium hydride.

Preferably, carbenes represented by the Formula 3 are provided in the reaction medium by their generation in situ from suitable carbene precursors represented by the Formula 3a, which are contacted with a base such as alkali metal N,N'-bis(trimethylsilyl)amide.

Preferably, carbenes represented by the Formula 3 are provided in the reaction medium by their thermal generation in situ from suitable carbene precursors represented by the Formula 3b which are chloroform or alcohol adducts,

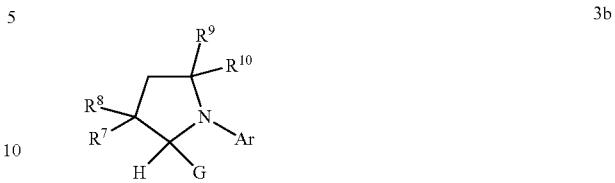

wherein:
G is CCl$_3$ or OR', wherein R' is $C_1$-$C_{12}$ alkyl, $C_3$-$C_{12}$ cycloalkyl, $C_2$-$C_{12}$ alkenyl, or $C_5$-$C_{20}$ aryl, which is optionally substituted with at least one $C_1$-$C_{12}$ alkyl, $C_1$-$C_{12}$ perfluoroalkyl, $C_1$-$C_{12}$ alkoxy, $C_5$-$C_{24}$ aryloxy, $C_5$-$C_{20}$ heteroaryloxy or a halogen atom;
Ar is an aryl group substituted with hydrogen atoms or optionally substituted with at least one $C_1$-$C_{12}$ alkyl, $C_1$-$C_{12}$ perfluoroalkyl, $C_1$-$C_{12}$ alkoxy, $C_5$-$C_{24}$ aryloxy, $C_5$-$C_{20}$ heteroaryloxy group, or a halogen atom; R7, R8, R9, and R10 are each independently hydrogen atom or $C_1$-$C_{25}$ alkyl group, R7 and/or R8 can be combined with R9 and/or R10 to form cyclic system, can be also independently $C_1$-$C_{12}$ alkyl, $C_3$-$C_{12}$ cycloalkyl, $C_2$-$C_{12}$ alkenyl, $C_5$-$C_{20}$ aryl, $C_1$-$C_5$ perfluoroalkyl, $C_7$-$C_{24}$ aralkyl, and $C_5$-$C_{24}$ perfluoroaryl group, which are optionally substituted with at least one $C_1$-$C_{12}$ alkyl, $C_1$-$C_{12}$ perfluoroalkyl, $C_1$-$C_{12}$ alkoxy, $C_5$-$C_{24}$ aryloxy, $C_5$-$C_{20}$ heteroaryloxy, or a halogen atom.

Preferably, alkylidene ruthenium complex represented by the Formula 2, is contacted with the compound represented by the Formula 3c, which acts as CAAC carbene ligand donor represented by the Formula 3,

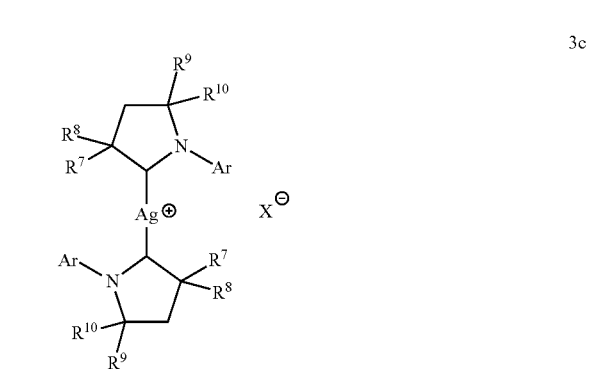

wherein:
Ar is an aryl group substituted with hydrogen atoms or optionally substituted with at least one $C_1$-$C_{12}$ alkyl, $C_1$-$C_{12}$ perfluoroalkyl, $C_1$-$C_{12}$ alkoxy, $C_6$-$C_{24}$ aryloxy, and $C_6$-$C_{20}$ heteroaryloxy group, or a halogen atom; $R^7$, $R^8$, $R^9$, and $R^{10}$ are each independently hydrogen atom or $C_1$-$C_{26}$ alkyl group, $R^7$ and/or $R^8$ can be combined with $R^9$ and/or $R^{10}$ to form cyclic system, can be also independently $C_1$-$C_{12}$ alkyl, $C_3$-$C_{12}$ cycloalkyl, $C_2$-$C_{12}$ alkenyl, $C_6$-$C_{20}$ aryl, $C_1$-$C_5$ perfluoroalkyl, $C_7$-$C_{24}$ aralkyl, and $C_5$-$C_{24}$ perfluoroaryl group, which are optionally substituted with at least one $C_1$-$C_{12}$ alkyl, $C_1$-$C_{12}$ perfluoroalkyl, $C_1$-$C_{12}$ alkoxy, $C_6$-$C_{24}$ aryloxy, $C_6$-$C_{20}$ heteroaryloxy, or a halogen atom;
X is a halide anion or BF$_4$—, PF$_6$—, ClO$_4$—, CF$_3$SO$_3$—.

Preferably, carbenes represented by the Formula 3 are provided in the reaction medium by their direct adding to the reaction mixture.

Preferably, the alkylidene ruthenium complex represented by the Formula 2 is reacted with the carbine represented by the Formula 3 to form an intermediate compound represented by the Formula 5

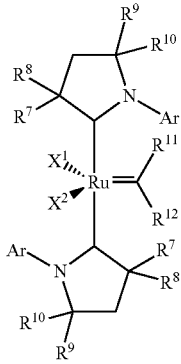

5 which is then contacted with the compound represented by the Formula 4

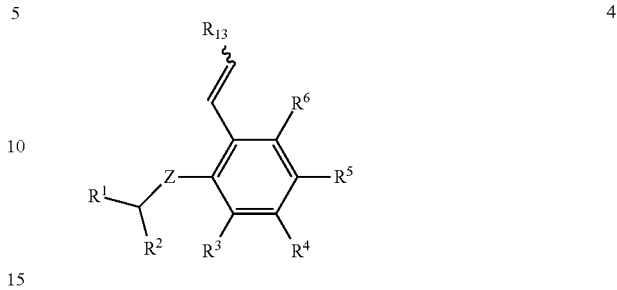

4 wherein:

Z is an atom selected from a group of O, S, NR', wherein R' is $C_1$-$C_{12}$ alkyl, $C_3$-$C_{12}$ cycloalkyl, $C_2$-$C_{12}$ alkenyl, $C_5$-$C_{20}$ aryl, which are optionally substituted with at least one $C_1$-$C_{12}$ alkyl, $C_1$-$C_{12}$ perfluoroalkyl, $C_1$-$C_{12}$ alkoxy, $C_5$-$C_{24}$ aryloxy, $C_5$-$C_{20}$ heteroaryloxy, or a halogen atom;

$R^1$ and $R^2$ are each independently hydrogen atom, $C_1$-$C_{25}$ alkyl group, $C_1$-$C_{25}$ alkoxy group, $C_2$-$C_{25}$ alkenyl group, $C_1$-$C_{12}$ perfluoroalkyl, $C_5$-$C_{20}$ aryl, $C_5$-$C_{24}$ aryloxy, $C_5$-$C_{20}$ heteroaryloxy, or can be combined together to form substituted or unsubstituted $C_4$-$C_{10}$ cyclic or $C_4$-$C_{12}$ polycyclic system, can also be an ester (—COOR), amide (—CONR'$_2$), formyl (—CHO), ketone (—COR'), and hydroxamic (—CON(OR')(R')) group or a halogen atom, wherein R' is $C_1$-$C_{12}$ alkyl, $C_3$-$C_{12}$ cycloalkyl, $C_2$-$C_{12}$ alkenyl, $C_5$-$C_{20}$ aryl, which are optionally substituted with at least one $C_1$-$C_{12}$ alkyl, $C_1$-$C_{12}$ perfluoroalkyl, $C_1$-$C_{12}$ alkoxy, $C_5$-$C_{24}$ aryloxy, $C_5$-$C_{20}$ heteroaryloxy, or a halogen atom;

$R^3$, $R^4$, $R^5$, $R^6$ are each independently hydrogen atom, $C_1$-$C_{25}$ alkyl group, $C_1$-$C_{25}$ alkoxy group, or $C_2$-$C_{25}$ alkenyl group, wherein $R^3$, $R^4$, $R^5$, $R^6$ substituents can be combined together to form substituted or unsubstituted $C_4$-$C_{10}$ cyclic or $C_4$-$C_{12}$ polycyclic system; can also independently be an alkoxy (—OR'), sulphide (—SR), sulfoxide (—S(O)R'), sulphonium (—S+R'$_2$), sulphone (—SO$_2$R), sulphonamide (—SO$_2$NR'$_2$), amine (—NR'$_2$), ammonium (—N+R'$_3$), nitro (—NO$_2$), cyano (—CN), phosphonate (—P(O)(OR')$_2$), phosphinate (—P(O)R'(OR')), phosphoninum (—P(OR)$_2$), phosphine (—PR'$_2$), phosphine oxide (—P(O)R'$_2$), phosphonium (—P+R'$_3$), carboxy (—COOH), ester (—COOR'), amide (—CONR'$_2$, or —NR'C(O)R'), formyl (—CHO), and ketone (—COR') group, wherein R' is $C_1$-$C_5$ alkyl, $C_1$-$C_5$ perfluoroalkyl, $C_5$-$C_{24}$ aryl, $C_1$-$C_{24}$ aralkyl, $C_5$-$C_{24}$ perfluoroaryl;

$R^{13}$ is a hydrogen atom, $C_1$-$C_{25}$ alkyl group, $C_1$-$C_{25}$ alkoxy group, $C_2$-$C_{25}$ alkenyl group, $C_1$-$C_{12}$ perfluoroalkyl, $C_5$-$C_{20}$ aryl, $C_5$-$C_{24}$ aryloxy, $C_5$-$C_{20}$ heteroaryloxy, or can be combined together to form substituted or unsubstituted $C_4$-$C_{10}$ cyclic or $C_4$-$C_{12}$ polycyclic system or a halogen atom;

to form the compound represented by the Formula 1.

Preferably, Compound 5 is reacted with the Compound 4 in the presence of the phosphine ligand scavenger PR'$_3$ and/or CAAC ligand scavenger.

Preferably, as the phosphine ligand scavenger PR'$_3$ and/or the CAAC ligand scavenger a compound selected from copper(I) salts and/or HCl is used.

Preferably, all reaction steps are conducted in a polar and/or nonpolar solvent, preferably in aliphatic or aromatic hydrocarbons, over a period of 1 minute to 24 hours.

wherein:

$X^1$ and $X^2$ are each independently an anionic ligand selected from halogen atoms, —CN, —SCN, —OR', —SR', —O(C=O)R', —O(SO$_2$)R', and —OSi(R')$_3$ group, wherein R' is $C_1$-$C_{12}$ alkyl, $C_3$-$C_{12}$ cycloalkyl, $C_2$-$C_{12}$ alkenyl, $C_5$-$C_{20}$ aryl, which are optionally substituted with at least one $C_1$-$C_{12}$ alkyl, $C_1$-$C_{12}$ perfluoroalkyl, $C_1$-$C_{12}$ alkoxy, $C_6$-$C_{24}$ aryloxy, $C_6$-$C_{20}$ heteroaryloxy, or a halogen atom;

Ar is an aryl group substituted with hydrogen atoms or optionally substituted with at least one $C_1$-$C_{12}$ alkyl, $C_1$-$C_{12}$ perfluoroalkyl, $C_1$-$C_{12}$ alkoxy, $C_6$-$C_{24}$ aryloxy, and $C_6$-$C_{20}$ heteroaryloxy group, or a halogen atom; $R^7$, $R^8$, $R^9$, and $R^{10}$ are each independently hydrogen atom or $C_1$-$C_{26}$ alkyl group, $R^7$ and/or $R^8$ can be combined with $R^9$ and/or $R^{10}$ to form cyclic system, can be also independently $C_1$-$C_{12}$ alkyl, $C_3$-$C_{12}$ cycloalkyl, $C_2$-$C_{12}$ alkenyl, $C_6$-$C_{20}$ aryl, $C_1$-$C_5$ perfluoroalkyl, $C_7$-$C_{24}$ aralkyl, and $C_5$-$C_{24}$ perfluoroaryl group, which are optionally substituted with at least one $C_1$-$C_{12}$ alkyl, $C_1$-$C_{12}$ perfluoroalkyl, $C_1$-$C_{12}$ alkoxy, $C_6$-$C_{24}$ aryloxy, $C_6$-$C_{20}$ heteroaryloxy, or a halogen atom;

$R^{11}$, $R^{12}$ are each independently hydrogen atom, halogen atom, optionally substituted $C_1$-$C_{25}$ alkyl, optionally substituted $C_1$-$C_{25}$ perfluoroalkyl, optionally substituted $C_2$-$C_{25}$ alkene, optionally substituted $C_3$-$C_7$ cycloalkyl, optionally substituted $C_2$-$C_{25}$ alkenyl, optionally substituted $C_3$-$C_{25}$ cycloalkenyl, optionally substituted $C_2$-$C_{25}$ alkynyl, optionally substituted $C_3$-$C_{25}$ cycloalkynyl, optionally substituted $C_1$-$C_{25}$ alkoxy, optionally substituted $C_5$-$C_{24}$ aryloxy, optionally substituted $C_5$-$C_{20}$ heteroaryloxy, optionally substituted $C_5$-$C_{24}$ aryl, optionally substituted $C_5$-$C_{20}$ heteroaryl, optionally substituted $C_7$-$C_{24}$ aralkyl, optionally substituted $C_5$-$C_{24}$ perfluoroaryl, optionally substituted 3-12-membered heterocycle;

wherein $R^{11}$ and $R^{12}$ substituents can be combined together to form a ring selected from a group including $C_3$-$C_7$ cycloalkyl, $C_3$-$C_{25}$ cycloalkenyl, $C_3$-$C_{25}$ cycloalkynyl, $C_5$-$C_{24}$ aryl, $C_5$-$C_{20}$ heteroaryl, $C_5$-$C_{24}$ perfluoroaryl, 3-12-membered heterocycle, which can be substituted independently with one and/or more substituents selected from a group including hydrogen atom, halogen atom, $C_1$-$C_{25}$ alkyl, $C_1$-$C_{25}$ perfluoroalkyl, $C_2$-$C_{25}$ alkene, $C_3$-$C_7$ cycloalkyl, $C_2$-$C_{25}$ alkenyl, $C_3$-$C_{25}$ cycloalkenyl, $C_2$-$C_{25}$ alkynyl, $C_3$-$C_{25}$ cycloalkynyl, $C_1$-$C_{25}$ alkoxy, $C_5$-$C_{24}$ aryloxy, $C_5$-$C_{20}$ heteroaryloxy, $C_5$-$C_{24}$ aryl, $C_5$-$C_{20}$ heteroaryl, $C_7$-$C_{24}$ aralkyl, $C_5$-$C_{24}$ perfluoroaryl, 3-12-membered heterocycle;

The invention provides also a compound represented by the Formula 1,

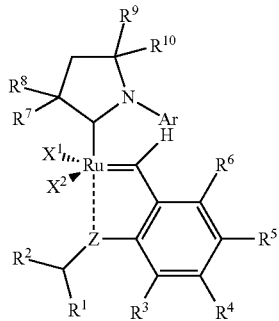

wherein:
$X^1$ and $X^2$ are each independently an anionic ligand selected from halogen atoms, —CN, —SCN, —OR', —SR', —O(C=O)R', —O(SO$_2$)R', and —OSi(R')$_3$ group, wherein R' is $C_1$-$C_{12}$ alkyl, $C_3$-$C_{12}$ cycloalkyl, $C_2$-$C_{12}$ alkenyl, $C_5$-$C_{20}$ aryl, which are optionally substituted with at least one $C_1$-$C_{12}$ alkyl, $C_1$-$C_{12}$ perfluoroalkyl, $C_1$-$C_{12}$ alkoxy, $C_5$-$C_{24}$ aryloxy, $C_5$-$C_{20}$ heteroaryloxy, or a halogen atom;
Z is an atom selected from a group of O, S, NR', wherein R' is $C_1$-$C_{12}$ alkyl, $C_3$-$C_{12}$ cycloalkyl, $C_2$-$C_{12}$ alkenyl, $C_5$-$C_{20}$ aryl, which are optionally substituted with at least one $C_1$-$C_{12}$ alkyl, $C_1$-$C_{12}$ perfluoroalkyl, $C_1$-$C_{12}$ alkoxy, $C_5$-$C_{24}$ aryloxy, $C_5$-$C_{20}$ heteroaryloxy, or a halogen atom;
Ar is an aryl group substituted with hydrogen atoms or optionally substituted with at least one $C_1$-$C_{12}$ alkyl, $C_1$-$C_{12}$ perfluoroalkyl, $C_1$-$C_{12}$ alkoxy, $C_5$-$C_{24}$ aryloxy, $C_5$-$C_{20}$ heteroaryloxy group, or a halogen atom;
$R^1$ and $R^2$ are each independently hydrogen atom, $C_1$-$C_{25}$ alkyl group, $C_1$-$C_{25}$ alkoxy group, $C_2$-$C_{25}$ alkenyl group, $C_1$-$C_{12}$ perfluoroalkyl, $C_5$-$C_{20}$ aryl, $C_5$-$C_{24}$ aryloxy, $C_5$-$C_{20}$ heteroaryloxy, or can be combined together to form substituted or unsubstituted $C_4$-$C_{10}$ cyclic or $C_4$-$C_{12}$ polycyclic system, can also be an ester (—COOR'), amide (—CONR'$_2$), formyl (—CHO), ketone (—COR'), and hydroxamic (—CON(OR')(R')) group or a halogen atom, in which R' is $C_1$-$C_{12}$ alkyl, $C_3$-$C_{12}$ cycloalkyl, $C_2$-$C_{12}$ alkenyl, $C_5$-$C_{20}$ aryl, which are optionally substituted with at least one $C_1$-$C_{12}$ alkyl, $C_1$-$C_{12}$ perfluoroalkyl, $C_1$-$C_{12}$ alkoxy, $C_5$-$C_{24}$ aryloxy, $C_5$-$C_{20}$ heteroaryloxy, or a halogen atom;
$R^3$, $R^4$, $R^5$, $R^6$ are each independently hydrogen atom, sulfoxide group (—S(O)R'), sulphonamide group (—SO$_2$NR'2), phosphonate group (—P(O)(OR')z), phosphinate group (—P(O)R'(OR')), phosphoninum group (—P(OR')z), phosphine group (—PR'2), nitro group (—NO2), nitroso group (—NO), carboxy group (—COOH), ester group (—COOR'), formyl group (—CHO), and ketone group (—COR'), wherein R' is $C_1$-$C_5$ alkyl, $C_1$-$C_5$ perfluoroalkyl, $C_5$-$C_{24}$ aryl, $C_7$-$C_{24}$ aralkyl, $C_5$-$C_{24}$ perfluoroaryl; wherein, when R1 and R2 are —CH3 group, then at least one of R3, R4, R5, R6 substituents is not hydrogen atom;
$R^7$, $R^8$, $R^9$, and $R^{10}$ are each independently hydrogen atom or $C_1$-$C_{25}$ alkyl group, $R^7$ and/or $R^8$ can be combined with $R^9$ and/or $R^{10}$ to form cyclic system, are also independently $C_1$-$C_{12}$ alkyl, $C_3$-$C_{12}$ cycloalkyl, $C_2$-$C_{12}$ alkenyl, $C_5$-$C_{20}$ aryl, $C_1$-$C_5$ perfluoroalkyl, $C_7$-$C_{24}$ aralkyl, and $C_5$-$C_{24}$ perfluoroaryl group, which are optionally substituted with at least one $C_1$-$C_{12}$ alkyl, $C_1$-$C_{12}$ perfluoroalkyl, $C_1$-$C_{12}$ alkoxy, $C_5$-$C_{24}$ aryloxy, $C_5$-$C_{20}$ heteroaryloxy, or halogen.

Preferably, the invention provides a compound of a structure represented by the formula selected from 1b, 1c, 1e, 1f, 1h, 1i, 1j, 1k, 1l:

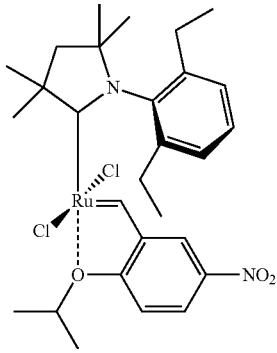

1b

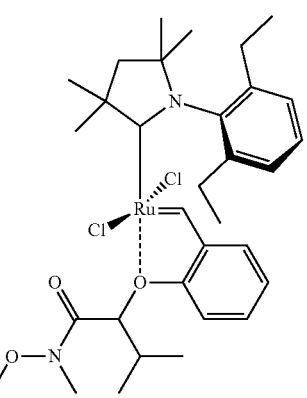

1c

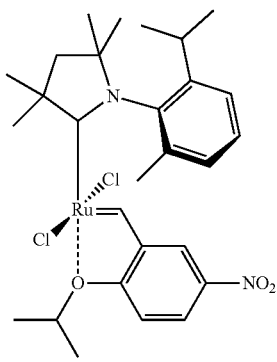

1e

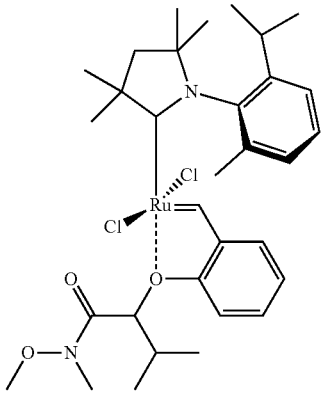

1f

-continued

1h 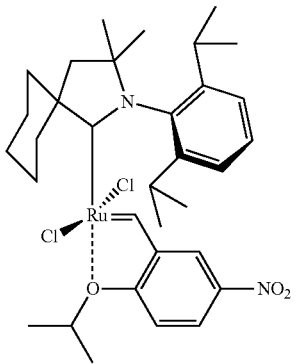

1i 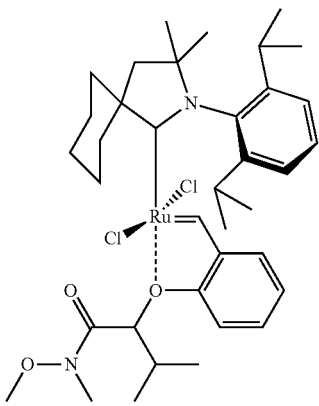

1j 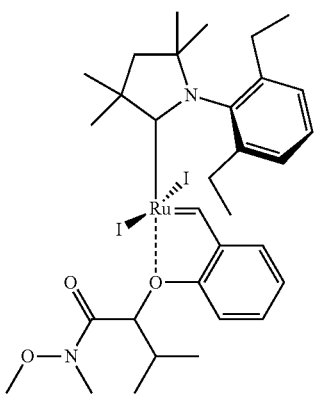

1k 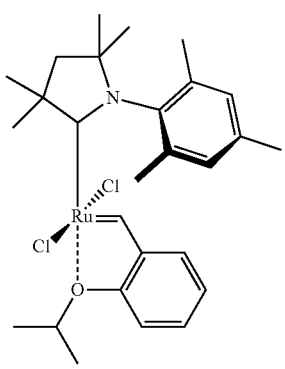

-continued

11 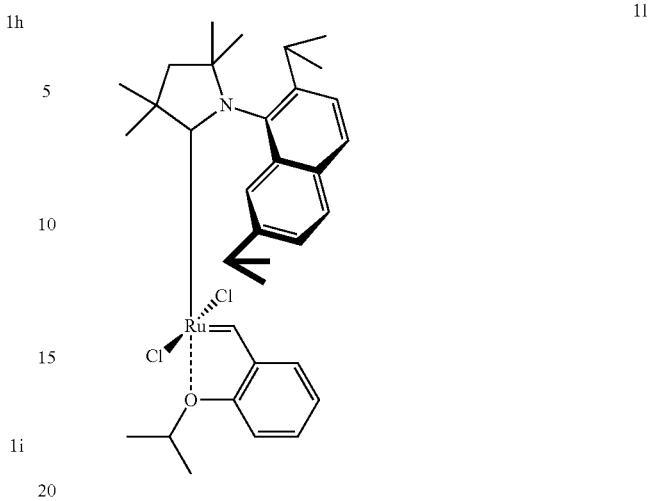

The invention provides also a compound represented by the Formula 5,

5 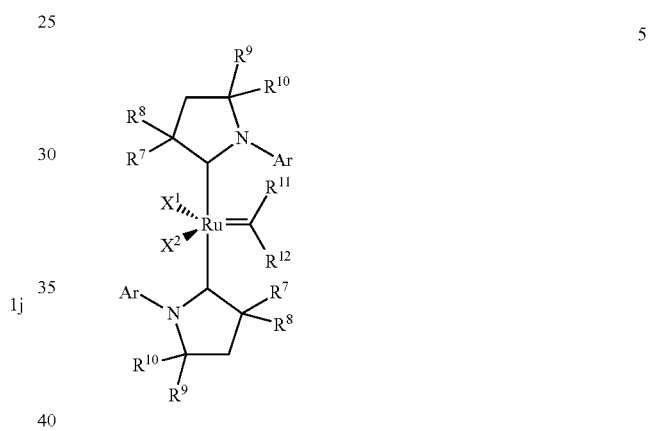

wherein:
$X^1$ and $X^2$ are each independently an anionic ligand selected from halogen atoms, —CN, —SCN, —OR', —SR', —O(C=O)R', —O(SO$_2$)R', and —OSi(R')$_3$ group, wherein R' is $C_1$-$C_{12}$ alkyl, $C_3$-$C_{12}$ cycloalkyl, $C_2$-$C_{12}$ alkenyl, $C_5$-$C_{20}$ aryl, which are optionally substituted with at least one $C_1$-$C_{12}$ alkyl, $C_1$-$C_{12}$ perfluoroalkyl, $C_1$-$C_{12}$ alkoxy, $C_5$-$C_{24}$ aryloxy, $C_5$-$C_{20}$ heteroaryloxy, or a halogen atom;
Ar is an aryl group substituted with hydrogen atoms or optionally substituted with at least one $C_1$-$C_{12}$ alkyl, $C_1$-$C_{12}$ perfluoroalkyl, $C_1$-$C_{12}$ alkoxy, $C_5$-$C_{24}$ aryloxy, and $C_5$-$C_{20}$ heteroaryloxy group, or a halogen atom; $R^7$, $R^8$, $R^9$, and $R^{10}$ are each independently hydrogen atom or $C_1$-$C_{25}$ alkyl group, $R^7$ and/or $R^8$ can be combined with $R^9$ and/or $R^{10}$ to form cyclic system, can be also independently $C_1$-$C_{12}$ alkyl, $C_3$-$C_{12}$ cycloalkyl, $C_2$-$C_{12}$ alkenyl, $C_5$-$C_{20}$ aryl, $C_1$-$C_5$ perfluoroalkyl, $C_7$-$C_{24}$ aralkyl, $C_5$-$C_{24}$ perfluoroaryl, which are optionally substituted with at least one $C_1$-$C_{12}$ alkyl, $C_1$-$C_{12}$ perfluoroalkyl, $C_1$-$C_{12}$ alkoxy, $C_5$-$C_{24}$ aryloxy, and $C_5$-$C_{20}$ heteroaryloxy group, or a halogen atom;
$R^{11}$, $R^{12}$ are each independently hydrogen atom, halogen atom, optionally substituted $C_1$-$C_{25}$ alkyl, optionally substituted $C_1$-$C_{25}$ perfluoroalkyl, optionally substituted $C_2$-$C_{25}$ alkene, optionally substituted $C_3$-$C_7$ cycloalkyl, optionally substituted $C_2$-$C_{25}$ alkenyl, optionally substituted $C_3$-$C_{25}$ cycloalkenyl, optionally substituted $C_2$-$C_{25}$ alkynyl, optionally substituted $C_3$-$C_{25}$ cycloalkynyl, optionally substituted $C_1$-$C_{25}$ alkoxy, optionally substituted $C_5$-$C_{24}$ aryloxy, optionally substituted $C_5$-$C_{20}$ heteroaryloxy, optionally substituted $C_5$-$C_{24}$ aryl, optionally substituted $C_5$-$C_{20}$ heteroaryl, optionally substituted $C_7$-$C_{24}$ aralkyl, optionally substituted $C_5$-$C_{24}$ perfluoroaryl, optionally substituted 3-12-membered heterocycle;

wherein $R^{11}$ and $R^{12}$ substituents can be combined together to form a ring selected from a group including $C_3$-$C_7$ cycloalkyl, $C_3$-$C_{25}$ cycloalkenyl, $C_3$-$C_{25}$ cycloalkynyl, $C_5$-$C_{24}$ aryl, $C_5$-$C_{20}$ heteroaryl, $C_5$-$C_{24}$ perfluoroaryl, 3-12-membered heterocycle, which can be substituted independently with one and/or more substituents selected from a group including hydrogen atom, halogen atom, $C_1$-$C_{25}$ alkyl, $C_1$-$C_{25}$ perfluoroalkyl, $C_2$-$C_{25}$ alkene, $C_3$-$C_7$ cycloalkyl, $C_2$-$C_{25}$ alkenyl, $C_3$-$C_{25}$ cycloalkenyl, $C_2$-$C_{25}$ alkynyl, $C_3$-$C_{25}$ cycloalkynyl, $C_1$-$C_{25}$ alkoxy, $C_5$-$C_{24}$ aryloxy, $C_5$-$C_{20}$ heteroaryloxy, $C_5$-$C_{24}$ aryl, $C_5$-$C_{20}$ heteroaryl, $C_7$-$C_{24}$ aralkyl, $C_5$-$C_{24}$ perfluoroaryl, 3-12-membered heterocycle.

Preferably, invention relates to a compound of a structure represented by the formula selected from 5a-5j, (wherein these compounds may be in a rotamer form):

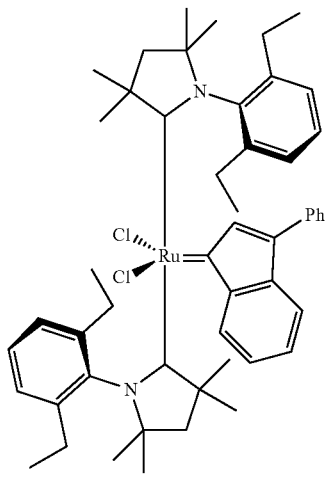

5a

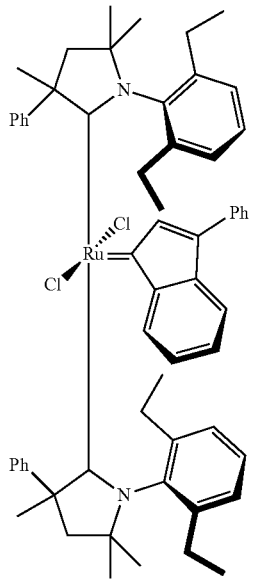

5c

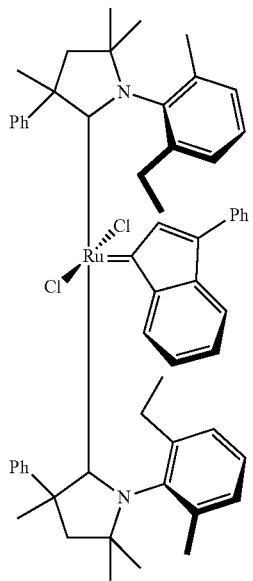

5d

5e
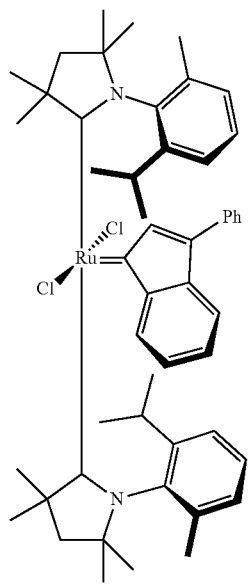
5f
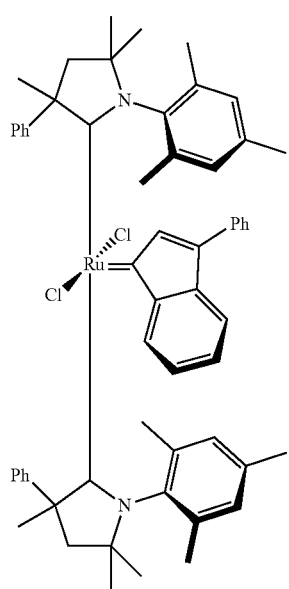
5g
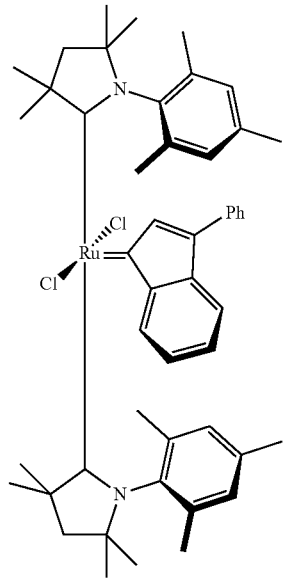
5h
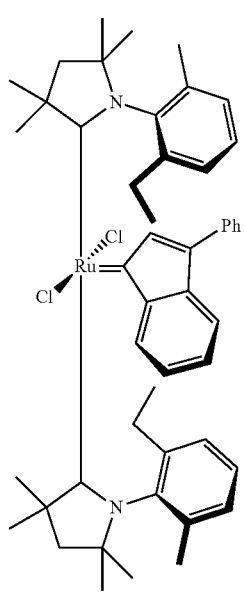

-continued

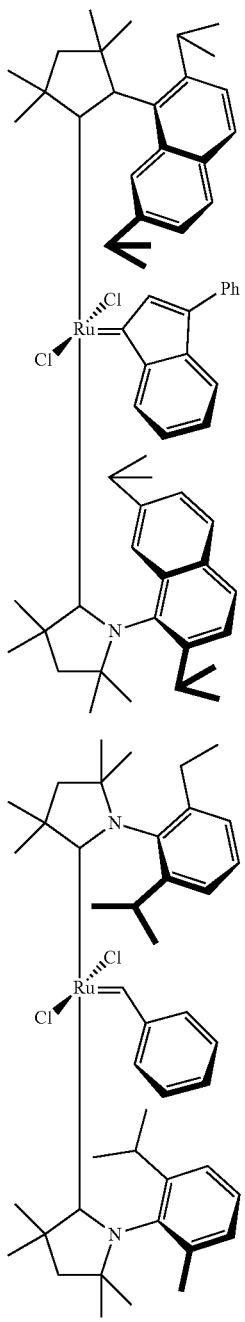

The invention provides also the use of a compound represented by the Formula 1, obtained by the above-mentioned method, as a precatalyst and/or catalyst in olefin metathesis reactions, particularly in ring-closing metathesis (RCM), homometathesis, cross-metathesis (CM), ethenolysis, and isomerisation reactions, in reaction of diastereoselective ring-rearrangement metathesis (DRRM), in "alkene-alkyne" (en-yn) type metathesis or ROMP type polymerisation reactions.

Preferably, compound represented by the Formula 1 is used as the precatalyst and/or catalyst in a reaction mixture over a period of 1 minute to 24 hours in organic solvents or without solvent.

The invention relates also to the use of compound represented by the Formula 1, obtained as described above, as a substrate for the synthesis of other ruthenium complex compounds which are precatalysts and/or catalysts for olefin metathesis.

The present invention provides also the use of the compound represented by the Formula 5 as the precatalyst and/or catalyst in olefin metathesis reactions, particularly in ring-closing metathesis (RCM), homometathesis, cross-metathesis (CM), ethenolysis, and isomerisation reactions, in reaction of diastereoselective ring-rearrangement metathesis (DRRM), in "alkene-alkyne" (en-yn) type metathesis or ROMP type polymerisation reactions, and also the use of the compound represented by the Formula 5 as the precatalyst and/or catalyst in olefin metathesis reactions in the presence of a CAAC ligand scavenger.

The present invention and its advantageous effects are shown in the figures, wherein.

Figure 1:
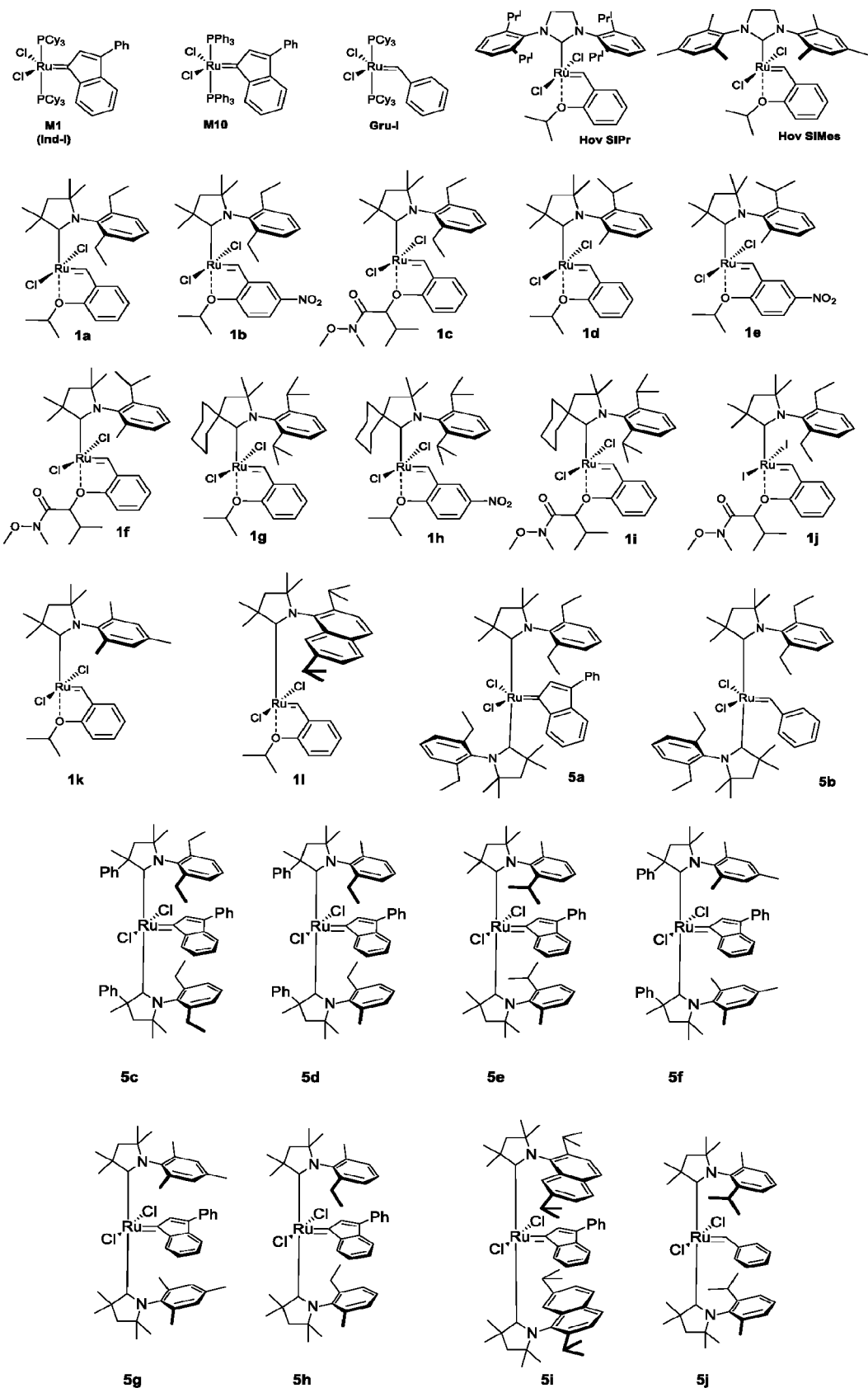
FIG. 1 shows structures of the compounds of the present invention.

Terms used the present specification have the following meanings:

The term "halogen atom" or "halogen" means an element selected from F, Cl, Br, I.

The term "carbene" means a particle containing a neutral carbon atom of a valence number two and two unpaired (triplet state) or paired (singlet state) valence electrons. The term "carbene" encompasses also carbene analogues, wherein the carbon atom is replaced by other chemical element such as boron, silicon, germanium, tin, lead, nitrogen, phosphorus, sulphur, selenium, and tellurium.

The term "alkyl" refers to a saturated, straight, or branched hydrocarbon substituent with an indicated carbon atom number. Examples of an alkyl substituent are -methyl, -ethyl, -n-propyl, -n-butyl, -n-pentyl, -n-hexyl, -n-heptyl, -n-octyl, -n-nonyl, and -n-decyl. Representative branched —(C1-C10)alkyls include -isopropyl, -sec-butyl, -isobutyl, -tert-butyl, -isopentyl, -neopentyl, -1-methylbutyl, -2-methylbutyl, -3-methylbutyl, -1,1-dimethylpropyl, -1,2-dimethylpropyl, -1-methylpentyl, -2-methylpentyl, -3-methylpentyl, -4-methylpentyl, -1-ethylbutyl, -2-ethylbutyl, -3-ethylbutyl, -1,1-dimethylbutyl, -1,2-dimethylbutyl, -1,3-dimethylbutyl, -2,2-dimethylbutyl, -2,3-dimethylbutyl, -3,3-dimethylbutyl, -1-methyl hexyl, -2-methylhexyl, -3-methylhexyl, -4-methylhexyl, -5-methylhexyl, -1,2-dimethylpentyl, -1,3-dimethylpentyl, -1,2-dimethylhexyl, -1,3-dimethylhexyl, -3,3-dimethylhexyl, -1,2-dimethylheptyl, -1,3-dimethylheptyl, and -3,3-dimethylheptyl, and the like.

The term "alkoxy" refers to an alkyl substituent as described above connected by an oxygen atom.

The term "perfluoroalkyl" means an alkyl group as described above, in which all hydrogen atoms were replaced with the same or different type of halogen atoms.

The term "cycloalkyl" refers to a saturated mono- or polycyclic hydrocarbon substituent with an indicated carbon atom number. Examples of a cycloalkyl substituent are -cyclopropyl, -cyclobutyl, -cyclopentyl, -cyclohexyl, -cycloheptyl, -cyclooctyl, -cyclononyl, -cyclodecyl, and the like.

The term "alkenyl" refers to a saturated, straight, or branched acyclic hydrocarbon substituent with an indicated carbon atom number and containing at least one carbon-carbon double bond. Examples of an alkenyl substituent are -vinyl, -ally, -1-butenyl, -2-butenyl, -isobutylenyl, -1-pentenyl, -2-pentenyl, -3-methyl-1-butenyl, -2-methyl-2-butenyl, -2,3-di-methyl-2-butenyl, -1-hexenyl, -2-hexenyl, -3-hexenyl, -1-heptenyl, -2-heptenyl, -3-heptenyl, -1-octenyl, -2-octenyl, -3-octenyl, -1-nonenyl, -2-nonenyl, -3-nonenyl, -1-decenyl, -2-decenyl, -3-decenyl, and the like.

The term "cycloalkenyl" refers to a saturated mono- or polycyclic hydrocarbon substituent with an indicated carbon atom number and containing at least one carbon-carbon double bond. Examples of cycloalkenyl substituent are -cyclopentenyl, -cyclopentadienyl, -cyclohexenyl, -cyclohexadienyl, -cycloheptenyl, -cycloheptadienyl, -cycloheptatrienyl, -cyclooctenyl, -cyclooctadienyl, -cyclooctatrienyl, -cyclooctatetraenyl, -cyclononenyl, -cyclononadienyl, -cyclodecenyl, -cyclodecadienyl, and the like.

The term "alkynyl" refers to a saturated, straight, or branched acyclic hydrocarbon substituent with an indicated carbon atom number and containing at least one carbon-carbon triple bond. Examples of an alkynyl substituent are -acetylenyl, -propynyl, -1-butynyl, -2-butynyl, -1-pentynyl, -2-pentynyl, -3-methylo-1-butynyl, -4-pentynyl, -1-hexynyl, -2-hexynyl, -5-hexynyl, and the like.

The term "cycloalkynyl" refers to a saturated mono- or polycyclic hydrocarbon substituent with an indicated carbon atom number and containing at least one carbon-carbon triple bond. Examples of cycloalkynyl substituent are -cyclohexynyl, -cycloheptynyl, -cyclooctynyl, and the like.

The term "aryl" refers to an aromatic mono- or polycyclic hydrocarbon substituent with an indicated carbon atom number. Examples of an aryl substituent are -phenyl, -tolyl, -xylyl, -naphthyl, -2,4,6-trimethylphenyl, -2-fluorophenyl, -4-fluorophenyl, -2,4,6-trifluorophenyl, -2,6-difluorophenyl, -4-nitrophenyl, and the like.

The term "aralkyl" refers to an alkyl substituent, as described above, substituted with at least one aryl as described above. Examples of an aralkyl substituent are -benzyl, -diphenylmethyl, -triphenylmethyl, and the like.

The term "heteroaryl" refers to an aromatic mono- or polycyclic hydrocarbon substituent with an indicated carbon atom number, wherein at least one carbon atom was replaced with a heteroatom selected from O, N and S atoms. Examples of heteroaryl substituent are -furyl, -thienyl, -imidazolyl, -oxazolyl, -thiazolyl, -isoxazolyl, triazolyl, -oxadiazolyl, -thiadiazolyl, -tetrazolyl, -pyridyl, -pyrimidyl, -triazinyl, -indolyl, -benzo[b]furyl, -benzo[b]thienyl, -indazolyl, -benzimidazolyl, -azaindolyl, -quinolyl, -isoquinolyl, -carbazolyl, and the like.

The term "heterocycle" refers to a saturated or partly unsaturated, mono- or polycyclic hydrocarbon substituent with an indicated carbon atom number, wherein at least one carbon atom was replaced with a heteroatom selected from O, N and S atoms. Examples of a heterocyclic substituent are furyl, thiophenyl, pyrrolyl, oxazolyl, imidazolyl, thiazolyl, isoxazolyl, pyrazolyl, isothiazolyl, triazinyl, pyrrolidinonyl, pyrrolidinyl, hydantoinyl, oxiranyl, oxetanyl, tetrahydrofuranyl, tetrahydrothiophenyl, quinolinyl, isoquinolinyl, chromonyl, coumarinyl, indolyl, indolizinyl, benzo[b]furanyl, benzo[b]thiophenyl, indazolyl, purinyl, 4H-quinolizinyl, isoquinolyl, quinolyl, phthalazinyl, naphthyridinyl, carbazolyl, 13-carbolinyl, and the like.

The term "neutral ligand" refers to an uncharged substituent, which is able to form a coordinate bond with a metal centre (ruthenium atom). Examples of such ligands may be: amines, phosphines and their oxides, alkyl and aryl phosphites and phosphates, arsines and their oxides, ethers, alkyl and aryl sulphides, coordinated hydrocarbons, alkyl and aryl halides.

The term "indenylidene" refers to an unsaturated hydrocarbon substituent with an indene (benzocyclopentadiene) backbone linked via a double bond to a metal atom.

The term "heteroindenylidene" refers to an indenylidene substituent, defined above, wherein at least one carbon atom was replaced with heteroatom from a group including nitrogen, oxygen, sulphur.

The term "anionic ligand" refers to a substituent, which is able to form a coordinate bond with a metal centre (ruthenium atom) having a charge which is able to partially or totally compensate the charge of the metal centre. Examples of such ligands may be fluorine, chloride, bromide, iodide, cyanide, cyanate, and thiocyanate anions, carboxylic acid anions, alcohol anions, phenol anions, thiol and thiophenol anions, anions of hydrocarbons with a delocalised charge (e.g. cyclopentadiene), anions of (organo)sulphuric and (organo)phosphoric acids and esters thereof (such as e.g. anions of alkylsulphonic and arylsulphonic acids, anions of alkylphosphoric and arylophosphoric acids, anions of sulphuric acid alkyl and aryl esters, anions of phosphoric acid alkyl and aryl esters, anions of alkylphosphoric and arylphosphoric acid alkyl and aryl esters). Optionally, anionic ligand may have $L^1$, $L^2$ and $L^3$ group, linked in the same way as catechol anion, acetylacetone anion, and salicylaldehyde anion. Anionic ligands ($X^1$, $X^2$) and neutral ligands ($L^1$, $L^2$, $L^3$) can be combined together to form polydentate ligands, for example bidentate ligand ($X^1$-$X^2$), tridentate ligand ($X^1$-$X^2$-$L^1$), tetradentate ligand ($X^1$-$X^2$-$L^1$-$L^2$), bidentate ligand ($X^1$-$L^1$), tridentate ligand ($X^1$-$L^1$-L2), tetradentate ligand ($X^1$-$L^1$-$L^2$-$L^3$), bidentate ligand ($L^1$-$L^2$), tridentate ligand ($L^1$-$L^2$-$L^3$). Examples of such ligands are: catechol anion, acetylacetone anion, and salicylaldehyde anion.

The term "heteroatom" means an atom selected from a group of oxygen, sulphur, nitrogen, phosphorus, and others.

The term "chlorinated solvent" means a solvent containing in its structure at least one atom of fluorine, chlorine, bromine, or iodine; more preferably more than one. Examples of such solvents are dichloromethane, chloroform, tetrachloromethane (carbon tetrachloride), 1,2-dichloroethane, chlorobenzene, perfluorobenzene, perfluorotoluene, freons, and others.

The term "nonpolar solvent" means a solvent characterised by a zero or very small dipole moment. Examples of such solvents are pentane, hexane, octane, nonane, decane, benzene, toluene, tetrahydrofuran (THF) and its derivatives, diethyl ether, dichloromethane, ethyl acetate, chloroform, and others.

The term "DEDAM" means diethyl diallylmalonate, used as a model diene in RCM reactions comparing activities of available precatalysts and catalysts for olefin metathesis reactions.

The term "GC" means gas chromatography.

The term "HPLC" means high pressure liquid chromatography, and solvents designated as solvents for "HPLC" are solvents of suitable purity for HPLC analysis.

The term "NMR" means nuclear magnetic resonance.

The term "NHC" means N-heterocyclic carbene.

The term "TLC" means thin layer chromatography.

The term "alkenyne" means a compound having in its structure a double and triple bond (en-yne).

The term "precatalyst" means, in the case of ruthenium complexes, a 16-electrone chemical compound, which after one ligand dissociation or molecular reorganisation step is converted into a proper 14-electron olefin metathesis catalyst, which takes an active part in the catalytic cycle.

Ruthenium complex compounds of the present invention are prepared by reactions shown on the following general reaction scheme, Scheme 1 and 2.

Scheme 1 shows a general course of reactions in the individual steps of the method of preparation complex compounds represented by the Formula 1 according to the invention. First step is obtaining CAAC carbene in a deprotonation reaction of the CAAC salt using a suitable base. The most preferable bases are hexamethyldisilazane salts [metal bis(trimethylsilyl)amides] represented by the Formula MHMDS, wherein M is an alkali metal, such as potassium or lithium. Process of deprotonation or contacting together suitable reagents could conducted in many polar or nonpolar solvents. Preferably toluene is used as a solvent. In the following step, the CAAC carbene formed is contacted with first generation ruthenium complex containing in its structure two phosphine-type ligands.

It has been shown, that the main product of this reaction is a second generation complex containing two CAAC ligands. In the TLC analysis one could observe also small amounts of the other second generation complex, which most probably contains one CAAC ligand and one phosphine ligand, Scheme 1 and 2.

The last process step is the addition of benzylidene ligand 4 to the mixture of unknown proportion of major and minor intermediates 5, in the presence of phosphine ligand scavenger and/or CAAC ligand scavenger (Scheme 2). Scheme 2 shows only the proposed course of 16-electron ruthenium complex formation without detailed analysis of the metathesis process mechanism. Preferably, as a benzylidene ligand 2-isopropoxypropenylbenzene derivatives are used. It appeared that the preferable phosphine and/or CAAC ligand scavengers were copper(I) salts, including CuCl. Reactions shown in the Scheme 1 and 2 were conducted in a single reaction vessel without isolation of the intermediates (Embodiments 1-XIV).

To confirm that the intermediate compound 5 takes part actively in the preparation process of the precatalysts represented by the Formula 1, the previous one-pot type process was divided into two independent reaction parts, (a) and (b) in the Scheme 3. Ruthenium complexes represented by the general formula 5 were isolated and characterised with the NMR and MS analysis, confirming lack of phosphine ligand in the structure and presence of the two CAAC ligands. It has been shown, that compounds represented by the structure 5 in the reaction with benzylidene ligand 4 in the presence of CAAC ligand scavenger provide compounds represented by the Formula 1. Reactions for individual steps were shown in the Scheme 3 (part (a) in Embodiments XV, XVI and XVIII and part (b) in Embodiments XVII and XIX). Moreover, the inventors decided to check, whether intermediate compounds represented by the general formula 5 are active precatalysts in the olefin metathesis, what was shown in the Example XXII.

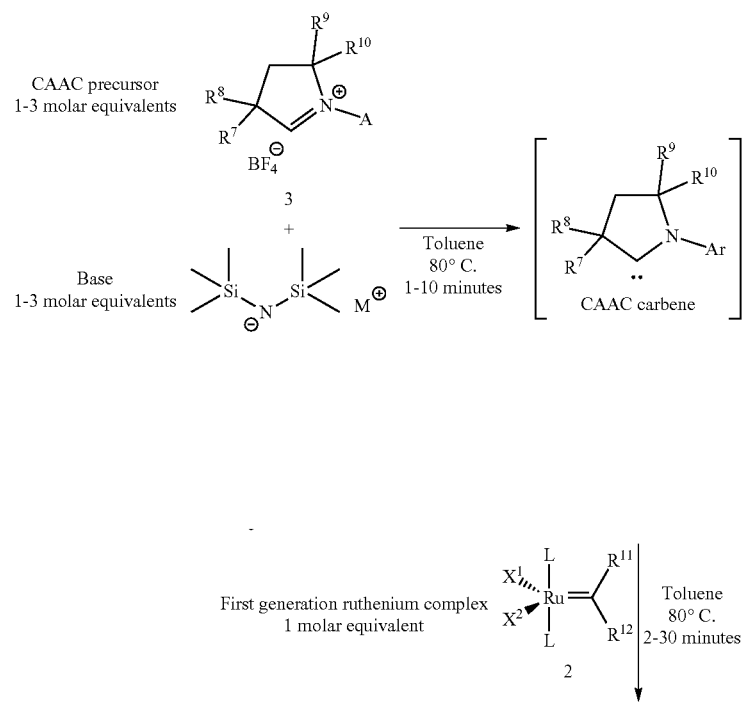

Scheme 1

-continued
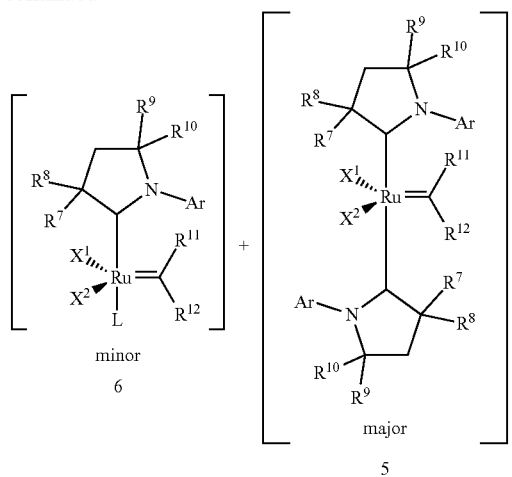
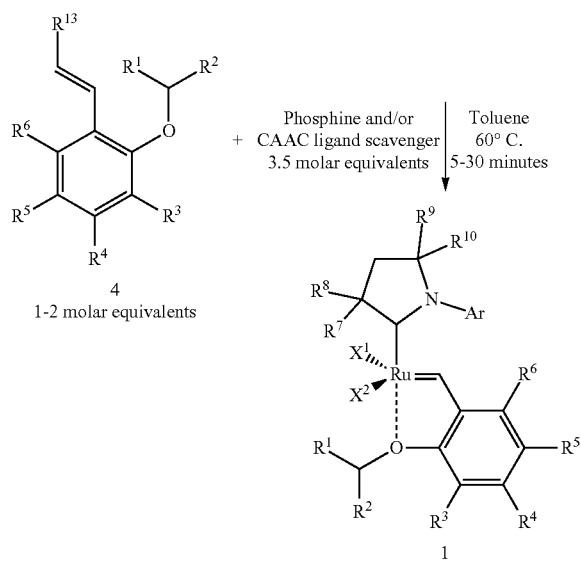
Scheme 2
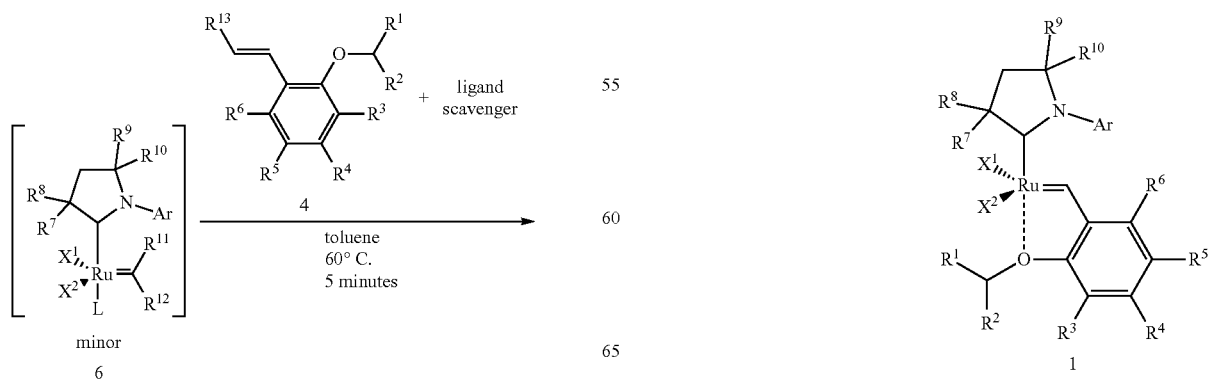
-continued

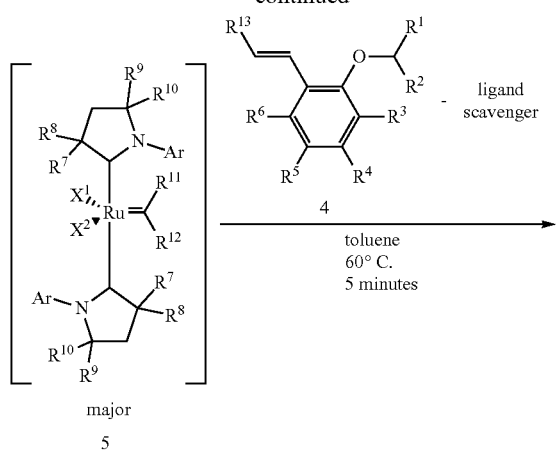

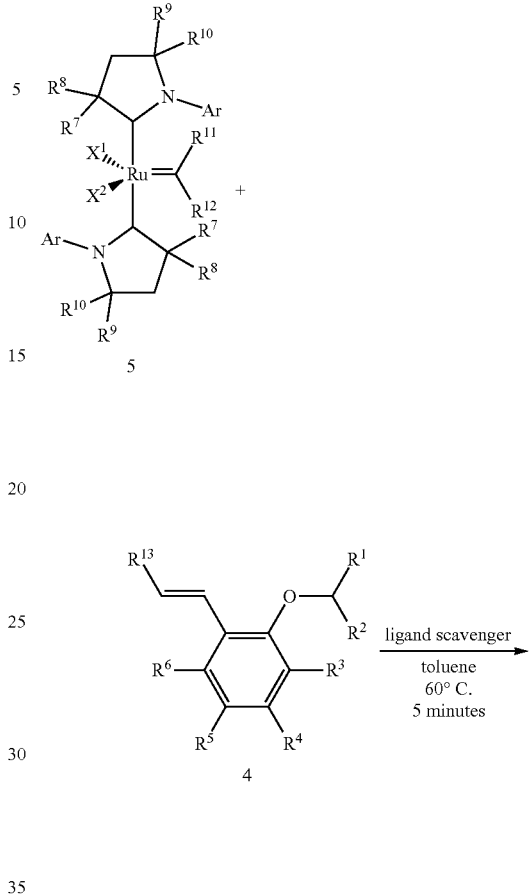

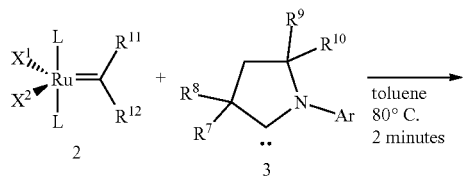

Scheme 3

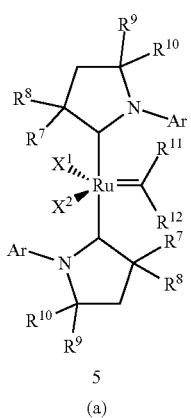

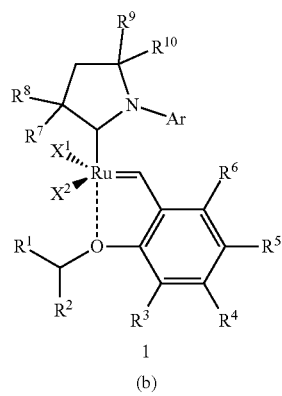

In the examples described below the preparation methods and use of the new ruthenium complexes of the invention were illustrated. The examples shown below are provided for the better understanding of the invention and they are not intended to limit its scope in any way. Examples of the catalyst preparation of the invention confirm higher process yields and more preferable ruthenium complex preparation parameters on the industrial scale. Comparative Examples with known complexes used confirm that complexes of the invention show different catalytic properties.

EMBODIMENTS OF THE INVENTION

Example I

Preparation method of precatalyst 1a

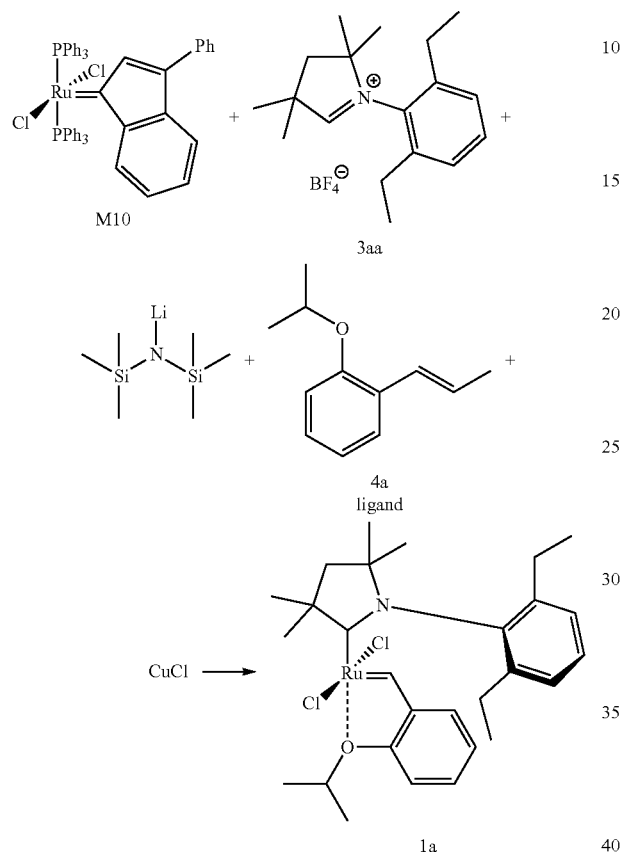

Example II

Preparation method of precatalyst 1a; attempt with a greater amount of CAAC salt 3aa—here 3 molar equivalents.

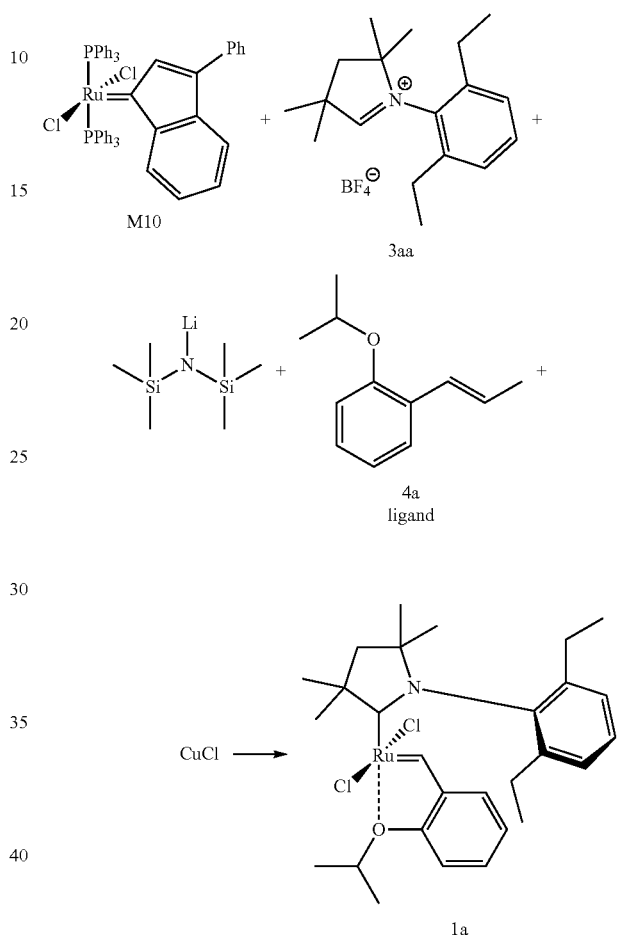

To salt 3aa (1.73 g, 5.0 mmol, 2 molar equivalents) dry deoxygenated toluene (20 ml) was added in argon atmosphere. The mixture was heated to 80° C. and solution of LiHMDS in toluene (1 M, 5.0 ml, 5.0 mmol, 2 molar equivalents) was added. After 1 minute solid complex M10 (2.22 g, 2.5 mmol, 1 molar equivalent) was added. After 2 minutes the mixture was cooled down to 60° C. Benzylidene ligand 4a (0.529 g, 3.0 mmol, 1.2 molar equivalents) and CuCl (0.866 g, 8.75 mmol, 3.5 molar equivalents) were added. Reaction mixture was stirred for 5 minutes at 60° C. and cooled down to the room temperature. The crude product was isolated by column chromatography on silica gel (eluent: toluene). Green fraction was collected and concentrated to dryness. The residue was dissolved in ethyl acetate and filtrated. The solvent was evaporated, the residue was washed with isopropanol and dried under high vacuum giving green crystalline solid—precatalyst 1a (0.584 g, 40%).

$^1$H NMR ($C_6D_6$, 500 MHz): δ=16.41 (s, 1H), 7.33-7.28 (m, 1H), 7.22-7.18 (m, 2H), 7.16-7.11 (m, 1H), 7.01 (dd, J=7.6; 1.6 Hz, 1H), 6.64 (td, J=7.4; 0.8 Hz, 1H), 6.46-6.42 (m, 1H), 4.67 (septet, J=6.1 Hz, 1H), 2.87-2.78 (m, 2H), 2.45-2.35 (m, 2H), 2.23 (s, 6H), 1.77 (s, 2H), 1.70 (d, J=6.1 Hz, 6H), 0.97-0.92 (m, 12H) ppm.

To salt 3aa (1.40 g, 4.05 mmol, 3 molar equivalents) dry deoxygenated toluene (10 ml) was added in argon atmosphere. The mixture was heated to 80° C. and solution of LiHMDS in toluene (1 M, 4.05 ml, 4.05 mmol, 3 molar equivalents) was added. After 1 minute solid complex M10 (1.20 g, 1.35 mmol, 1 molar equivalent) was added. After 2 minutes the mixture was cooled down to 60° C. Ligand 4a (0.286 g, 1.62 mmol, 1.2 molar equivalents) and CuCl (0.601 g, 6.08 mmol, 4.5 molar equivalents) were added. Reaction mixture was stirred for 5 minutes at 60° C. and cooled down to the room temperature. The crude product was isolated by column chromatography on silica gel (eluent: toluene). Green fraction was collected and concentrated to dryness. The residue was dissolved in ethyl acetate and filtrated. The solvent was evaporated, the residue was washed with isopropanol and dried under high vacuum giving green crystalline solid—precatalyst 1a (0.408 g, 52%). Comparison with Example I.

Example III

Preparation method of Hoveyda-type precatalyst 1a using other first generation precursor, here M1 (Umicore M1™).

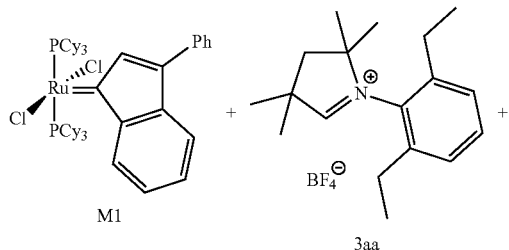

3aa

Example IV

Preparation method of precatalyst 1a using other first generation precursor, here Gru-1.

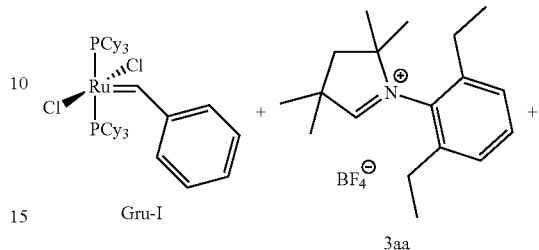

3aa

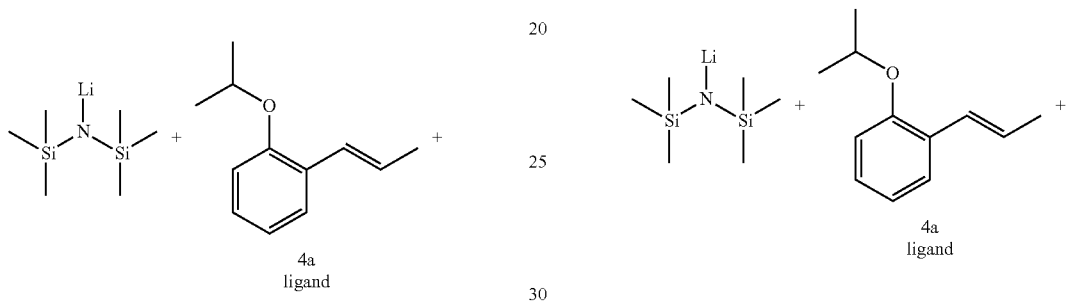

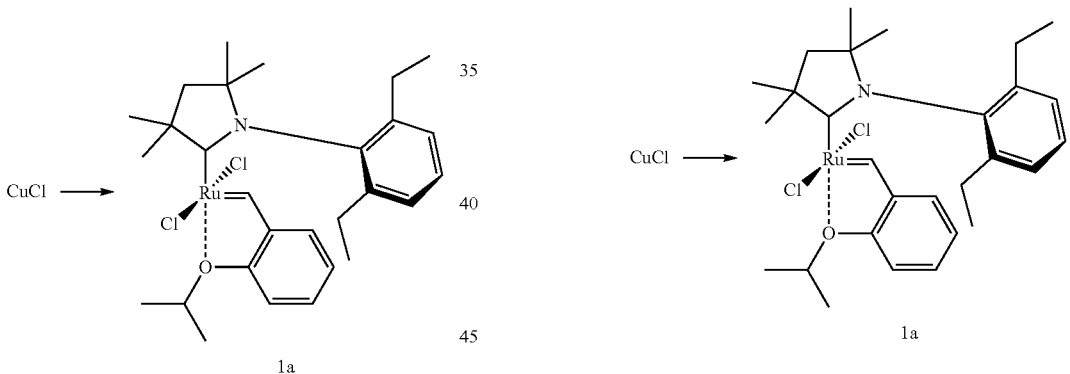

To salt 3aa (1.06 g, 3.07 mmol, 2 molar equivalents) dry deoxygenated toluene (12 ml) was added in argon atmosphere. The mixture was heated to 80'C and solution of LiHMDS in toluene (1 M, 3.07 ml, 3.07 mmol, 2 molar equivalents) was added. After 1 minute solid complex M1 (1.42 g, 1.53 mmol, 1 molar equivalent) was added. After 10 minutes the mixture was cooled down to 60'C. Benzylidene ligand 4a (0.325 g, 1.84 mmol, 1.2 molar equivalents) and CuCl (0.532 g, 5.37 mmol, 3.5 molar equivalents) were added. Reaction mixture was stirred for 10 minutes at 60'C and cooled down to the room temperature. The crude product was isolated by column chromatography on silica gel (eluent: toluene). Green fraction was collected and concentrated to dryness. The residue was dissolved in ethyl acetate and filtrated. The solvent was evaporated, the residue was washed with isopropanol and dried under high vacuum giving green crystalline solid -precatalyst 1a (0.520 g, 58%). Comparison with the Example I.

To salt 3aa (1.04 g, 3.0 mmol, 2 molar equivalents) dry deoxygenated toluene (12 ml) was added in argon atmosphere. The mixture was heated to 80'C and solution of LiHMDS in toluene (1 M, 3.0 ml, 3.0 mmol, 2 molar equivalents) was added. After 1 minute solid complex Gru-1 (1.23 g, 1.5 mmol, 1 molar equivalent) was added. After 30 minutes the mixture was cooled down to 60'C. Benzylidene ligand 4a (0.317 g, 1.8 mmol, 1.2 molar equivalents) and CuCl (0.520 g, 5.25 mmol, 3.5 molar equivalents) were added. Reaction mixture was stirred for 10 minutes at 60'C and cooled down to the room temperature. The crude product was isolated by column chromatography on silica gel (eluent: toluene). Green fraction was collected and concentrated to dryness. The residue was dissolved in ethyl acetate and filtrated. The solvent was evaporated, the residue was washed with isopropanol and dried under high vacuum giving green crystalline solid—precatalyst 1a (0.409 g, 47%). Comparison with Example I.

Example V

Preparation method of precatalyst 1b containing nitro group-activated benzylidene

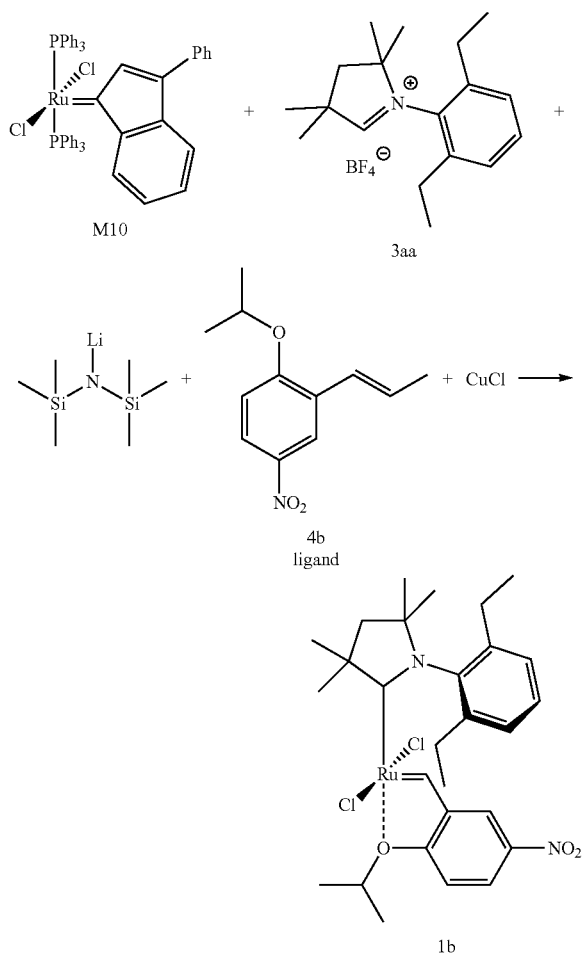

1b

To salt 3aa (3.45 g, 10.0 mmol, 2 molar equivalents) dry deoxygenated toluene (40 ml) was added in argon atmosphere. The mixture was heated to 80° C. and solution of LiHMDS in toluene (1 M, 10.0 ml, 10.0 mmol, 2 molar equivalents) was added. After 1 minute solid complex M10 (4.43 g, 5.0 mmol, 1 molar equivalent) was added. After 2 minutes the mixture was cooled down to 60° C. Benzylidene ligand 4b (1.33 g, 6.0 mmol, 1.2 molar equivalents) and CuCl (1.73 g, 17.5 mmol, 3.5 molar equivalents) were added. Reaction mixture was stirred for 5 minutes at 60° C. and cooled down to the room temperature. The crude product was isolated by column chromatography on silica gel (eluent: toluene). Green fraction was collected and concentrated to dryness. The residue was dissolved in ethyl acetate and filtrated. The solvent was evaporated, the residue was washed with isopropanol and dried under high vacuum giving green crystalline solid -precatalyst 1 b (1.57 g, 50%).

$^1$H NMR (CD$_2$Cl$_2$, 500 MHz): δ=16.29 (s, 1H), 8.46 (dd, J=9.1; 2.7 Hz, 1H), 7.72-7.65 (m, 2H), 7.51 (d, J=7.7 Hz, 2H), 7.08 (d, J=8.7 Hz, 1H), 5.26 (septet, J=6.1 Hz, 1H), 2.61-2.49 (m, 4H), 2.21 (s, 2H), 2.07 (s, 6H), 1.77 (d, J=6.2 Hz, 6H), 1.33 (s, 6H), 0.91 (t, J=7.4 Hz, 6H) ppm.

$^{13}$C NMR (CD$_2$Cl$_2$, 125 MHz): δ=290.4, 263.8, 165.6, 157.1, 143.7, 143.4, 138.8, 129.9, 127.7, 125.7, 118.3, 113.7, 79.4, 78.2, 56.5, 52.3, 29.9, 28.9, 25.3, 22.4, 14.9 ppm.

HRMS-ESI calculated for C$_{28}$H$_{39}$N$_2$O$_3$Ru [M−2Cl+H]+: 553.2006; found: 553.2004.

Elemental analysis: calculated for C$_{28}$H$_{39}$N$_2$Cl$_2$O$_3$Ru:
C 54.02; H 6.15; N 4.50; Cl 11.39; found: C 54.18; H 6.09; N 4.42; Cl 11.20.

Example VI

Preparation method of precatalyst 1c containing hydroxamic group-activated benzylidene

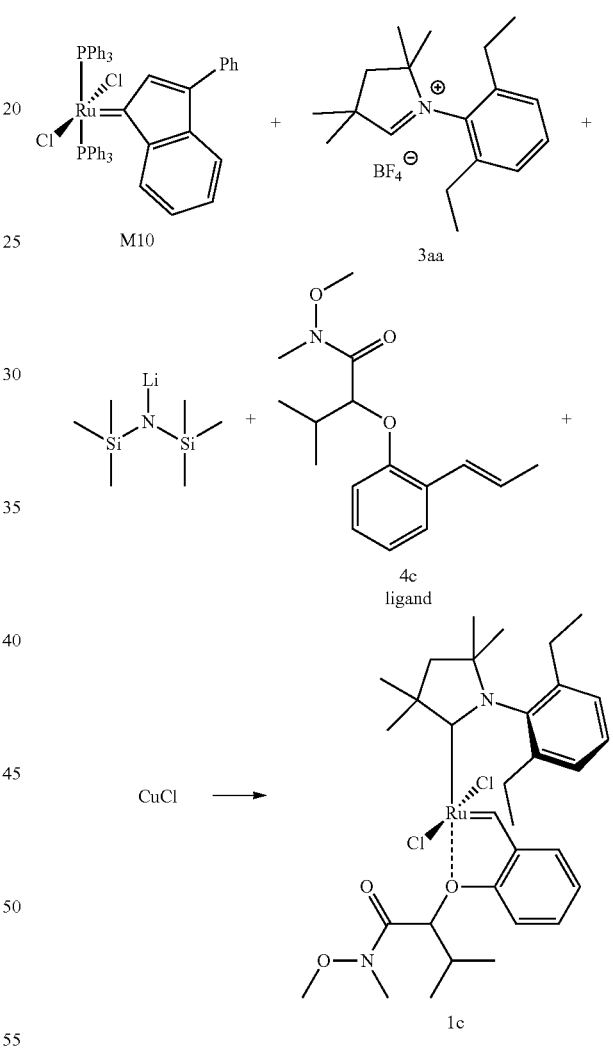

1c

To salt 3aa (3.45 g, 10.0 mmol, 2 molar equivalents) dry deoxygenated toluene (40 ml) was added in argon atmosphere. The mixture was heated to 80° C. and solution of LiHMDS in toluene (1 M, 10.0 ml, 10.0 mmol, 2 molar equivalents) was added. After 1 minute solid complex M10 (4.43 g, 5.0 mmol, 1 molar equivalent) was added. After 2 minutes the mixture was cooled down to 60° C. Benzylidene ligand 4c (1.66 g, 6.0 mmol, 1.2 molar equivalents) and CuCl (1.73 g, 17.5 mmol, 3.5 molar equivalents) were added. Reaction mixture was stirred for 5 minutes at 60° C. and cooled down to the room temperature. The crude product was isolated by column chromatography on silica gel (eluent: toluene→ethyl acetate/cyclohexane 3:7 v/v). Green fraction was collected and concentrated to dryness. The residue was dissolved in ethyl acetate and filtrated. The solvent was evaporated and the residue was dissolved in a minimal amount of methylene chloride and was added n-heptane. Methylene chloride was removed slowly on the evaporator, the resulting crystals were filtered off, washed with a small amount of n-heptane and dried under high vacuum giving green crystalline solid—precatalyst 1c (1.05 g, 31%).

$^1$H NMR (CD$_2$Cl$_2$. 500 MHz): δ=16.46 (s, 1H), 7.62-7.55 (m, 2H), 7.50-7.46 (m, 1H), 7.43-7.39 (m, 1H), 7.03 (d, J=8.3 Hz, 1H), 6.97 (t, J=7.4 Hz, 1H), 6.92-6.89 (m, 1H), 5.50 (d, J=7.5 Hz, 1H), 3.75 (s, 3H), 3.39 (s, 3H), 2.90 (dq, J=15.0; 7.4 Hz, 1H), 2.66 (dq, J=15.0; 7.4 Hz, 1H), 2.58 (dq, J=14.0; 7.0 Hz, 1H), 2.32 (q, J=7.5 Hz, 2H), 2.28 (s, 3H), 2.25-2.21 (m, 1H), 2.15-2.11 (m, 1H), 1.94 (s, 3H), 1.31 (s, 3H), 1.22 (s, 3H), 1.11 (t, J=7.4 Hz, 3H), 0.98 (dd, J=9.2; 6.9 Hz, 6H), 0.79 (t, J=7.4 Hz, 3H) ppm.

$^{13}$C NMR (CD$_2$Cl$_2$. 125 MHz): δ=305.2, 267.2, 170.0, 154.3, 146.0, 143.8, 143.4, 140.2, 130.0, 129.0, 127.2, 126.9, 123.6, 123.4, 113.2, 79.9, 79.8, 78.2, 62.3, 62.2, 56.3, 53.4, 32.6, 32.5, 31.3, 31.2, 30.9, 29.4, 29.3, 25.6, 25.5, 25.4, 25.1, 25.0, 19.9, 18.2, 14.8, 14.7, 14.6 ppm.

HRMS-ESI calculated for C$_{33}$H$_{49}$N$_2$O$_4$Ru [M−2Cl+CH$_3$O]+: 639.2740; found: 639.2718.

Elemental analysis: calculated for C$_{32}$H$_{46}$N$_2$Cl$_2$O$_3$Ru:

C 56.63; H 6.83; N 4.13; Cl 10.45; found: C 56.63; H 6.73; N 4.01; Cl 10.25.

Example VII

Preparation method of precatalyst 1d

To salt 3ab (1.73 g, 5.0 mmol, 2 molar equivalents) dry deoxygenated toluene (20 ml) was added in argon atmosphere. The mixture was heated to 80'C and solution of LiHMDS in toluene (1 M, 5.0 ml, 5.0 mmol, 2 molar equivalents) was added. After 1 minute solid complex M10 (2.22 g, 2.5 mmol, 1 molar equivalent) was added. After 2 minutes the mixture was cooled down to 60'C. Benzylidene ligand 4a (0.529 g, 3.0 mmol, 1.2 molar equivalents) and CuCl (0.866 g, 8.75 mmol, 3.5 molar equivalents) were added. Reaction mixture was stirred for 5 minutes at 60'C and cooled down to the room temperature. The crude product was isolated by column chromatography on silica gel (eluent: toluene). Green fraction was collected and concentrated to dryness. The residue was dissolved in ethyl acetate and filtrated. The solvent was evaporated, the residue was washed with isopropanol and dried under high vacuum giving green crystalline solid—precatalyst 7d (0.688 g, 47%).

$^1$H NMR (CD$_2$Cl$_2$. 500 MHz): δ=16.20 (s, 1H), 7.60-7.53 (m, 2H), 7.50-7.47 (m, 1H), 7.29 (ddd, J=7.4; 1.7; 0.8 Hz, 1H), 6.97 (d, J=8.3 Hz, 1H), 6.92-6.85 (m, 2H), 5.16 (sept, J=6.1 Hz, 1H), 2.98 (sept, J=6.6 Hz, 1H), 2.24 (s, 3H), 2.23-2.16 (m, 2H), 2.13 (s, 3H), 2.02 (s, 3H), 1.75 (d, J=6.1 Hz, 3H), 1.71 (d, J=6.1 Hz, 3H), 1.40 (s, 3H), 1.36 (s, 3H), 1.28 (d, J=6.7 Hz, 3H), 0.67 (d, J=6.5 Hz, 3H) ppm.

Example VIII

Preparation method of precatalyst 7d; attempt with a reduced amount of CAAC salt 3ab.

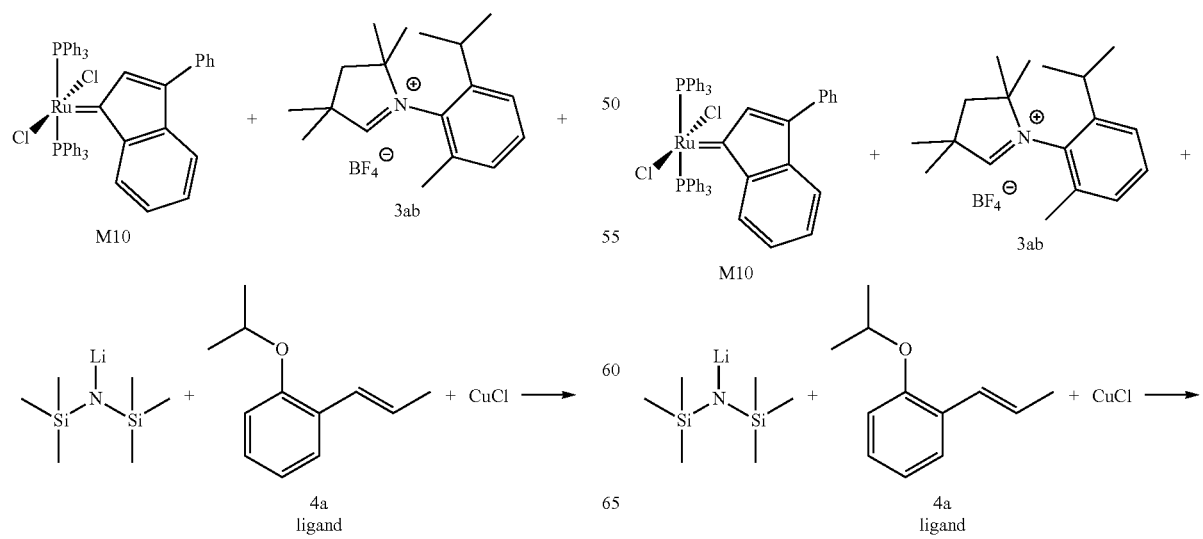

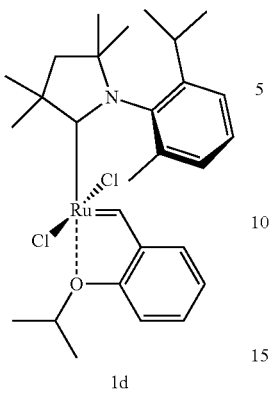

1d

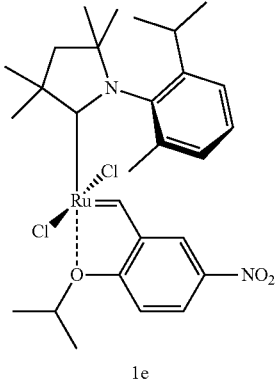

1e

To salt 3ab (1.08 g, 3.13 mmol, 1.25 molar equivalents) dry deoxygenated toluene (22 ml) was added in argon atmosphere. The mixture was heated to 80'C and solution of LiHMDS in toluene (1 M, 3.0 ml, 3.0 mmol, 1.2 molar equivalents) was added. After 1 minute solid complex M10 (2.22 g, 2.5 mmol, 1 molar equivalent) was added. After 2 minutes the mixture was cooled down to 60'C. Benzylidene ligand 4a (0.529 g, 3.0 mmol, 1.2 molar equivalents) and CuCl (0.619 g, 6.25 mmol, 2.5 molar equivalents) were added. Reaction mixture was stirred for 5 minutes at 60'C and cooled down to the room temperature. The crude product was isolated by column chromatography on silica gel (eluent: toluene). Green fraction was collected and concentrated to dryness. The residue was dissolved in ethyl acetate and filtrated. The solvent was evaporated, the residue was washed with isopropanol and dried under high vacuum giving green crystalline solid—precatalyst 1d (0.596 g, 41%). Comparison with Example VI.

Example IX

Preparation method of precatalyst 1e containing nitro group-activated benzylidene

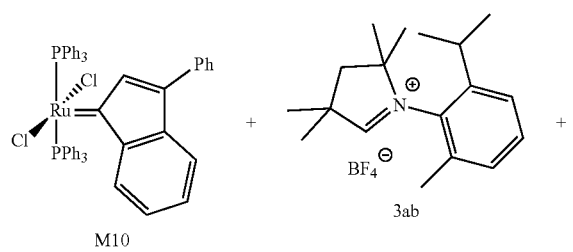

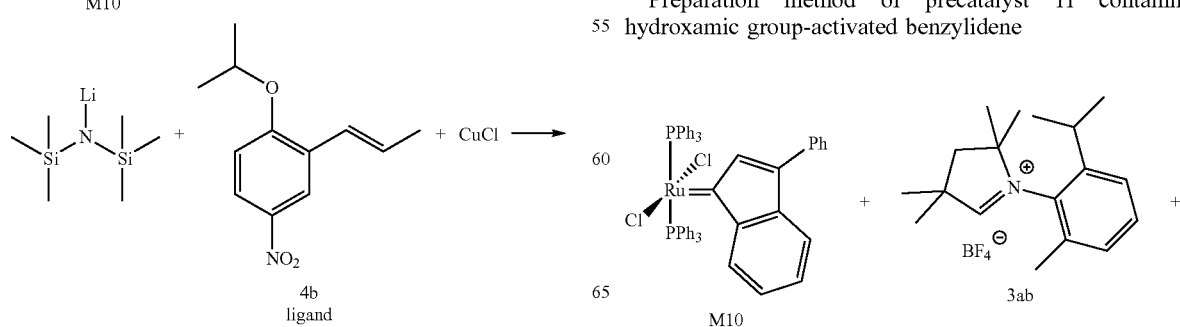

To salt 3ab (1.73 g, 5.0 mmol, 2 molar equivalents) dry deoxygenated toluene (20 ml) was added in argon atmosphere. The mixture was heated to 80° C. and solution of LiHMDS in toluene (1 M, 5.0 ml, 5.0 mmol, 2 molar equivalents) was added. After 1 minute solid complex M10 (2.22 g, 2.5 mmol, 1 molar equivalent) was added. After 2 minutes the mixture was cooled down to 60° C. Benzylidene ligand 4b (0.664 g, 3.0 mmol, 1.2 molar equivalents) and CuCl (0.866 g, 8.75 mmol, 3.5 molar equivalents) were added. Reaction mixture was stirred for 5 minutes at 60° C. and cooled down to the room temperature. The crude product was isolated by column chromatography on silica gel (eluent: toluene). Green fraction was collected and concentrated to dryness. The residue was dissolved in ethyl acetate and filtrated. The solvent was evaporated, the residue was washed with isopropanol and dried under high vacuum giving green crystalline solid—precatalyst 1e (0.663 g, 42%).

$^1$H NMR (CD$_2$Cl$_2$. 500 MHz): δ=16.19 (s, 1H), 8.45 (dd, J=9.1; 2.7 Hz, 1H), 7.70 (d, J=2.7 Hz, 1H), 7.65 (t, J=7.7 Hz, 1H), 7.55 (dd, J=8.0; 1.5 Hz, 1H), 7.35 (ddd, J=7.5; 1.6; 0.7 Hz, 1H), 7.08 (d, J=8.9 Hz, 1H), 5.26 (sept, J=6.2 Hz, 1H), 2.97 (sept, J=6.7 Hz, 1H), 2.26-2.19 (m, SH), 2.13 (s, 3H), 2.03 (s, 3H), 1.77 (dd, J=16.1; 6.1 Hz, 6H), 1.43 (s, 3H), 1.38 (s, 3H), 1.30 (d, J=6.6 Hz, 3H), 0.68 (d, J=6.5 Hz, 3H) ppm.

$^{13}$C NMR (CD$_2$Cl$_2$. 125 MHz): δ=290.2, 264.6, 157.2, 149.1, 143.5, 143.4, 138.5, 138.4, 130.4, 130.0, 126.5, 125.8, 118.4, 113.7, 79.4, 78.2, 56.6, 52.3, 29.9, 29.7, 29.6, 29.1, 28.9, 26.3, 24.3, 22.4, 22.3, 21.8 ppm.

HRMS-ESI calculated for C$_{28}$H$_{38}$ClN$_2$O$_3$Ru [M−Cl]+: 587.1613; found: 587.1636.

Elemental analysis: calculated for C2BH3aN2Cl2O3Ru: C 54.02; H 6.15; N 4.50; Cl 11.39; found: C 54.19; H 6.18; N 4.37; Cl 11.21.

Example X

Preparation method of precatalyst 1f containing hydroxamic group-activated benzylidene

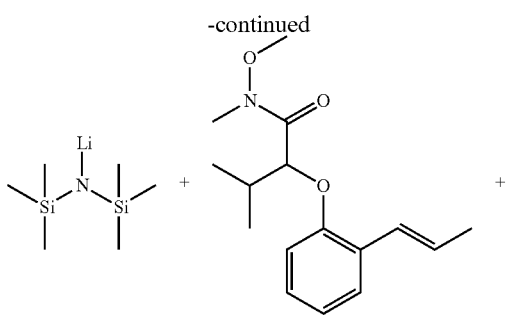

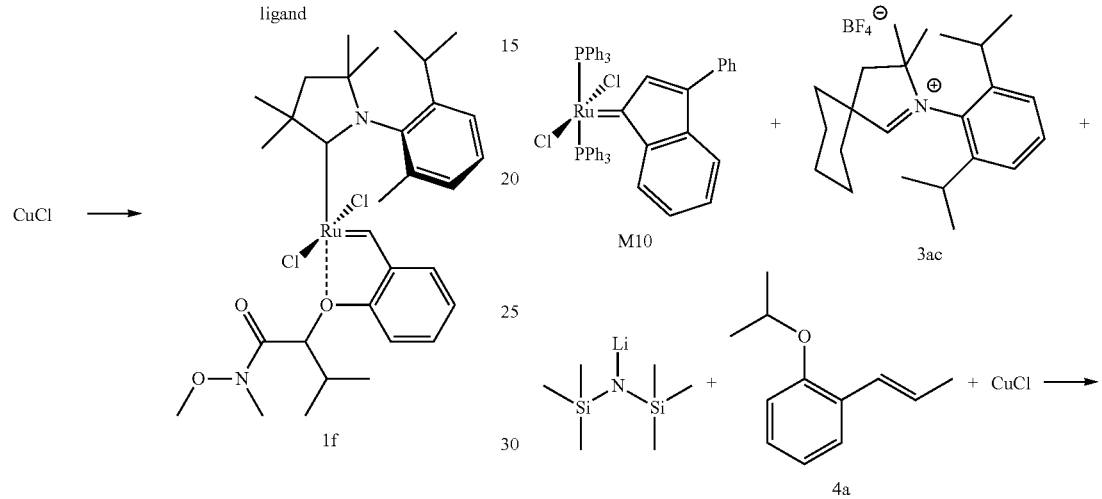

To salt 3ab (1.73 g, 5.0 mmol, 2 molar equivalents) dry deoxygenated toluene (20 ml) was added in argon atmosphere. The mixture was heated to 80° C. and solution of LiHMDS in toluene (1 M, 5.0 ml, 5.0 mmol, 2 molar equivalents) was added. After 1 minute solid complex M10 (2.22 g, 2.5 mmol, 1 molar equivalent) was added. After 2 minutes the mixture was cooled down to 60° C. Benzylidene ligand 4c (0.832 g, 3.0 mmol, 1.2 molar equivalents) and CuCl (0.866 g, 8.75 mmol, 3.5 molar equivalents) were added. Reaction mixture was stirred for 5 minutes at 60° C. and cooled down to the room temperature. The crude product was isolated by column chromatography on silica gel (eluent: toluene→ethyl acetate/cyclohexane 3:7 v/v). Green fraction was collected and concentrated to dryness. The residue was dissolved in ethyl acetate and filtrated. The solvent was evaporated and the residue was dissolved in a minimal amount of methylene chloride and n-heptane was added. Methylene chloride was removed slowly on the evaporator, the resulting crystals were filtered off, washed with a small amount of n-heptane and dried under high vacuum giving green crystalline solid—precatalyst 1f (0.390 g, 23%). A mixture of isomers A:B=1.8:1.

Due to a very complex $^1$H NMR spectrum only the characteristic benzylidene proton shifts were given: isomer A: singlet 16.42 ppm, isomer B: singlet 16.45 ppm (CD2Cl2).

$^{13}$C NMR (CD$_2$Cl$_2$1 125 MHz): δ=304.0 (A), 303.5 (B), 268.1 (B), 267.9 (A), 170.0 (A), 169.4 (B), 154.4 (A), 154.3 (B), 149.0 (B), 148.6 (A), 145.4 (B), 145.3 (A), 139.9 (B), 139.8 (A), 138.8 (A), 138.5 (B), 130.2 (A), 130.16 (B), 130.0 (A), 129.9 (B), 129.2 (B), 129.2 (A), 126.2 (B), 125.9 (A), 123.8 (B), 123.8 (A), 123.7 (B), 123.5 (A), 113.3 (B), 113.1 (A), 79.8 (B), 79.6 (A), 78.1 (B), 78.0 (A), 62.4 (A), 62.2 (B), 56.4 (B), 56.3 (A), 53.7 (A), 53.5 (B), 32.6 (A), 32.4 (B), 31.3 (A), 31.1 (B), 30.8 (B), 30.8 (B) 30.7 (A), 30.6 (A), 29.0 (B), 28.9 (A), 28.7 (B), 28.6 (A), 26.9, 24.9 (A), 24.8 (B), 22.3 (A), 21.7 (B), 20.0 (B), 19.9 (A), 18.2 ppm.

HRMS-ESI calculated for $C_{33}H_{49}N_2O_4Ru$ [M−2Cl+CH3O]+: 639.2740; found: 639.2756.

Elemental analysis: calculated for $C_{32}H_{46}N_2Cl_2O_3Ru$: C 56.63; H 6.83; N 4.13; Cl 10.45; found: C 56.69; H 6.80; N 4.07; Cl 10.41.

Example XI

Preparation method of precatalyst 1g

To salt 3ac (0.413 g, 1.0 mmol, 2 molar equivalents) dry deoxygenated toluene (4 ml) was added in argon atmosphere. The mixture was heated to 80° C. and solution of LiHMDS in toluene (1 M, 1.0 ml, 1.0 mmol, 2 molar equivalents) was added. After 1 minute solid complex M10 (0.443 g, 0.5 mmol, 1 molar equivalent) was added. After 2 minutes the mixture was cooled down to 60° C. Benzylidene ligand 4a (0.106 g, 0.6 mmol, 1.2 molar equivalents) and CuCl (0.173 g, 1.75 mmol, 3.5 molar equivalents) were added. Reaction mixture was stirred for 25 minutes at 60° C. and cooled down to the room temperature. The crude product was isolated by column chromatography on silica gel (eluent: toluene). Green fraction was collected and concentrated to dryness. The residue was dissolved in ethyl acetate and filtrated. The solvent was evaporated, the residue was washed with isopropanol and dried under high vacuum giving green crystalline solid—precatalyst 1g (0.118 g, 37%).

$^1$H NMR (C$_6$D$_6$. 500 MHz): δ=16.56 (s, 1H), 7.38-7.35 (m, 1H), 7.28-7.25 (m, 2H), 7.14-7.11 (m, 1H), 7.03-7.00 (m, 1H), 6.65 (t, J=7.4 Hz, 1H), 6.44 (d, J=8.3 Hz, 1H), 4.66 (sept, J=6.0 Hz, 1H), 3.77 (td, J=13.0; 3.4 Hz, 2H), 3.21 (sept, J=6.4 Hz, 2H), 2.50 (d, J=12.7 Hz, 2H), 1.93 (s, 2H), 1.90-1.85 (m, 2H), 1.74 (d, J=6.1 Hz, 6H), 1.70-1.60 (m, 2H), 1.43-1.34 (m, 2H), 1.16 (d, J=6.6 Hz, 6H), 1.00 (s, 6H), 0.93 (d, J=6.4 Hz, 6H) ppm.

Example XII

Preparation method of precatalyst 1g; attempt with other base to generate CAAC carbene—here KHMDS.

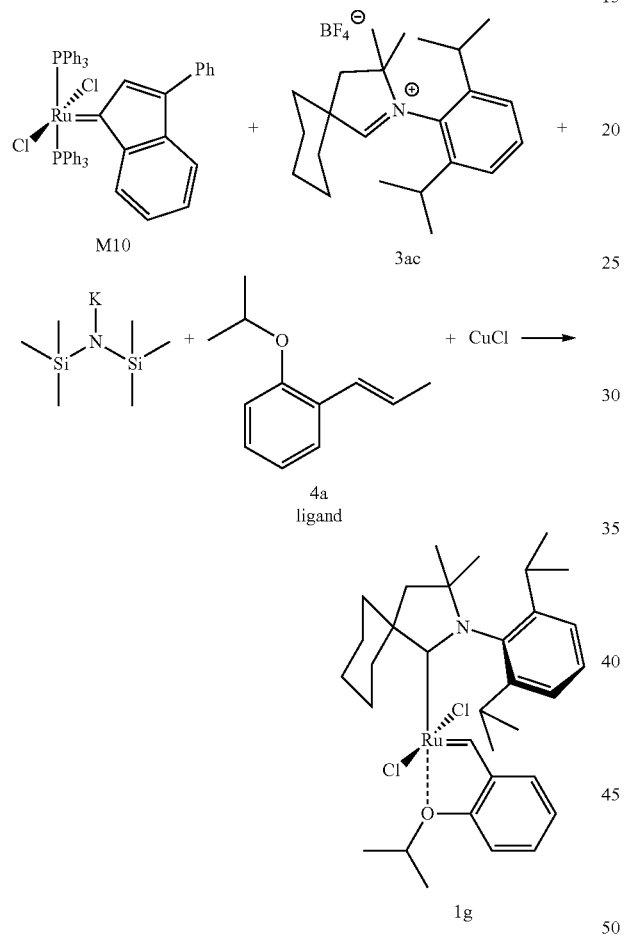

To salt 3ac (1.65 g, 4.0 mmol, 2 molar equivalents) dry deoxygenated toluene (12 ml) was added in argon atmosphere. The mixture was heated to 80° C. and solution of KHMDS in toluene (0.5M, 8.0 ml, 4.0 mmol, 2 molar equivalents) was added. After 1 minute solid complex M10 (1.77 g, 2.0 mmol, 1 molar equivalent) was added. After 2 minutes the mixture was cooled down to 60° C. Benzylidene ligand 4a (0.423 g, 2.4 mmol, 1.2 molar equivalents) and CuCl (0.693 g, 7.0 mmol, 3.5 molar equivalents) were added. Reaction mixture was stirred for 25 minutes at 60° C. and cooled down to the room temperature. The crude product was isolated by column chromatography on silica gel (eluent: toluene). Green fraction was collected and concentrated to dryness. The residue was dissolved in ethyl acetate and filtrated. The solvent was evaporated, the residue was washed with isopropanol and dried under high vacuum giving green crystalline solid—precatalyst 1g (0.580 g, 45%). Comparison with Example XI.

Example XIII

Preparation method of precatalyst 1 h containing nitro group-activated benzylidene

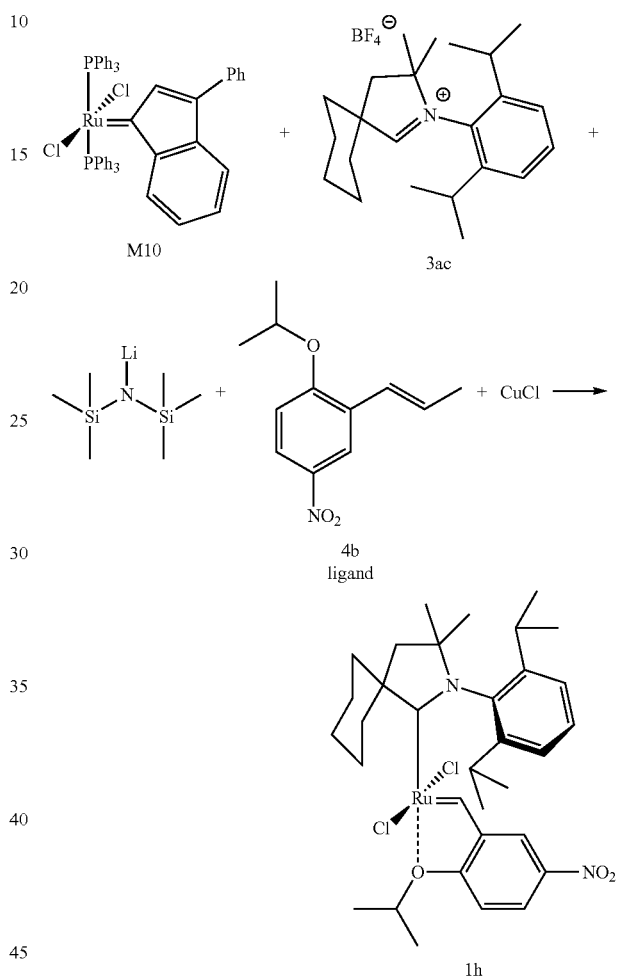

To salt 3ac (1.65 g, 4.0 mmol, 2 molar equivalents) dry deoxygenated toluene (16 ml) was added in argon atmosphere. The mixture was heated to 80° C. and solution of LiHMDS in toluene (1 M, 4.0 ml, 4.0 mmol, 2 molar equivalents) was added. After 1 minute solid complex M10 (1.77 g, 2.0 mmol, 1 molar equivalent) was added. After 2 minutes the mixture was cooled down to 60° C. Benzylidene ligand 4b (0.531 g, 2.4 mmol, 1.2 molar equivalents) and CuCl (0.693 g, 7.0 mmol, 3.5 molar equivalents) were added. Reaction mixture was stirred for 25 minutes at 60° C. and cooled down to the room temperature. The crude product was isolated by column chromatography on silica gel (eluent: toluene). Green fraction was collected and concentrated to dryness. The residue was dissolved in ethyl acetate and filtrated. The solvent was evaporated, the residue was washed with isopropanol and dried under high vacuum giving green crystalline solid—precatalyst 1 h (0.550 g, 40%).

$^1$H NMR (CD$_2$Cl$_2$. 500 MHz): δ=16.42 (s, 1H), 8.44 (dd, J=9.1; 2.7 Hz, 1H), 7.71 (t, J=7.8 Hz, 1H), 7.65 (d, J=2.7 Hz, 1H), 7.51 (d, J=7.8 Hz, 2H), 7.10-7.07 (m, 1H), 5.25 (sept, J=5.9 Hz, 1H), 3.30-3.21 (m, 2H), 2.96 (sept, J=6.6 Hz, 2H), 2.31 (s, 2H), 2.28-2.22 (m, 2H), 1.96-1.89 (m, 2H), 1.78 (d, J=6.1 Hz, 6H), 1.60-1.46 (m, 4H), 1.35 (s, 6H), 1.26 (d, J=6.6 Hz, 6H), 0.64 (d, J=6.4 Hz, 6H) ppm.

$^{13}$C NMR (CD$_2$Cl$_2$, 125 MHz): δ=288.9, 264.7, 157.5, 148.7, 143.3, 142.9, 136.7, 130.4, 126.5, 125.7, 118.4, 113.8, 79.0, 78.2, 62.8, 44.9, 35.3, 30.8, 28.9, 26.8, 26.1, 24.6, 23.6, 22.5 ppm.

HRMS-ESI calculated for C$_{33}$H$_{47}$N$_2$O$_3$Ru [M−2Cl+H]+: 621.2634; found: 621.2630.

Elemental analysis: calculated for C$_{33}$H$_{46}$N$_2$Cl$_2$O$_3$Ru:
C 57.38; H 6.71; N 4.06; Cl 10.27; found: C 57.27; H 6.58; N 4.18; Cl 10.12.

Example XIV

Preparation method of precatalyst 1 i containing hydroxamic group-activated benzylidene

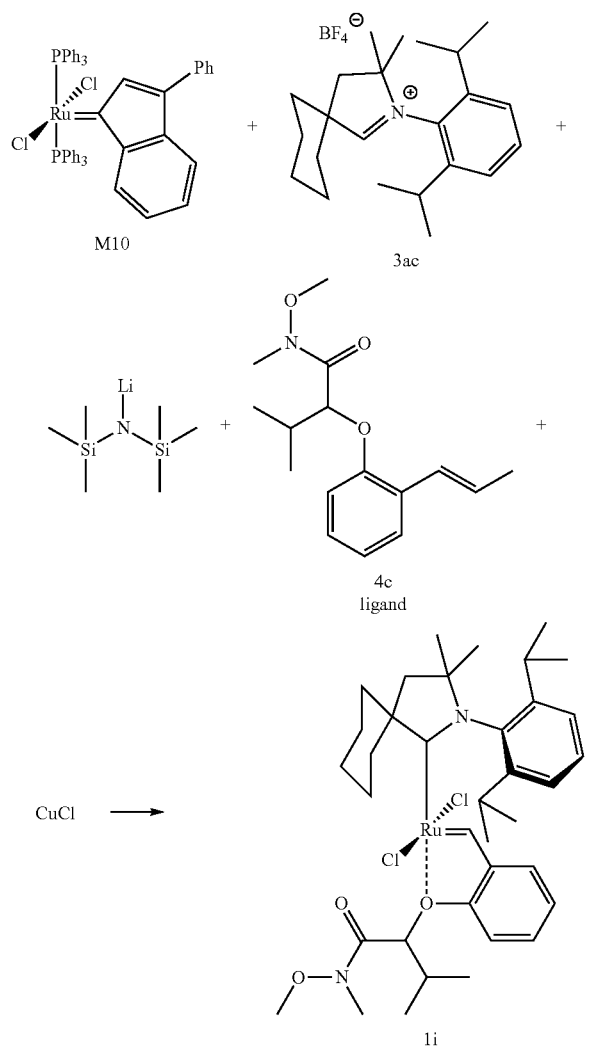

To salt 3ac (1.16 g, 2.8 mmol, 2 molar equivalents) dry deoxygenated toluene (11 ml) was added in argon atmosphere. The mixture was heated to 80° C. and solution of LiHMDS in toluene (1 M, 2.8 ml, 2.8 mmol, 2 molar equivalents) was added. After 1 minute solid complex M10 (1.24 g, 1.4 mmol, 1 molar equivalent) was added. After 2 minutes the mixture was cooled down to 60° C. Benzylidene ligand 4c (0.466 g, 1.68 mmol, 1.2 molar equivalents) and CuCl (0.485 g, 4.9 mmol, 3.5 molar equivalents) were added. Reaction mixture was stirred for 5 minutes at 60° C. and cooled down to the room temperature. The crude product was isolated by column chromatography on silica gel (eluent: toluene→ethyl acetate/cyclohexane 3:7 v/v). Green fraction was collected and concentrated to dryness. The residue was dissolved in ethyl acetate and filtrated. The solvent was evaporated and the residue was dissolved in a minimal amount of methylene chloride and n-heptane was added. Methylene chloride was removed slowly on the evaporator, the resulting crystals were filtered off, washed with a small amount of n-heptane and dried under high vacuum giving green crystalline solid—precatalyst 1 i (0.324 g, 31%).

$^1$H NMR (CD$_2$Cl$_2$, 500 MHz): δ=16.74 (s, 1H), 7.62-7.55 (m, 1H), 7.48-7.38 (m, 2H), 7.28 (d, J=7.7 Hz, 1H), 7.07 (d, J=8.4 Hz, 1H), 6.93 (td, J=7.4; 0.8 Hz, 1H), 6.84 (dd, J=7.5; 1.7 Hz, 1H), 5.51 (d, J=8.3 Hz, 1H), 3.73 (s, 3H), 3.35 (s, 3H), 3.16 (sept, J=6.5 Hz, 1H), 2.80-2.70 (m, 2H), 2.65 (sept, J=6.7 Hz, 1H), 2.22 (t, J=6.3 Hz, 2H), 1.36 (s, 3H), 1.33 (s, 3H), 1.32-1.28 (m, 6H), 1.25 (s, 3H), 1.19 (dd, J=15.4; 6.6 Hz, 6H), 0.98 (dd, J=8.8; 6.8 Hz, 6H), 0.76 (d, J=6.3 Hz, 3H), 0.57 (d, J=6.4 Hz, 3H) ppm.

$^{13}$C NMR (CD$_2$Cl$_2$, 125 MHz): δ=299.3, 267.8, 169.1, 154.6, 148.8, 148.6, 145.1, 144.1, 137.8, 132.9, 130.2, 130.0, 129.7, 126.3, 126.0, 125.1, 124.2, 123.4, 113.4, 45.5, 37.3, 35.5, 34.6, 32.5, 32.0, 31.7, 30.2, 29.9, 29.6, 29.1, 24.8, 24.0, 23.8, 23.7, 22.4, 19.9, 18.3 ppm.

LRMS-ESI calculated for C$_{38}$H$_{57}$N$_2$O$_4$Ru [M−2Cl+CH$_3$O]+: 707.3; found: 707.3.

HRMS-ESI calculated for C$_{37}$H$_{54}$N$_2$O$_3$NaCl$_2$Ru [M+Na]+: 769.2453; found 769.2437.

Example XV

Preparation method of intermediate 5a from first generation precursor M1.

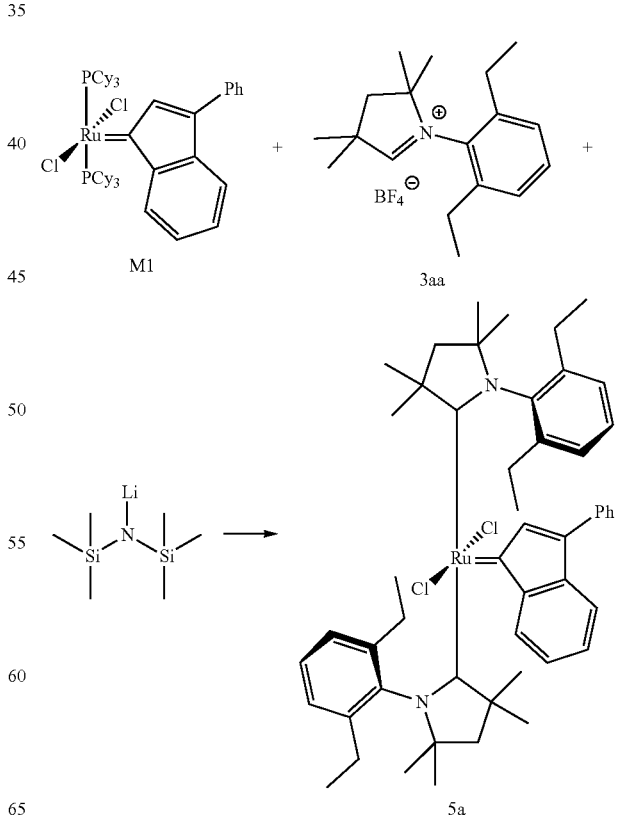

To salt 3aa (1.20 g, 3.48 mmol, 2 molar equivalents) dry deoxygenated toluene (14 ml) was added in argon atmosphere. The mixture was heated to 80° C. and solution of LiHMDS in toluene (1 M, 3.48 ml, 3.48 mmol, 2 molar equivalents) was added. After 1 minute solid complex M1 (1.60 g, 1.74 mmol, 1 molar equivalent) was added. After 20 minutes the mixture was cooled down to the room temperature. Reaction mixture was filtrated through a small amount of silica gel and washed with toluene. The crude product was isolated by column chromatography on silica gel (eluent: ethyl acetate/cyclohexane 1:9 v/v). Red fraction was collected and concentrated to dryness. It was dissolved in n-pentane and slowly concentrated to dryness (the product crystallised during solvent removal). Red crystalline solid was obtained—an intermediate compound 5a (1.07 g, 70%).

$^1$H NMR (C$_6$D$_6$, 500 MHz): δ=9.74 (d, J=7.7 Hz, 0.25H), 9.09 (d, J=7.3 Hz, O.5H), 8.16 (s, 0.25H), 7.95-7.75 (m, 2H), 7.55-7.18 (m, 6H), 7.10-6.20 (m, 7H), 3.86-3.66 (m, 1H), 3.30-2.50 (m, 6H), 2.37 (d, J=13.0 Hz, 9H), 1.75-1.22 (m, 12H), 1.10-0.85 (m, 20H) ppm.

$^{13}$C NMR (CD$_2$Cl$_2$. 125 MHz): δ=279.9, 278.5, 277.8, 276.2, 145.5, 144.1, 143.6, 143.5, 141.3, 141.1, 140.8, 140.7, 140.2, 139.0, 138.6, 138.4, 137.9, 137.6, 134.3, 134.1, 130.6, 129.8, 129.4, 129.2, 128.2, 127.9, 127.6, 127.4, 127.0, 126.9, 126.7, 125.7, 125.5, 124.9, 124.7, 116.5, 116.1, 81.3, 79.7, 61.5, 56.9, 56.4, 55.0, 34.7, 32.5, 32.0, 31.5, 31.0, 30.5, 30.3, 30.0, 29.9, 29.6, 29.2, 27.5, 27.4, 25.3, 25.2, 24.7, 22.9, 14.8, 14.7, 14.4, 13.5, 13.2, 12.9 ppm.

LRMS-ESI calculated for C$_{51}$H$_{64}$ClN$_2$Ru [M–Cl]+: 841.4; found: 841.4.

HRMS-ESI calculated for C$_{51}$H$_{64}$N$_2$Cl$_2$Ru [M–]+: 876.3490; found 876.3471.

Elemental analysis: calculated for C$_{51}$H$_{64}$N$_2$Cl$_2$Ru:

C 69.84; H 7.36; N 3.19; Cl 8.08; found: C 69.88; H 7.22; N 3.21; Cl 8.05.

Example XVI

Preparation method of intermediate 5a from precursor M1—attempt with a greater amount CAAC salt 3aa—here 3 molar equivalents.

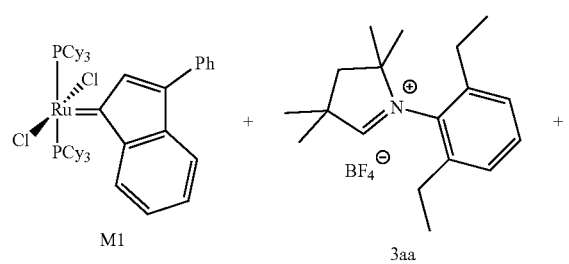

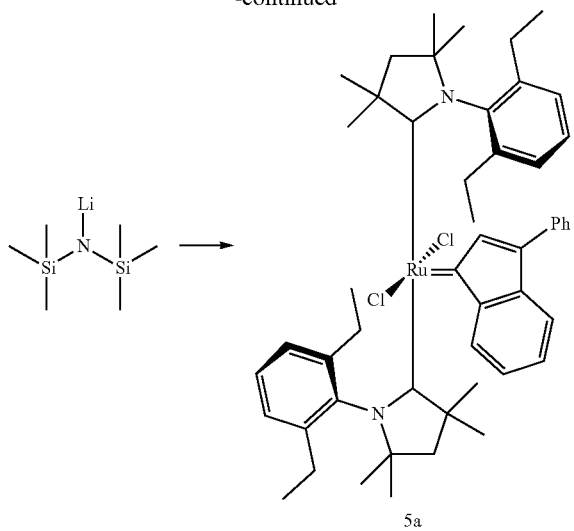

To salt 3aa (1.40 g, 4.05 mmol, 3 molar equivalents) dry deoxygenated toluene (10 ml) was added in argon atmosphere. The mixture was heated to 80° C. and solution of LiHMDS in toluene (1 M, 4.05 ml, 4.05 mmol, 3 molar equivalents) was added. After 1 minute solid complex M1 (1.25 g, 1.35 mmol, 1 molar equivalent) was added. After 5 minutes the mixture was cooled down to the room temperature. Reaction mixture was filtrated through a small amount of silica gel and washed with toluene. The crude product was isolated by column chromatography on silica gel (eluent: ethyl acetate/cyclohexane 1:9 v/v). Red fraction was collected and concentrated to dryness. It was dissolved in n-pentane and slowly concentrated to dryness (the product crystallised during solvent removal). Red crystalline solid was obtained—an intermediate compound 5a (1.02 g, 86%). Comparison with Example XV.

Example XVII

Preparation method of precatalyst 1a—one-step procedure from intermediate 5a.

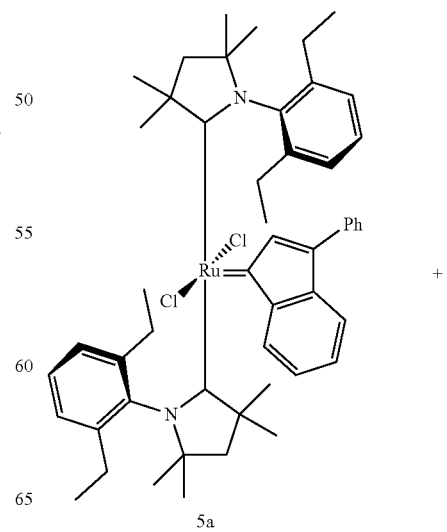

53

-continued

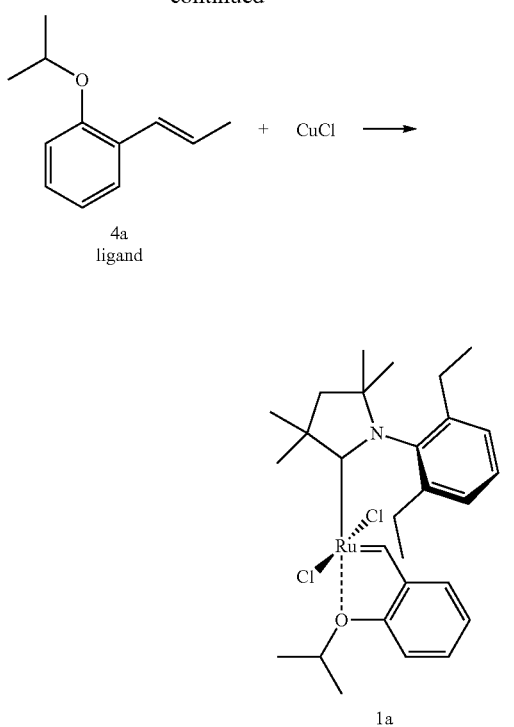

To the solution of an intermediate 5a (0.948 g, 1.08 mmol, 1 molar equivalent) in dry deoxygenated toluene (10 ml) at 60° C. benzylidene ligand 4a (0.228 g, 1.29 mmol, 1.2 molar equivalents) and Cu Cl (0.214 g, 2.16 mmol, 2 molar equivalents) were added. Reaction mixture was stirred for 30 minutes and cooled down to the room temperature. The crude product was isolated by column chromatography on silica gel (eluent: toluene). Green fraction was collected and concentrated to dryness. The residue was dissolved in ethyl acetate and filtrated. The solvent was evaporated, the residue was washed with isopropanol and dried under high vacuum giving green crystalline solid—precatalyst 1a (0.390 g, 62%).

Example XVIII

Preparation method of intermediate 5b from first generation precursor Gru-1.

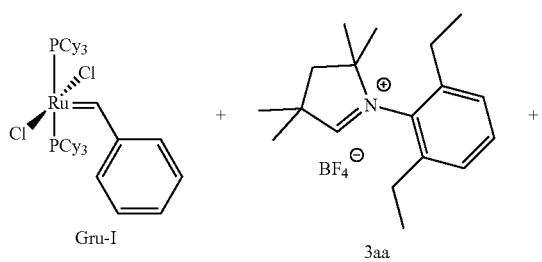

54

-continued

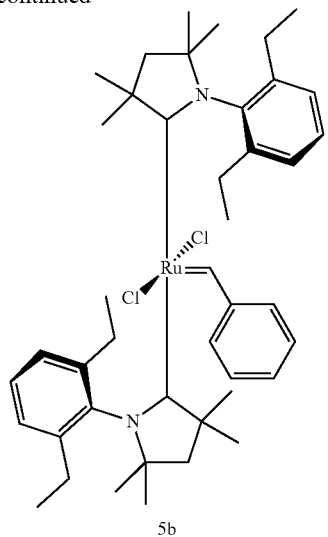

To salt 3aa (2.76 g, 8.0 mmol, 2 molar equivalents) dry deoxygenated toluene (32 ml) was added in argon atmosphere. The mixture was heated to 80° C. and solution of LiHMDS in toluene (1 M, 8.0 ml, 8.0 mmol, 2 molar equivalents) was added. After 2 minutes solid complex Gru-1 (3.29 g, 4.0 mmol, 1 molar equivalent) was added. After 25 minutes the mixture was cooled down to the room temperature. Reaction mixture was filtrated through a small amount of silica gel and washed with toluene. The crude product was isolated by column chromatography on silica gel (eluent: ethyl acetate/cyclohexane 1:9 v/v). Brown fraction was collected and concentrated to dryness. It was dissolved in n-pentane and slowly concentrated (the product crystallised during solvent removal). It was filtrated off and washed with cold n-pentane. Brown crystalline solid was obtained—an intermediate compound 5b (1.55 g, 50%).

A mixture of isomers A:B=3.2:1. Due to a very complex $^1$H NMR spectrum only the characteristic benzylidene proton shifts were given: isomer A: singlet 17.60 ppm, isomer B: singlet 18.52 ppm (CD2Cl2).

$^{13}$C NMR (CD2Cl$_2$, 125 MHz): δ=283.7, 280.0, 279.9, 278.7, 150.6, 148.3, 143.7, 143.1, 141.6, 141.0, 128.4, 127.7, 127.5, 127.4, 127.3, 127.2, 53.7, 53.4, 32.3, 31.7, 31.1, 30.9, 30.6, 15.2, 14.9, 14.5, 14.4, 12.5, 12.4 ppm.

LRMS-ESI calculated for $C_{43}H_{60}ClN_2Ru$ [M−Cl]+: 741.3; found: 741.3.

HRMS-ESI calculated for $C_{43}H_{60}N_2Cl_2Ru$ [MY 776.3177; found 776.3156.

Elemental analysis: calculated for $C_{43}H_{60}N_2Cl_2Ru$: C 66.47; H 7.78; N 3.61; Cl 9.13; found: C 66.42; H 7.75; N 3.59; Cl 9.18.

Example XIX

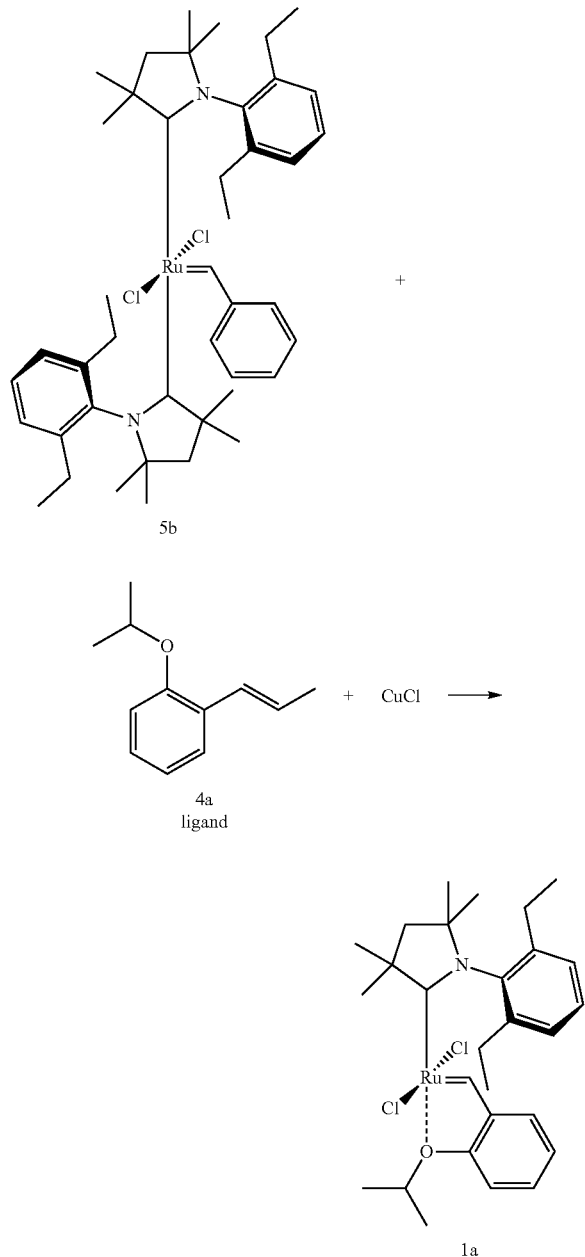

To the solution of intermediate 5b (0.801 g, 1.03 mmol, 1 molar equivalent) in dry deoxygenated toluene (10 ml) at 60° C. benzylidene ligand 4a (0.217 g, 1.23 mmol, 1.2 molar equivalents) and CuCl (0.204 g, 2.06 mmol, 2 molar equivalents) were added. Reaction mixture was stirred for 10 minutes and cooled down to the room temperature. The crude product was isolated by column chromatography on silica gel (eluent: toluene). Green fraction was collected and concentrated to dryness. The residue was dissolved in ethyl acetate and filtrated. The solvent was evaporated, the residue was washed with isopropanol and dried under high vacuum giving green crystalline solid—precatalyst 1a (0.385 g, 65%).

Example XX

Preparation method of precatalyst 1j containing hydroxamic group-activated benzylidene and iodide ligands.

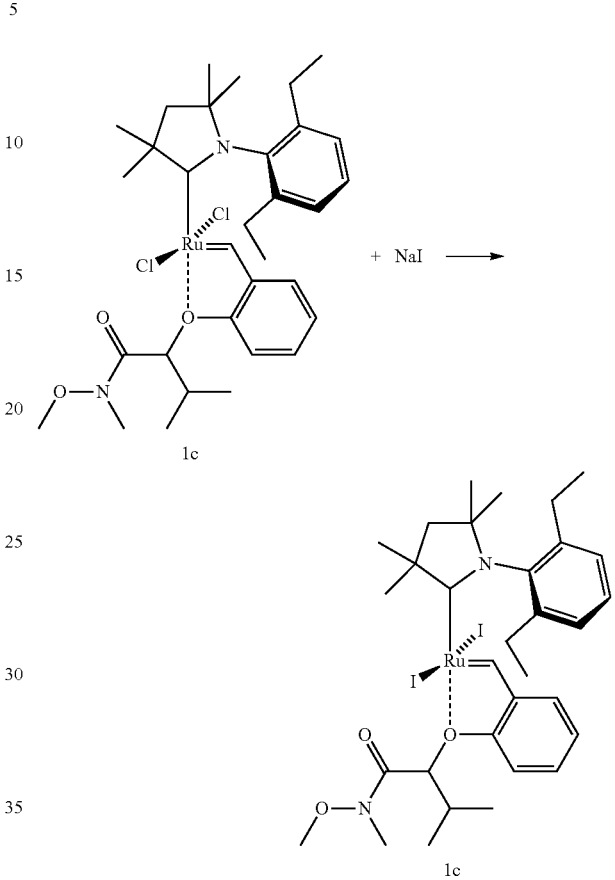

To suspension of sodium iodide (1.04 g, 6.97 mmol, 30 molar equivalents) in acetone (2.3 ml) solid precatalyst 1c (0.158 g, 0.232 mmol, 1 molar equivalent) was added. The whole was stirred at room temperature for 3 hours and then concentrated to dryness. The residue was dissolved in methylene chloride and inorganic salts were removed by filtration. The residue was filtrated through a small amount of silica gel (eluent ethyl acetate/cyclohexane 3:7 v/v). The solvent was evaporated and the residue was dissolved in a minimal amount of methylene chloride and n-heptane was added. Methylene chloride was removed slowly on the evaporator, the resulting crystals were filtered off, washed with a small amount of n-heptane and dried under high vacuum giving green crystalline solid 1j (0.178 g, 89%).

$^1$H NMR (CD$_2$Cl$_2$, 500 MHz): δ=15.83 (s, 1H), 7.60 (dt, J=8.7; 4.6 Hz, 1H), 7.57-7.52 (m, 1H), 7.47-7.44 (m, 1H), 7.42-7.38 (m, 1H), 7.03 (d, J=8.3 Hz, 1H), 6.95 (d, J=4.5 Hz, 2H), 5.50 (d, J=7.7 Hz, 1H), 3.87 (s, 3H), 3.41 (s, 3H), 3.24 (dq, J=15.1; 7.5 Hz, 1H), 2.80-2.62 (m, 3H), 2.44-2.36 (m, 4H), 2.24-2.20 (m, 1H), 2, 15 (s, 3H), 2.14-2.10 (m, 1H), 1.35 (s, 3H), 1.26 (s, 3H), 1.20 (t, J=7.4 Hz, 3H), 1.04 (dd, J=7.0; 5.3 Hz, 6H), 0.94 (t, J=7.4 Hz, 3H) ppm.

$^{13}$C NMR (CD$_2$Cl$_2$, 125 MHz): δ=306.5, 271.3, 170.8, 155.0, 146.3, 144.1, 143.7, 140.3, 130.2, 129.0, 127.3, 127.0, 123.8, 123.3, 113.6, 80.9, 78.4, 62.5, 55.7, 53.2, 35.2, 34.8, 33.4, 32.6, 30.0, 29.5, 27.2, 26.7, 20.8, 18.6, 15.5, 15.3 ppm.

HRMS-ESI calculated for $C_{32}H_{46}IN_2O_3Ru$ [M−1]+: 735.1600; found: 735.1636.

Elemental analysis: calculated for $C_{32}H_{46}N_2I_2O_3Ru$:
C 44.61; H 5.38; N 3.25; I 29.46; found: C 44.47; H 5.37; N 3.21; I 29.29.

Example XXI

Application of precatalysts 1a-1j in ring-closing metathesis (RCM) reactions of diethyl diallylomalonate 51 leading to a cyclic compound P1.

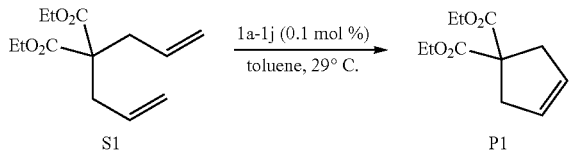

To the solution of diethyl diallylomalonate S1 (120.1 mg, 0.5 mmol) in dry deoxygenated toluene (5 ml) at 29° C. a solution of respective precatalyst (1a-1 j), 0.1 mol %) in dry deoxygenated toluene (50 µl) was added. It was stirred in argon atmosphere. At certain time intervals 0.1 ml samples of reaction mixture were collected to which one drop of ethyl vinyl ether was added to deactivate the catalyst. The substrate conversion as a function of time was determined by GC analysis. A summary is presented in Table 1.

TABLE 1

DEDAM conversion as a function of time.

| Time (min) | 1a | 1b | 1c | 1d | 1e | 1f | 1g | 1h | 1i | 1j |
|---|---|---|---|---|---|---|---|---|---|---|
| 5 | 6 | 10 | 67 | 6 | 9 | 80 | — | — | — | 5 |
| 10 | 19 | 32 | 87 | 16 | 31 | 94 | — | — | — | 20 |
| 20 | 43 | 63 | 95 | 38.5 | 71 | 98 | — | — | — | 47 |
| 30 | 62 | 76 | 97 | 54 | 86 | 99 | — | — | — | 60 |
| 45 | 77 | 85 | 98 | 68 | 93 | 99.5 | — | — | — | 71 |
| 60 | 84 | 90 | 98.5 | 77 | 95 | 99.5 | — | — | — | 77 |
| 120 | 92 | 95 | 99 | 88 | 98 | 99.5 | — | — | — | 86 |
| 180 | — | — | — | 91 | 99 | 99.6 | 2.3 | 5 | 30 | 89 |

Example XXII

Application of precatalyst 5a in ring-closing metathesis (RCM) reactions of diethyl diallylomalonate 51 leading to cyclic compound P1.

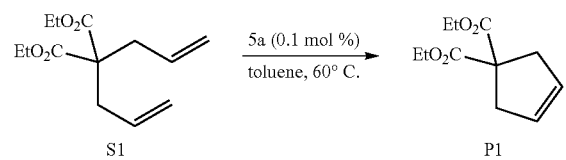

To the solution of diethyl diallylomalonate 51 (480.6 mg, 2.0 mmol) in dry deoxygenated toluene (20 ml) at 60° C. a solution of precatalyst 5a (1.75 mg, 0.002 mmol, 0.1 mol %) in dry deoxygenated toluene (50 µl) was added. In case of reaction with CAAC carbene scavenger, CuCl (1.98 mg, 0.02 mmol) was added to the reaction mixture. The whole was stirred in argon atmosphere. At certain time intervals 0.1 ml samples of reaction mixture were collected to which one drop of ethyl vinyl ether was added to deactivate the catalyst. Conversion reaction as a function of time was determined by GC analysis. A summary is presented in Table 2.

TABLE 2

DEDAM conversion with intermediate 5a as a function of time.

| | Conversion (%) | |
|---|---|---|
| Time (min) | 5a | 5a + CuCl |
| 15 | 7 | >99 |
| 30 | 10 | — |
| 60 | 27 | — |
| 120 | 78 | — |
| 240 | 88 | — |
| 360 | 95 | — |

Example XXIII

Application of precatalysts 1a-1j in ethenolysis reactions of fatty acid methyl esters which were obtained by rapeseed oil transesterification (MOR).

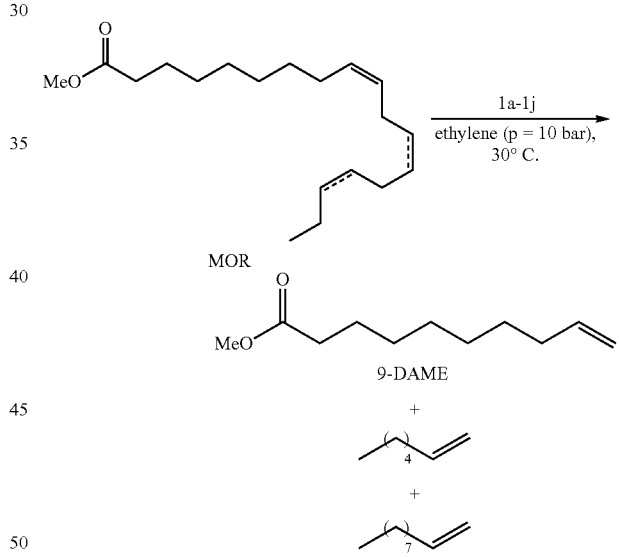

To the reaction, a mixture of fatty acid methyl esters which were obtained by rapeseed oil transesterification (MOR), was used, composed of: about 61% methyl oleate, about 21'Y° linoleic acid methyl ester, about 10% a-linolenic acid ester, about 7% saturated fatty acid methyl esters including about 4% methyl palmitate and about 2% methyl stearate.

To degassed MOR (610 g) cooled to 0° C. a solution of catalyst (0.052 mmol) in dry deoxygenated toluene (5 ml) was added. The mixture was vacuum-pumped to an autoclave and stirred for 2 hours at 30° C. at 10 bar of ethylene. After 2 hours the reaction was quenched and to the reaction mixture 6 ml 0.1 M solution of SnachCat [CAS: 51641-96-4] was added to deactivate the catalyst.

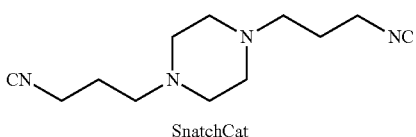

SnatchCat

The samples were analyzed using gas chromatography. The conversion was determined using methyl palmitate as an internal standard.

Reaction mixtures obtained in reactions catalysed with 1d and 1e after filtration through short pad of silica gel were distilled under reduced pressure, giving 173 g and 179 g of 9-decenoic acid methyl ester (9-DAME), respectively.

Conversion and percentage (GC peak area) of 9-decenoic acid methyl ester (9-DAME) were given in the Table 3.

TABLE 3

MOR conversion in ethenolysis reaction with precatalysts 1a-1i

| Pre catalyst | Conversion (%) | Percentage of 9-DAME (%) in the reaction mixture based on GC | Isolated 9-DAME (g) |
|---|---|---|---|
| 1a | 77 | 25 | — |
| 1b | 71 | 23 | — |
| 1c | 69 | 21 | — |
| 1d | 83 | 31 | 173 |
| 1e | 79 | 29 | 179 |
| 1j | 27 | 8 | — |
| 1i | 21 | 5 (reaction conducted at 40° C.) | — |

Analytical data obtained for 9-DAME:

$^1$H NMR (CDCl$_3$, 500 MHz): δ=5.79 (ddt, J=17.0; 10.2; 6.7 Hz, 1H), 4.98 (dq, J=17.1; 1.7 Hz, 1H), 4.92 (ddd, J=11.4; 2.3; 1.2 Hz, 1H), 3.66 (s, 3H), 2.29 (t, J=7.5 Hz, 2H), 2.06-1.99 (m, 2H), 1.66-1.56 (m, 2H), 1.40-1.24 (m, 8H) ppm.

$^{13}$C NMR (CDCl$_3$, 125 MHz): 174.3, 139.1, 114.2, 51.4, 34.1, 33.7, 29.1, 28.9, 28.8, 24.9 ppm.

Example XXIV

Preparation method of intermediate 5c from precursor M10 and CAAC salt 3ad.

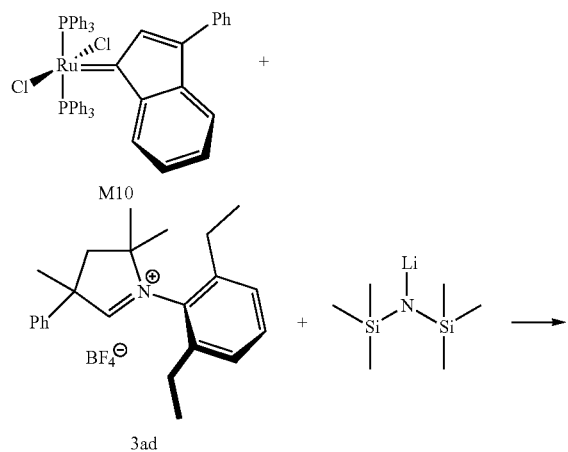

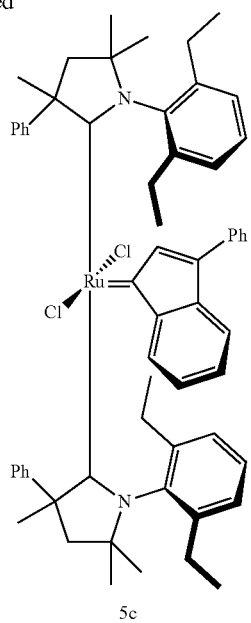

5c

To salt 3ad (6.00 g, 14.73 mmol, 3 molar equivalents) in argon atmosphere dry deoxygenated toluene (35 ml) was added. The mixture was heated to 80° C. and solution of LiHMDS in toluene (1 M, 14.73 ml, 14.73 mmol, 3 molar equivalents) was added. After 1 minute solid complex M10 (4.35 g, 4.91 mmol, 1 molar equivalent) was added. After 2 minutes the mixture was cooled down to the room temperature. Triethylamine (2 ml) was added and filtrated through a short pad of silica gel (deactivated with triethylamine), which was washed with 100 ml toluene/triethylamine mixture (95:5 v/v). Solvents were evaporated under reduced pressure. The crude product was isolated by column chromatography on silica gel (deactivated with triethylamine; eluent: from cyclohexane/triethylamine (95:5 v/v) to cyclohexane/ethyl acetate/triethylamine (90:5:5 v/v/v)). Red brown fraction was collected and concentrated to dryness. The residue was dissolved in n-pentane. Solvent was evaporated to 25% of its original amount—precipitate formed during evaporation was filtrated off, washed with a minimal amount of cold n-pentane and dried under high vacuum giving an orange brown crystalline solid—compound 5c (1.73 g, 35%).

$^1$H NMR (C$_5$D$_6$, 500 MHz): δ=9.59 (d, J=7.5 Hz, 1H), 8.06 (d, J=7.7 Hz, 2H), 7.76 (d, J=7.4 Hz, 2H), 7.49-7.43 (m, 3H), 7.42-7.37 (m, 2H), 7.37-7.23 (m, 6H), 7.22-7.06 (m, 5H), 7.01-6.97 (m, 1H), 6.88 (t, J=7.3 Hz, 1H), 6.81 (d, J=7.6 Hz, 1H), 6.64 (t, J=7.6 Hz, 1H), 6.34 (d, J=7.5 Hz, 1H), 4.14 (dq, J=14.9; 7.2 Hz, 1H), 3.10-2.83 (m, 4H), 2.83-2.73 (m, 1H), 2.73-2.63 (m, 1H), 2.57-2.48 (m, 1H), 2.05 (d, J=12.3 Hz, 1H), 1.94-1.89 (m, 1H), 1.84 (d, J=12.7 Hz, 1H), 1.78 (s, 3H), 1.62 (d, J=12.7 Hz, 1H), 1.48-1.40 (m, 6H), 1.03 (dt, J=14.5; 7.3 Hz, 6H), 0.95 (dt, J=14.5; 7.3 Hz, 3H), 0.77 (s, 3H), 0.71 (s, 3H), 0.63 (s, 3H), 0.50 (s, 3H) ppm.

$^{13}$C NMR (CD$_2$Cl$_2$, 125 MHz): δ=288.1, 279.5, 273.4, 263.3, 150.5, 148.9, 148.1, 147.8, 147.2, 146.6, 144.9, 143.8, 143.8, 143.3, 142.0, 141.6, 141.4, 140.5, 140.2, 139.0, 138.9, 138.6, 138.1, 137.9, 137.5, 136.6, 135.9, 135.0, 131.0, 130.7, 130.4, 130.0, 129.9, 129.7, 129.2, 128.8, 128.7, 128.2, 128.1, 127.8, 127.7, 127.6, 127.5, 127.4, 127.3, 127.3, 127.2, 127.2, 127.2, 127.0, 126.9, 126.8, 126.6, 126.5, 126.4, 126.3, 126.3, 126.1, 125.4, 125.0, 124.7, 118.7, 116.5, 115.7, 96.2, 81.5, 80.5, 79.0, 68.9, 66.0, 65.1, 57.1, 55.4, 52.1, 49.1, 44.4, 32.2, 31.5, 30.2, 29.7, 29.4, 29.1, 28.6, 28.0, 27.7, 27.6, 27.3, 27.2, 26.6, 25.7, 25.5, 24.8, 24.8, 24.4, 16.3, 16.1, 14.5, 14.4, 14.0, 13.6, 13.4, 12.4 ppm.

HRMS-ESI calculated for $C_{61}H_{68}N_2Cl_2Ru$ [M]+: 1000.3803; found 1000.3798.

Elemental analysis: calculated for $C_{61}H_{68}N_2Cl_2Ru$: C 73.18; H 6.85; N 2.80; Cl 7.08; found: C 73.14; H 7.00; N 2.95; Cl 7.10.

Example XXV

Preparation method of intermediate 5d from precursor M10 and CAAC salt 3ae.

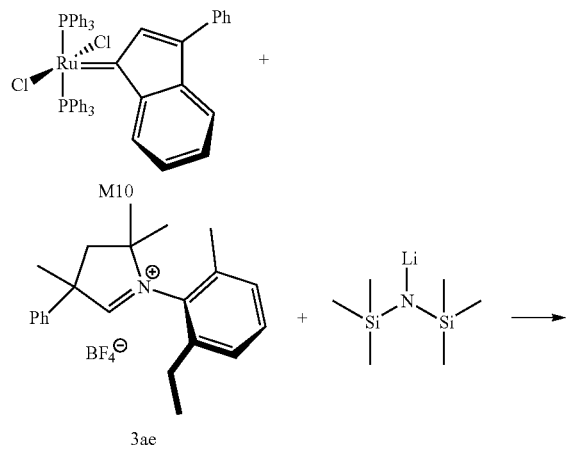

3ae

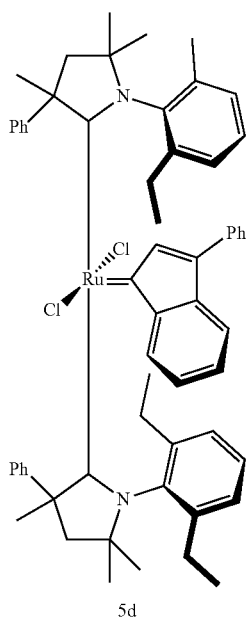

5d

To salt 3ae (2.36 g, 6.0 mmol, 3 molar equivalents) dry deoxygenated toluene (14 ml) was added in argon atmosphere. The mixture was heated to 80° C. and solution of LiHMDS in toluene (1 M, 6.0 ml, 6.0 mmol, 3 molar equivalents) was added. After 1 minute solid complex M10 (1.77 g, 2.0 mmol, 1 molar equivalent) was added. After 2 minutes the mixture was cooled down to the room temperature. Triethylamine (2 ml) was added and filtrated through a short pad of silica gel (deactivated with triethylamine), which was washed with SO ml toluene/triethylamine mixture (95:5 v/v). Solvents were evaporated under reduced pressure. The crude product was isolated by column chromatography on silica gel (deactivated with triethylamine; eluent: from cyclohexane/triethylamine (95:5 v/v) to cyclohexane/ethyl acetate/triethylamine (90:5:5 v/v/v)). Red brown fraction was collected and concentrated to dryness. The residue was dissolved in n-pentane. Solvent was evaporated to 25% of its original amount—precipitate formed during evaporation was filtrated off, washed with a minimal amount of cold n-pentane and dried under high vacuum giving an orange brown crystalline solid—compound 5d (0.345 g, 18%).

$^1$H NMR ($C_6D_6$, 500 MHz): δ=9.69-9.49 (m, 1H), 8.17-7.99 (m, 2H), 7.82-7.65 (m, 2H), 7.60-7.23 (m, 9H), 7.23-7.04 (m, 6H), 7.02-6.10 (m, 6H), 3.14-2.76 (m, 4H), 2.74-2.46 (m, 2H), 2.38-2.24 (m, 3H), 2.10-1.35 (m, 12H), 1.31-1.23 (m, 2H), 1.08-0.92 (m, SH), 0.80-0.59 (m, 10H) ppm.

$^{13}$C NMR ($C_5D_6$, 125 MHz): δ=290.2, 289.9, 289.0, 288.6, 280.9, 279.2, 279.1, 274.5, 274.2, 274.0, 149.4, 149.3, 149.3, 149.2, 149.0, 148.3, 145.3, 145.3, 145.2, 144.4, 144.2, 144.1, 144.1, 142.4, 142.1, 141.9, 141.8, 141.8, 141.1, 140.9, 139.6, 139.4, 139.2, 139.1, 139.0, 138.8, 138.6, 138.2, 138.1, 138.1, 136.9, 136.6, 136.0, 136.0, 135.7, 135.6, 135.5, 135.2, 131.1, 131.0, 130.9, 130.8, 130.7, 130.6, 130.4, 130.3, 130.1, 130.0, 129.9, 129.7, 129.6, 129.5, 129.1, 129.1, 129.0, 128.7, 128.3, 128.0, 127.9, 127.8, 127.8, 127.7, 127.7, 127.7, 127.6, 127.6, 127.3, 127.2, 126.8, 126.8, 126.7, 126.5, 126.3, 124.8, 124.6, 116.9, 116.9, 81.7, 81.5, 81.1, 80.9, 80.7, 69.1, 69.0, 65.4, 65.3, 65.2, 56.8, 56.7, 56.6, 55.5, 55.1, 53.9, 53.6, 31.0, 30.7, 30.2, 29.9, 29.9, 29.6, 29.6, 29.5, 29.3, 29.2, 29.0, 28.0, 27.9, 27.6, 27.4, 27.4, 27.3, 27.1, 25.8, 25.5, 25.4, 25.2, 25.1, 25.1, 25.0, 24.2, 24.0, 22.7, 22.6, 14.9, 14.8, 14.0, 13.8, 12.6, 12.6 ppm.

HRMS-ESI: calculated for $C_{59}H_{64}N_2Cl_2Ru$ [M−]+: 972.3490; found 972.3475. Elemental analysis: calculated for $C_{59}H_{64}N_2Cl_2Ru$:
C 72.82; H 6.63; N 2.88; Cl 7.29; found: C 72.69; H 6.68; N 2.71; Cl 7.07.

Example XXVI

Preparation method of intermediate 5e from precursor M10 and CAAC salt 3ab.

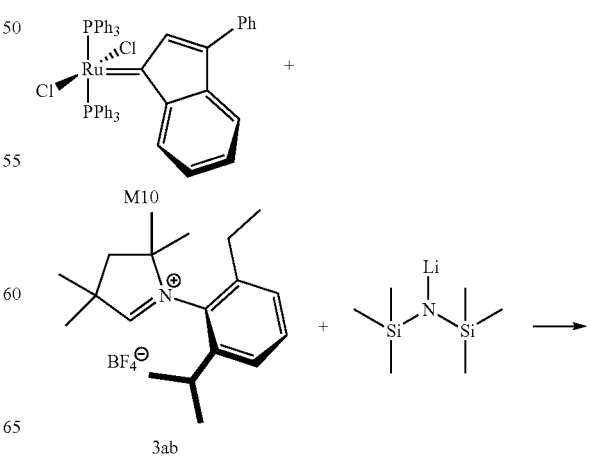

3ab

Example XXVII

Preparation method of intermediate 5e from precursor M1 and CAAC salt 3ab.

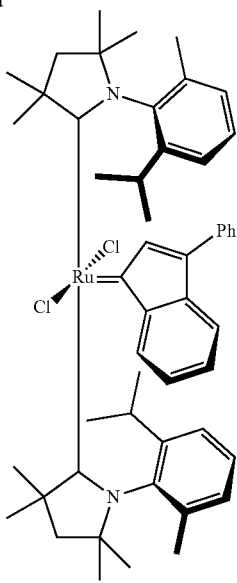

5e

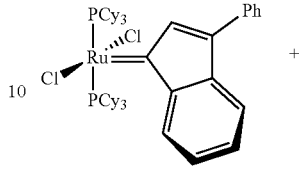

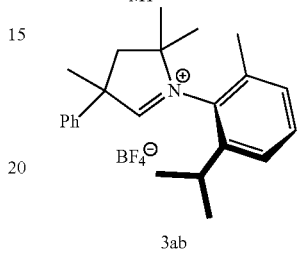

3ab

To salt 3ab (8.29 g, 24.0 mmol, 3 molar equivalents) dry deoxygenated toluene (56 ml) was added in argon atmosphere. The mixture was heated to 80° C. and solution of LiHMDS in toluene (1 M, 24.0 ml, 24.0 mmol, 3 molar equivalents) was added. After 1 minute solid complex M10 (7.09 g, 8.0 mmol, 1 molar equivalent) was added. After 2 minutes the mixture was cooled down to the room temperature. Triethylamine (5 ml) was added and filtrated through a short pad of silica gel (deactivated with triethylamine), which was washed with 75 ml toluene/triethylamine mixture (95:5 v/v). Solvents were evaporated under reduced pressure. The crude product was isolated by column chromatography on silica gel (deactivated with triethylamine; eluent: from cyclohexane/triethylamine (95:5 v/v) to cyclohexane/ethyl acetate/triethylamine (90:5:5 v/v/v)). Red brown fraction was collected and concentrated to dryness. The residue was dissolved in n-pentane. Solvent was evaporated to 25% of its original amount—precipitate formed during evaporation was filtrated off, washed with a minimal amount of cold n-pentane and dried under high vacuum giving an orange brown crystalline solid—compound 5e (2.89 g, 41%).

$^1$H NMR (C$_6$D$_6$, 500 MHz): δ=10.05-8.65 (m, 1H), 8.50-7.45 (m, 3H), 7.40-7.15 (m, 7H), 7.05-6.05 (m, SH), 3.86-3.62 (m, 1H), 3.12-2.89 (m, 1H), 2.86-2.02 (m, 8H), 1.92-1.11 (m, 22H), 1.10-0.65 (m, 14H), 0.44 (s, 2H) ppm.

$^{13}$C NMR (CD2Cl$_2$, 125 MHz): δ=281.7, 281.0, 280.1, 279.1, 278.5, 147.6, 146.3, 142.0, 141.8, 141.1, 136.7, 136.4, 136.1, 134.0, 131.8, 130.7, 130.0, 129.8, 129.5, 129.4, 127.2, 127.0, 126.6, 125.8, 125.4, 116.6, 116.5, 80.3, 80.3, 62.7, 61.9, 61.4, 57.3, 56.8, 56.0, 32.0, 31.4, 30.8, 30.0, 28.9, 28.8, 28.6, 28.4, 27.8, 27.5, 27.3, 26.9, 26.5, 26.4, 25.7, 25.4, 24.0, 23.8, 23.2, 22.7 ppm.

HRMS-ESI calculated for C$_{51}$H$_{64}$N$_2$Cl$_2$Ru [MY: 876.3490; found 876.3477.

Elemental analysis: calculated for C$_{51}$H$_{64}$N$_2$Cl$_2$Ru: C 69.84; H 7.36; N 3.19; Cl 8.08; found: C 69.94; H 7.43; N 3.14; Cl 8.17.

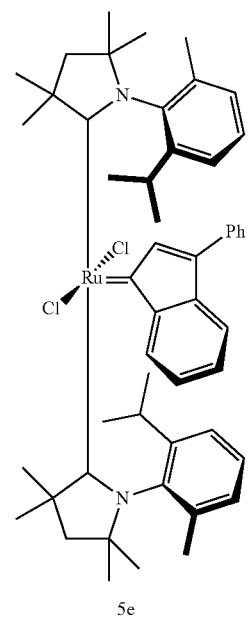

5e

To salt 3ab (1.04 g, 3.0 mmol, 3 molar equivalents) dry deoxygenated toluene (7 ml) was added in argon atmosphere. The mixture was heated to 80° C. and solution of LiHMDS in toluene (1 M, 3.0 ml, 3.0 mmol, 3 molar equivalents) was added. After 1 minute solid complex M1 (0.923 g, 1.0 mmol, 1 molar equivalent) was added. After 10 minutes the mixture was cooled down to the room temperature. Triethylamine (1 ml) was added and filtrated through a short pad of silica gel (deactivated with triethylamine), which was washed with 25 ml toluene/triethylamine mixture (95:5 v/v). Solvents were evaporated under reduced pressure. The crude product was isolated by column chromatography on silica gel (deactivated with triethylamine; eluent: from cyclohexane/triethylamine (95:5 v/v) to cyclohexane/ethyl acetate/triethylamine (90:5:5 v/v/v)). Red brown fraction was collected and concentrated to dryness. The residue was dissolved in n-pentane. Solvent was evaporated to 25% of its original amount—precipitate formed during evaporation was filtrated off, washed with a minimal amount of cold n-pentane and dried under high vacuum giving an orange brown crystalline solid—compound 5e (0.72 g, 82%).

Analytical data for compound 5e obtained in this Example were identical as in Example XXVI.

Example XXVIII

Preparation method of intermediate 5f from precursor M10 and CAAC salt 3af.

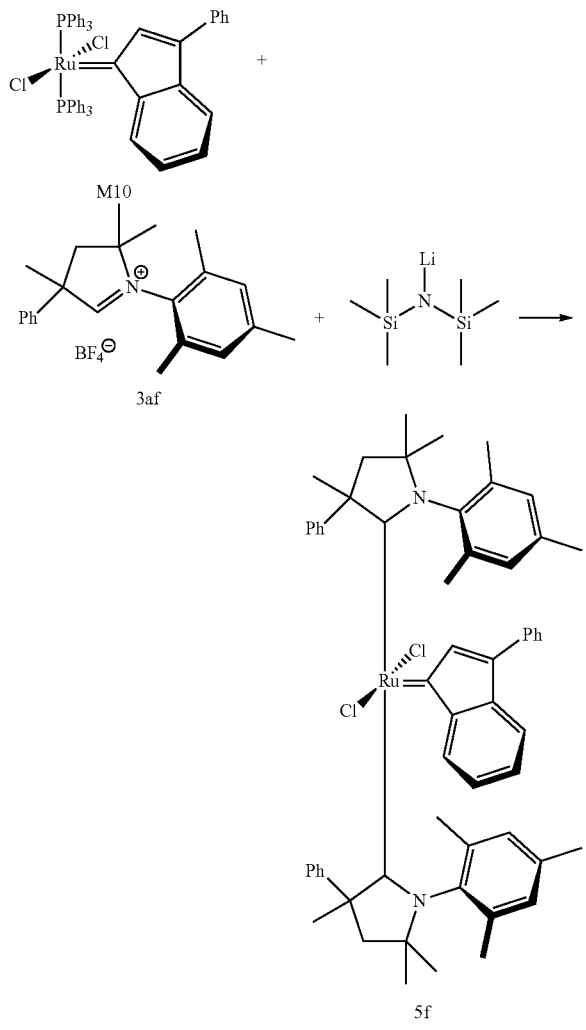

To salt 3af (2.36 g, 6.0 mmol, 3 molar equivalents) dry deoxygenated toluene (14 ml) was added in argon atmosphere. The mixture was heated to 80° C. and solution of LiHMDS in toluene (1 M, 6.0 ml, 6.0 mmol, 3 molar equivalents) was added. After 1 minute solid complex M10 (1.77 g, 2.0 mmol, 1 molar equivalent) was added. After 2 minutes the mixture was cooled down to the room temperature. Triethylamine (2 ml) was added and filtrated through a short pad of silica gel (deactivated with triethylamine), which was washed with 50 ml toluene/triethylamine mixture (95:5 v/v). Solvents were evaporated under reduced pressure. The crude product was isolated by column chromatography on silica gel (deactivated with triethylamine; eluent: from cyclohexane/triethylamine (95:5 v/v) to cyclohexane/ethyl acetate/triethylamine (90:5:5 v/v/v)). Red brown fraction was collected and concentrated to dryness. The residue was dissolved in n-pentane. Solvent was evaporated to 25% of its original amount—precipitate formed during evaporation was filtrated off, washed with a minimal amount of cold n-pentane and dried under high vacuum giving an orange brown crystalline solid—compound 5f (0.210 g, 11%).

$^1$H NMR ($C_6D_6$, 500 MHz): δ=9.57 (d, J=7.6 Hz, 1H), 8.14 (d, J=7.8 Hz, 2H), 7.73 (d, J=7.6 Hz, 2H), 7.61 (s, 1H), 7.52 (d, J=7.5 Hz, 2H), 7.44 (t, J=7.6 Hz, 2H), 7.37-7.16 (m, 5H), 7.15-7.11 (m, 1H), 7.08-6.80 (m, 5H), 6.64 (s, 1H), 6.42 (s, 1H), 5.90 (s, 1H), 2.85 (s, 3H), 2.32 (s, 6H), 2.22 (s, 3H), 2.19 (s, 3H), 2.10 (d, J=12.5 Hz, 1H), 1.95-1.84 (m, 2H), 1.77 (s, 3H), 1.70 (s, 3H), 1.64 (d, J=12.7 Hz, 1H), 1.50 (s, 3H), 0.80 (s, 3H), 0.72 (s, 3H), 0.67 (s, 3H), 0.61 (s, 3H) ppm.

$^{13}$C NMR ($CD_2Cl_2$, 125 MHz): δ=286.8, 278.5, 272.1, 148.7, 147.8, 144.8, 141.2, 139.1, 138.8, 138.5, 138.2, 137.7, 137.6, 136.6, 136.1, 136.0, 135.2, 134.3, 131.7, 131.0, 130.3, 130.2, 129.8, 129.6, 128.8, 128.6, 128.1, 127.5, 127.3, 127.3, 127.0, 126.6, 126.4, 116.0, 82.0, 81.9, 68.8, 65.0, 57.0, 55.6, 30.39, 30.16, 29.55, 28.50, 27.86, 27.37, 24.64, 24.30, 21.91, 21.13, 21.0 ppm.

HRMS-ESI calculated for $C_{59}H_5N_2Cl_2Ru$ [M"]+: 972.3490; found 972.3483.

Elemental analysis: calculated for $C_{59}H_5N_2Cl_2Ru$:

C 72.82; H 6.63; N 2.88; Cl 7.29; found: C 72.88; H 6.78; N 2.71; Cl 7.16.

Example XXIX

Preparation method of intermediate 5g from precursor M10 and CAAC salt 3ag.

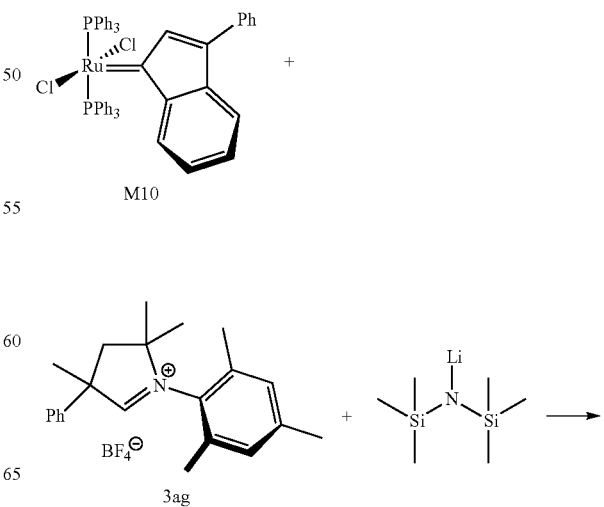

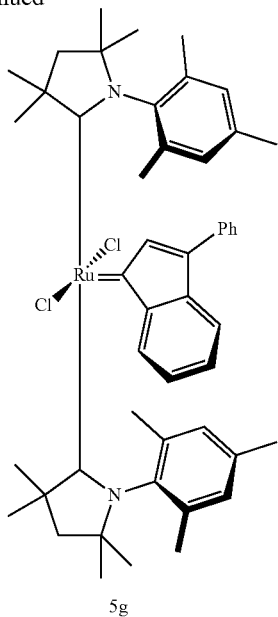

5g

To salt 3ag (1.99 g, 6.0 mmol, 3 molar equivalents) dry deoxygenated toluene (14 ml) was added in argon atmosphere. The mixture was heated to 80° C. and solution of LiHMDS in toluene (1 M, 6.0 ml, 6.0 mmol, 3 molar equivalents) was added. After 1 minute, solid complex M10 (1.77 g, 2.0 mmol, 1 molar equivalent) was added. After 2 minutes the mixture was cooled down to the room temperature. Triethylamine (2 ml) was added and filtrated through a short pad of silica gel (deactivated with triethylamine), which was washed with 50 ml toluene/triethylamine mixture (95:5 v/v). Solvents were evaporated under reduced pressure. The crude product was isolated by column chromatography on silica gel (deactivated with triethylamine; eluent: from cyclohexane/triethylamine (95:5 v/v) to cyclohexane/ethyl acetate/triethylamine (90:5:5 v/v/v)). Red brown fraction was collected and concentrated to dryness. The residue was dissolved in n-pentane. Solvent was evaporated to 25% of its original amount—precipitate formed during evaporation was filtrated off, washed with a minimal amount of cold n-pentane and dried under high vacuum giving an orange brown crystalline solid—compound 5g (0.561 g, 33%).

$^1$H NMR (CD$_2$Cl$_2$, 500 MHz): δ=8.51 (d, J=7.6 Hz, 1H), 7.75-7.65 (m, 2H), 7.52-7.46 (m, 1H), 7.46-7.39 (m, 2H), 7.14 (s, 1H), 7.11-7.04 (m, 1H), 7.03-6.96 (m, 1H), 6.84 (dd, J=7.2; 1.4 Hz, 1H), 6.23 (s, 2H), 5.79 (s, 2H), 2.16 (s, 6H), 2.11 (s, 6H), 2.06-2.03 (m, 10H), 1.86 (s, 6H), 1.72 (s, 6H), 1.18 (s, 6H), 1.12 (s, 6H) ppm.

$^{13}$C NMR (CD$_2$Cl$_2$, 125 MHz): δ=280.2, 277.9, 144.0, 140.7, 138.2, 137.9, 137.4, 136.4, 135.8, 135.4, 134.1, 129.7, 129.6, 129.3, 129.2, 127.3, 127.0, 126.6, 126.6, 115.5, 80.9, 56.9, 54.5, 32.3, 32.1, 30.2, 29.5, 21.6, 21.4, 21.0 ppm.

HRMS-ESI calculated for C$_{49}$H$_{60}$N$_2$Cl$_2$Ru [M"]+: 848.3177; found 848.3161.

Elemental analysis: calculated for C$_{49}$H$_{60}$N$_2$Cl$_2$Ru: C 69.32; H 7.12; N 3.30; Cl 8.35; found: C 69.40; H 7.03; N 3.22; Cl 8.56.

Example XXX

Preparation method of intermediate 5g and minor compound 6g from precursor M1 and CAAC salt 3ag.

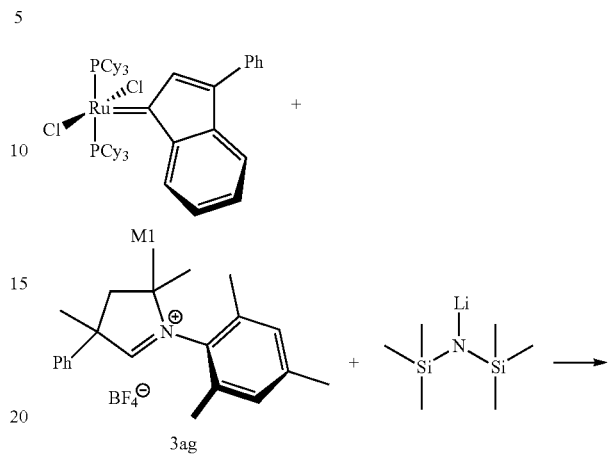

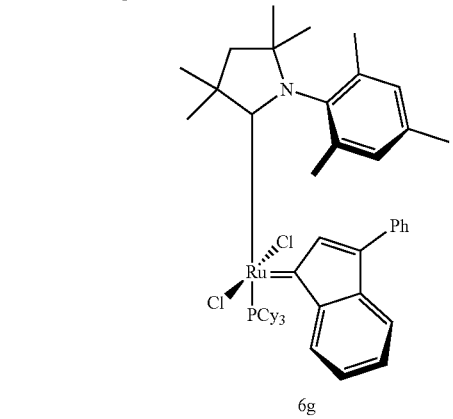

To salt 3ag (1.99 g, 6.0 mmol, 3 molar equivalents) dry deoxygenated toluene (14 ml) was added in argon atmosphere. The mixture was heated to 80° C. and solution of LiHMDS in toluene (1 M, 6.0 ml, 6.0 mmol, 3 molar equivalents) was added. After 1 minute solid complex M1 (1.85 g, 2.0 mmol, 1 molar equivalent) was added. After 30 minutes the mixture was cooled down to the room temperature. Triethylamine (2 ml) was added and filtrated through a short pad of silica gel (deactivated with triethylamine), which was washed with 50 ml toluene/triethylamine mixture (95:5 v/v). Solvents were evaporated under reduced pressure. Crude products 5g and 6g were isolated by column chromatography on silica gel (deactivated with triethylamine; eluent: from cyclohexane/triethylamine (95:5 v/v) to cyclohexane/ethyl acetate/triethylamine (90:5:5 v/v/v)). Two red brown fractions were collected and concentrated to dryness. First fraction residue was dissolved in n-pentane. Solvent was evaporated to 25% of its original amount—precipitate formed during evaporation was filtrated off, washed with a minimal amount of cold n-pentane and dried under high vacuum giving an orange brown crystalline solid—compound 6g (0.270 g, 15%). Second fraction residue was dissolved in n-pentane. Solvent was evaporated to 25% of its original amount—precipitate formed during evaporation was filtrated off, washed with a minimal amount of cold n-pentane and dried under high vacuum giving an orange brown crystalline solid—compound 5g (0.350 g, 21%).

Analytical data for compound 5g obtained in this Example were identical as in Example XXIX. Analytical data for compound 6g:

$^1$H NMR (CD$_2$Cl$_2$, 500 MHz): δ=8.61 (d, J=7.3 Hz, 1H), 7.70 (dd, J=8.2; 1.4 Hz, 2H), 7.54-7.47 (m, 1H), 7.42 (t, J=7.6 Hz, 2H), 7.30 (s, 1H), 7.24-7.18 (m, 1H), 7.17-7.11 (m, 1H), 7.06-7.01 (m, 1H), 6.39 (s, 1H), 6.01 (s, 1H), 2.50-2.38 (m, 3H), 2.31 (s, 3H), 2.17 (s, 3H), 2.14 (d, J=1.8 Hz, 2H), 2.06 (s, 3H), 2.00 (s, 3H), 1.93 (s, 3H), 1.90-1.80 (m, 3H), 1.76-1.54 (m, 12H), 1.53-1.34 (m, 6H), 1.22 (s, 6H), 1.20-1.06 (m, 9H) ppm.

$^{13}$C NMR (CD$_2$Cl$_2$, 125 MHz): δ=287.7, 287.7, 274.7, 274.2, 144.8, 141.4, 138.3, 137.4, 137.3, 137.3, 136.9, 136.5, 136.2, 130.0, 129.9, 129.6, 129.5, 128.1, 128.1, 127.8, 126.8, 116.5, 80.3, 80.3, 57.5, 57.4, 53.5, 53.5, 36.1, 35.6, 32.8, 32.7, 31.9, 31.6, 30.4, 30.1, 29.9, 28.8, 28.6, 28.5, 28.4, 28.3, 27.6, 27.5, 27.2, 27.1, 26.9, 26.9, 26.8, 22.9, 21.7, 21.4, 21.2 ppm.

$^{31}$P NMR (CD$_2$Cl$_2$, 202 MHz): δ=28.7 ppm.

HRMS-ESI calculated for C$_{50}$H$_{68}$NCl$_2$RuP [M]+: 885.3510; found 885.3506.

Elemental analysis: calculated for C$_{50}$H$_{68}$Cl$_2$NPRu: C 67.78; H 7.74; N 1.58; Cl 8.00; found: C 67.84; H 7.67; N 1.47; Cl 7.91.

Example XXXI

Preparation method of intermediate 5h from precursor M10 and CAAC salt 3ah.

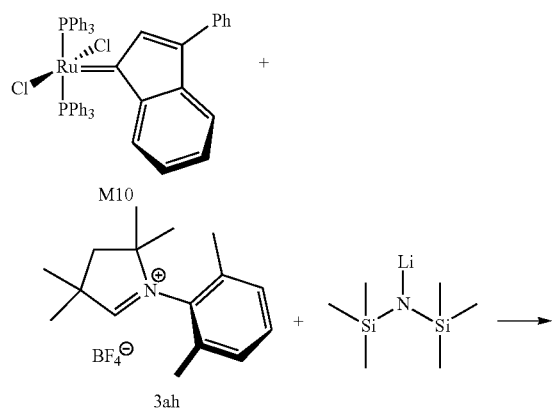

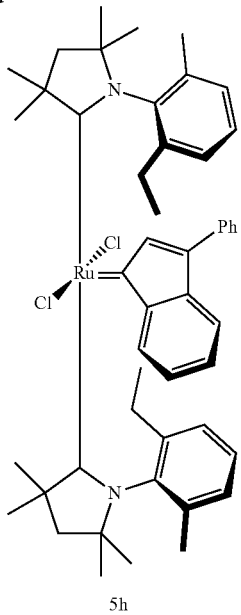

5h

To salt 3ah (1.99 g, 6.0 mmol, 3 molar equivalents) dry deoxygenated toluene (14 ml) was added in argon atmosphere. The mixture was heated to 80° C. and solution of LiHMDS in toluene (1 M, 6.0 ml, 6.0 mmol, 3 molar equivalents) was added. After 1 minute solid complex M10 (1.77 g, 2.0 mmol, 1 molar equivalent) was added. After 2 minutes the mixture was cooled down to the room temperature. The crude product was isolated by column chromatography on silica gel (eluent: cyclohexane/ethyl acetate (9:1 v/v)). Red brown fraction was collected and concentrated to dryness. The residue was dissolved in a small amount of methylene chloride and excess of methanol was added. Methylene chloride was removed under reduced pressure—precipitate formed during evaporation was filtrated off, washed with a minimal amount of cold methanol and dried under high vacuum giving an orange brown crystalline solid—compound 5h (0.589 g, 35%).

$^1$H NMR (C$_6$D$_6$, 500 MHz): δ=9.88-8.08 (m, 1H), 8.02-7.40 (m, 3H), 7.39-7.20 (m, 4H), 7.12-6.85 (m, 3H), 6.75-6.10 (m, 5H), 3.85-2.90 (m, 2H), 2.87-2.67 (m, 1H), 2.66-2.50 (m, 1H), 2.21-2.01 (m, 3H), 1.80-1.15 (m, 7H), 1.14-0.65 (m, 18H) ppm. 2.46-2.22 (m, 12H), 13C NMR (CD$_2$Cl$_2$, 125 MHz): δ=280.4, 280.3, 277.9, 277.8, 277.6, 144.2, 144.1, 141.1, 141.0, 140.9, 139.5, 139.4, 139.1, 139.1, 138.8, 137.9, 137.8, 137.8, 137.4, 135.5, 135.0, 134.6, 134.5, 131.0, 130.5, 129.7, 129.3, 129.2, 129.1, 129.0, 128.7, 128.4, 127.8, 127.7, 127.4, 127.3, 127.0, 126.8, 126.7, 126.6, 126.5, 125.2, 124.3, 116.3, 116.2, 116.1, 81.9, 80.6, 80.5, 61.5, 57.0, 56.9, 56.5, 54.9, 54.8, 54.7, 54.6, 32.7, 32.4, 32.4, 32.0, 31.8, 31.0, 30.2, 29.6, 29.5, 29.1, 28.8, 27.4, 25.2, 25.1, 24.6, 22.1, 21.8, 14.7, 13.1, 12.7 ppm.

HRMS-ESI calculated for C$_{49}$H$_{60}$N$_2$Cl$_2$Ru [M"]+: 848.3177; found 848.3159.

Elemental analysis: calculated for C$_{49}$H$_{60}$N$_2$Cl$_2$Ru: C 69.32; H 7.12; N 3.30; Cl 8.35; found: C 69.15; H 7.30; N 3.48; Cl 8.40.

Example XXXII

Preparation method of intermediate 5i from precursor M10 and CAAC salt 3ai.

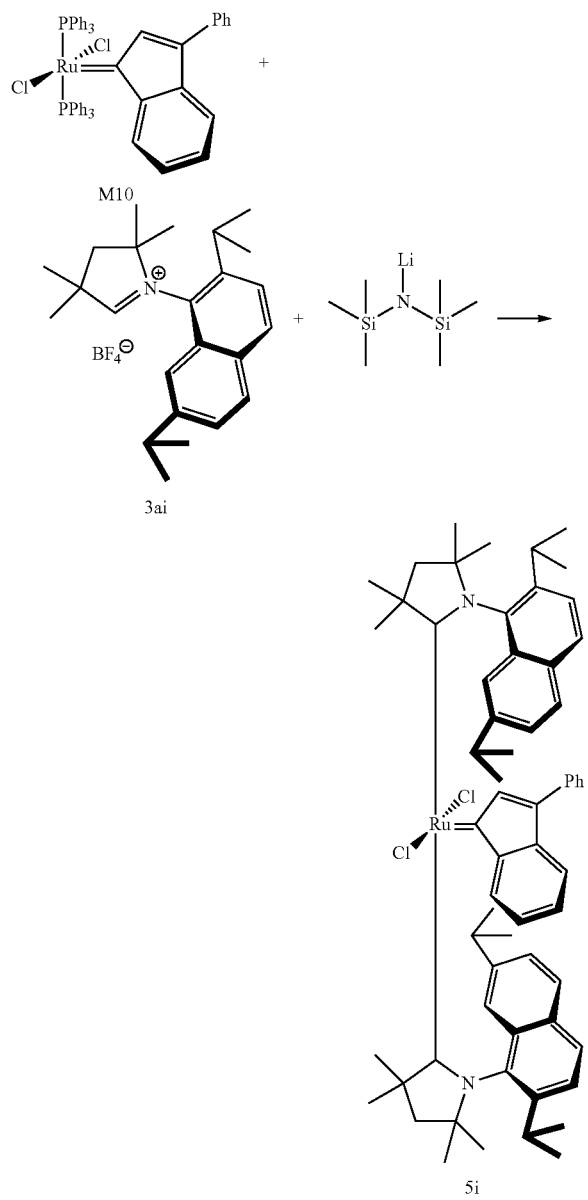

To salt 3ai (0.847 g, 2.0 mmol, 2 molar equivalents) dry deoxygenated toluene (8 ml) was added in argon atmosphere. The mixture was heated to 80° C. and solution of LiHMDS in toluene (1 M, 2.0 ml, 2.0 mmol, 2 molar equivalents) was added. After 1 minute solid complex M10 (0.887 g, 1.0 mmol, 1 molar equivalent) was added. After 2 minutes the mixture was cooled down to the room temperature. Triethylamine (1 ml) was added and filtrated through a short pad of silica gel (deactivated with triethylamine), which was washed with 50 ml toluene/triethylamine mixture (95:5 v/v). Solvents were evaporated under reduced pressure. The crude product was isolated by column chromatography on silica gel (deactivated with triethylamine; eluent: from cyclohexane/triethylamine (95:5 v/v) to cyclohexane/ethyl acetate/triethylamine (90:5:5 v/v/v)). Red brown fraction was collected and concentrated to dryness. The residue was dissolved in n-pentane. Solvent was evaporated to 25% of its original amount—precipitate formed during evaporation was filtrated off, washed with a minimal amount of cold n-pentane and dried under high vacuum giving an orange brown crystalline solid—compound 5i (0.147 g, 14%) as a mixture of isomers (isomer A—major and isomer B -minor). The filtrate was evaporated to dryness. It was dissolved in a small amount of methylene chloride and excess of methanol was added. Methylene chloride was evaporated under reduced pressure -precipitate formed during evaporation was filtrated off, washed with a minimal amount of cold methanol and dried under high vacuum giving red crystalline solid—compound 5i (0.184 g, 18%) as a mixture of isomers (isomer A—minor and isomer B—major).

$^1$H NMR (C$_6$D$_6$, 500 MHz): δ=9.86-8.38 (m, 1H), 8.35-7.65 (m, 6H), 7.62-7.53 (m, 1H), 7.51-7.45 (m, 1H), 7.44-7.37 (m, 1H), 7.35-7.25 (m, 5H), 7.10-6.55 (m, 5H), 4.04-3.72 (m, 1H), 3.45-2.75 (m, 3H), 2.08-1.94 (m, 3H), 1.65-1.05 (m, 35H), 0.98-0.71 (m, 14H) ppm (mixture of isomers).

$^{13}$C NMR (CD$_2$Cl$_2$, 125 MHz): δ=282.3, 281.1, 280.2, 279.0, 278.9, 277.5, 145.9, 145.3, 144.5, 144.5, 144.4, 142.8, 142.4, 141.2, 140.6, 140.2, 138.0, 137.5, 135.0, 134.7, 134.4, 134.4, 134.2, 133.2, 132.8, 132.6, 132.6, 132.5, 132.4, 132.4, 132.2, 131.8, 131.8, 131.4, 131.2, 130.6, 130.5, 129.5, 129.4, 129.2, 129.1, 129.0, 128.9, 128.7, 128.4, 128.0, 127.9, 127.6, 127.5, 127.4, 127.3, 127.2, 127.2, 127.1, 126.9, 126.2, 126.0, 125.7, 125.7, 125.6, 125.4, 125.2, 125.1, 124.7, 123.7, 123.6, 116.1, 115.6, 115.3, 81.5, 81.3, 80.8, 80.1, 62.0, 61.5, 56.5, 56.2, 55.8, 55.3, 54.8, 35.5, 35.4, 35.0, 34.3, 33.2, 32.2, 32.2, 31.6, 31.5, 31.3, 31.3, 30.8, 30.7, 30.6, 30.6, 30.5, 30.5, 30.4, 30.2, 30.1, 30.0, 29.9, 29.7, 29.5, 29.5, 28.9, 28.9, 28.8, 28.7, 28.3, 27.6, 27.5, 27.3, 26.8, 26.2, 26.0, 25.7, 25.7, 25.4, 24.9, 24.8, 24.7, 24.6, 24.5, 24.4, 24.3, 24.2, 23.8, 23.3, 23.2, 23.1, 23.1, 23.0, 22.9, 22.5 ppm.

Analytical Data for Isomer A-Enriched Mixture:
HRMS-ESI calculated for C$_{63}$H$_{16}$N$_2$Cl$_2$Ru [M,]+: 1032.4429; found 1032.4402.
Elemental analysis: calculated for C$_{63}$H$_{16}$N$_2$Cl$_2$Ru:
C 73.23; H 7.41; N 2.71; Cl 6.86; found: C 73.19; H 7.46; N 2.60; Cl 6.84.

Analytical Data for Isomer B-Enriched Mixture:
HRMS-ESI calculated for C63H16N2Cl2Ru [M,]+: 1032.4429; found 1032.4426.
Elemental analysis: calculated for C63H16N2Cl2Ru:
C 73.23; H 7.41; N 2.71; Cl 6.86; found: C 73.16; H 7.31; N 2.74; Cl 6.97.

Example XXXIII

Preparation method of intermediate 5j from precursor Gru-1 and CAAC salt 3ab.

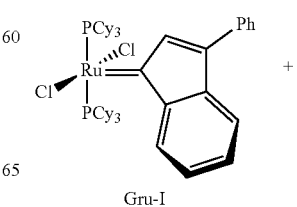

Gru-I

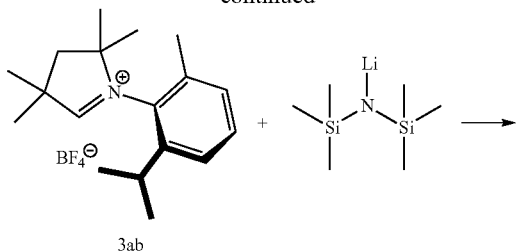

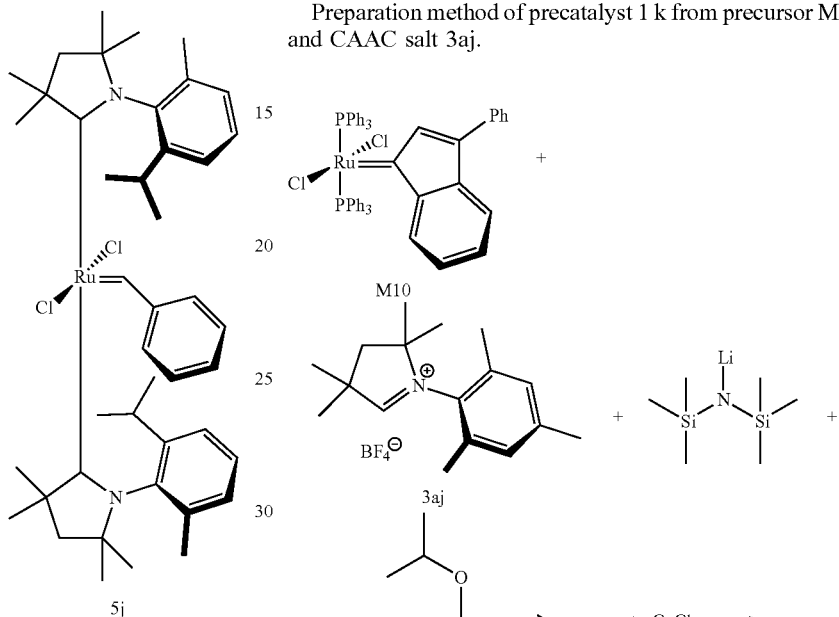

To salt 3ab (1.04 g, 3.0 mmol, 3 molar equivalents) dry deoxygenated toluene (7 ml) was added in argon atmosphere. The mixture was heated to 80° C. and solution of LiHMDS in toluene (1 M, 3.0 ml, 3.0 mmol, 3 molar equivalents) was added. After 1 minute solid complex Gru-1 (0.823 g, 1.0 mmol, 1 molar equivalent) was added. After 2 minutes the mixture was cooled down to the room temperature. Triethylamine (1 ml) was added and filtrated through a short pad of silica gel (deactivated with triethylamine), which was washed with 25 ml toluene/triethylamine mixture (95:5 v/v). Solvents were evaporated under reduced pressure. The crude product was isolated by column chromatography on silica gel (deactivated with triethylamine; eluent: from cyclohexane/triethylamine (95:5 v/v) to cyclohexane/ethyl acetate/triethylamine (90:5:5 v/v/v)). Brown fraction was collected and concentrated to dryness. The residue was dissolved in n-pentane. Solvent was evaporated to 25% of its original amount—precipitate formed during evaporation was filtrated off, washed with a minimal amount of cold n-pentane and dried under high vacuum giving dark brown crystalline solid -compound 5j (0.441 g, 57%).

$^1$H NMR (C$_5$D$_6$, 500 MHz): δ=18.29 (s, 1H), 9.41 (d, J=8.1 Hz, 1H), 7.12-7.07 (m, 1H), 7.01-6.95 (m, 1H), 6.84 (dd, J=7.9; 1.6 Hz, 2H), 6.67 (td, J=7.6; 1.5 Hz, 1H), 6.42 (t, J=7.7 Hz, 2H), 6.22 (d, J=7.9 Hz, 1H), 5.93 (dd, J=7.5; 1.6 Hz, 2H), 3.23 (hept, J=6.4 Hz, 2H), 2.31 (d, J=4.1 Hz, 12H), 2.21 (s, 6H), 1.74-1.60 (m, 1 OH), 1.18 (s, 6H), 1.11 (d, J=6.6 Hz, 6H), 0.73 (s, 6H) ppm (main isomer).

$^{13}$C NMR (CD$_2$Cl$_2$, 125 MHz): δ=285.0, 284.9, 281.5, 149.4, 145.3, 139.1, 136.8, 131.9, 130.9, 129.1, 128.3, 127.6, 127.5, 127.3, 124.5, 79.3, 56.5, 55.2, 32.8, 31.8, 31.1, 29.8, 28.9, 28.5, 28.4, 28.3, 26.8, 22.2 ppm.

HRMS-ESI calculated for C$_{43}$H$_{60}$N$_2$Cl$_2$Ru [MY: 776.3177; found 776.3140.

Elemental analysis: calculated for C$_{43}$H$_{60}$N$_2$C$_{12}$Ru:
C 66.47; H 7.78; N 3.61; Cl 9.13; found: C 66.24; H 7.75; N 3.46; Cl 9.01.

Example XXXIV

Preparation method of precatalyst 1k from precursor M10 and CAAC salt 3aj.

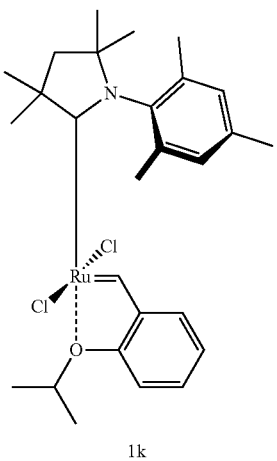

To salt 3aj (0.331 g, 1.0 mmol, 2 molar equivalents) dry deoxygenated toluene (4 ml) was added in argon atmosphere. The mixture was heated to 80° C. and solution of LiHMDS in toluene (1 M, 1.0 ml, 1.0 mmol, 2 molar equivalents) was added. After 1 minute solid complex M10 (0.443 g, 0.5 mmol, 1 molar equivalent) was added. After 2 minutes the mixture was cooled down to 60° C. Benzylidene ligand 4a (0.106 g, 0.6 mmol, 1.2 molar equivalents) and CuCl (0.173 g, 1.75 mmol, 3.5 molar equivalents) were added. The whole was stirred for 20 minutes at 60° C. and cooled down to the room temperature. The crude product was isolated by column chromatography on silica gel (eluent: toluene). Green fraction was collected and concentrated to dryness. The residue was dissolved in ethyl acetate and filtrated. The solvent was evaporated, the residue was washed with isopropanol and dried under high vacuum giving green crystalline solid—precatalyst 1 k (0.112 g, 40%).

$^1$H NMR (CD$_2$Cl$_2$, 500 MHz): δ=16.22 (s, 1H), 7.61 (ddd, J=8.2; 7.1; 2.0 Hz, 1H), 7.15 (s, 2H), 7.01-6.89 (m, 3H), 5.16 (hept, J=6.2 Hz, 1H), 2.48 (s, 3H), 2.20 (s, 8H), 2.07 (s, 6H), 1.71 (d, J=6.1 Hz, 6H), 1.41 (s, 6H) ppm.

$^{13}$C NMR (CD$_2$Cl$_2$, 125 MHz): δ=298.3, 298.1, 266.5, 152.6, 144.9, 139.2, 138.6, 138.2, 131.2, 131.0, 130.9, 123.8, 122.6, 113.6, 79.2, 75.5, 56.5, 52.5, 29.7, 29.3, 22.3, 21.3, 20.9 ppm.

HRMS-ESI calculated for C$_{21}$H$_{31}$NONaCl$_2$Ru [M+Na]+: 586.1193; found 586.1185.

Elemental analysis: calculated for C$_{21}$H$_{31}$NOCl$_2$Ru:

C 57.54; H 6.62; N 2.49; Cl 12.58; found: C 57.51; H 6.62; N 2.39; Cl 12.68.

Example XXXV

Preparation method of precatalyst 11 from precursor M10 and CAAC salt 3ai.

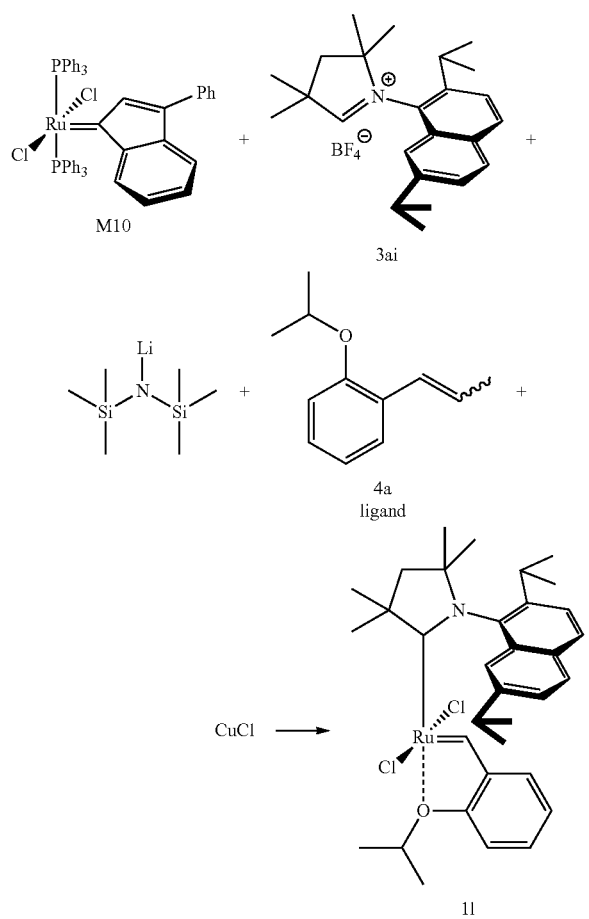

To salt 3ai (1.27 g, 2.0 mmol, 2 molar equivalents) dry deoxygenated toluene (12 ml) was added in argon atmosphere. The mixture was heated to 80° C. and solution of LiHMDS in toluene (1 M, 3.0 ml, 3.0 mmol, 2 molar equivalents) was added. After 1 minute solid complex M10 (1.33 g, 1.0 mmol, 1 molar equivalent) was added. After 2 minutes the mixture was cooled down to 60° C. Benzylidene ligand 4a (0.317 g, 1.8 mmol, 1.2 molar equivalents) and CuCl (0.520 g, 5.25 mmol, 3.5 molar equivalents) were added. The whole was stirred for 10 minutes at 60° C. and cooled down to the room temperature. The crude product was isolated by column chromatography on silica gel (eluent: toluene). Green fraction was collected and concentrated to dryness. The residue was dissolved in ethyl acetate and filtrated. The solvent was evaporated, the residue was washed with isopropanol and dried under high vacuum giving green crystalline solid—precatalyst 11 (0.517 g, 53%).

$^1$H NMR (CD$_2$Cl$_2$, 500 MHz): δ=15.98 (s, 1H), 8.11 (d, J=8.7 Hz, 1H), 7.87-7.84 (m, 1H), 7.81 (d, J=8.4 Hz, 1H), 7.68 (d, J=8.7 Hz, 1H), 7.47 (ddd, J=8.3; 7.4; 1.7 Hz, 1H), 7.35 (dd, J=8.5; 1.7 Hz, 1H), 6.90 (d, J=8.3 Hz, 1H), 6.76 (td, J=7.5; 0.9 Hz, 1H), 6.52 (dd, J=7.6; 1.7 Hz, 1H), 5.12 (hept, J=6.1 Hz, 1H), 3.23 (hept, J=6.6 Hz, 1H), 2.97 (hept, J=6.9 Hz, 1H), 2.38-2.33 (m, 4H), 2.29-2.25 (m, 1H), 2.05 (s, 3H), 1.76 (d, J=6.1 Hz, 3H), 1.66 (d, J=6.1 Hz, 3H), 1.45 (s, 3H), 1.39 (d, J=6.7 Hz, 3H), 1.20 (d, J=6.9 Hz, 6H), 1.17 (s, 3H), 0.80 (d, J=6.5 Hz, 3H) ppm.

$^{13}$C NMR (CD$_2$Cl$_2$, 125 MHz): δ=296.2, 296.0, 268.5, 152.8, 146.6, 145.4, 143.8, 134.6, 132.1, 131.7, 131.0, 130.1, 127.6, 126.6, 124.4, 124.1, 123.6, 122.3, 113.4, 79.0, 75.5, 56.7, 52.7, 34.8, 31.0, 30.2, 29.6, 29.4, 29.2, 25.4, 24.4, 23.8, 23.4, 22.4, 22.3 ppm.

HRMS-ESI calculated for C34H4sNOKCl2Ru [M+K]+: 694.1559; found 694.1552.

Elemental analysis: calculated for C34H4sNOCl2Ru:

C 62.28; H 6.92; N 2.14; Cl 10.81; found: C 62.25; H 6.88; N 1.98; Cl 10.76.

Example XXXVI

Application of precatalysts 5a-5i in ring-closing metathesis (RCM) reactions of diethyl diallylomalonate S1 leading to a cyclic compound P1.

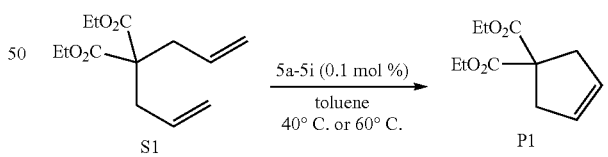

To the solution of diethyl diallylomalonate S1 (480.6 mg, 2.0 mmol) in dry deoxygenated toluene (20 ml) at 40'C or 60'C a solution of respective precatalyst 5a-5i (0.002 mmol, 0.1 mol %) in dry deoxygenated toluene (50 μl) was added. The whole was stirred in argon atmosphere. At certain time intervals 0.1 ml samples of reaction mixture were collected to which one drop of ethyl vinyl ether was added to deactivate the catalyst. Conversion of substrate was determined by gas chromatography. A summary is presented in Table 4 (40'C) and Table 5 (60'C).

TABLE 4

DEDAM conversion as a function of time for a reaction conducted at 40°C.

| T = 40° C. | | | Conversion(%) | | | | | |
|---|---|---|---|---|---|---|---|---|
| Time (min) | 5a | 5c | 5d | 5h | 5e | 5g | 5f | 5i | 1d |
| 2 | — | 14 | 3 | — | 2 | — | | — | 6 |
| 4 | — | 25 | 6 | — | 7 | — | | — | 22 |
| 6 | — | 37 | 9 | — | 14 | — | | 8 | 42 |
| 8 | — | 49 | 12 | — | 21 | — | | — | 60 |
| 10 | — | 60 | 15 | 0.2 | 30 | 0.7 | 3 | 13 | 73 |
| 15 | — | 81 | 24 | — | 48 | — | | — | 90 |
| 20 | — | 92 | 32 | — | 63 | — | | 27 | 95 |
| 30 | 0.6 | 99 | 49 | — | 86 | 4 | 9 | 41 | 98 |
| 60 | 1 | 99.6 | 86 | 0.6 | 99 | 8 | 19 | 68 | 99.2 |
| 120 | 1.8 | — | 99 | 1.2 | — | 12 | 37 | 90 | — |
| 180 | 3 | — | — | — | — | 18 | 52 | 96 | — |

TABLE 5

DEDAM conversion as a function of time for reaction conducted at 60 T = 60° C.

| T = 60° C. | | Conversion (%) | | |
|---|---|---|---|---|
| Time (min) | 5h | 5g | 5f | 5i |
| 2 | — | — | 10 | 36 |
| 4 | — | — | 21 | 69 |
| 6 | — | 4 | | 85 |
| 8 | — | — | 44 | 93 |
| 10 | 1 | 5 | 54 | 97 |
| 15 | — | — | 74 | 99 |
| 20 | 3 | — | 86 | 99.6 |
| 30 | 6 | 7 | 96 | 99.7 |
| 60 | 22 | 10 | 99.6 | 99.8 |
| 120 | 63 | 20 | — | — |
| 180 | 89 | 38 | — | — |

Example XXXVII

Application of precatalysts 5c-5i in ethenolysis reactions of methyl oleate (MO).

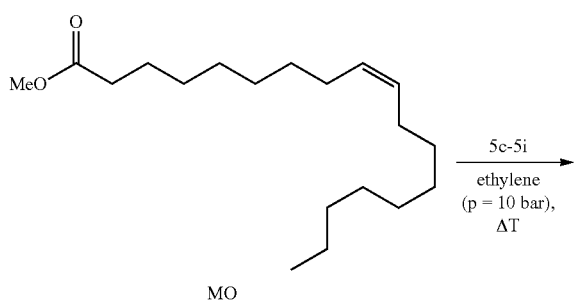

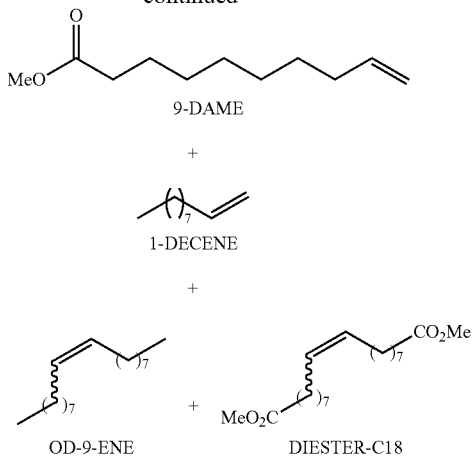

To degassed MO (35.0 g, 118 mmol) a catalyst (10 ppm or 5 ppm) solution in dry deoxygenated toluene (100 µl) was added. The mixture was vacuum-pumped to an autoclave and stirred for 5 hours in a suitable temperature at 10 bar of ethylene. After 5 hours the reaction was quenched and after removal of ethylene from the reactor to the reaction mixture 0.1 ml 0.1 M SnatchCat solution [CAS: 51641-96-4] in methylene chloride was added to deactivate the catalyst. The samples were diluted with methylene chloride and analysed by gas chromatography. The conversions were calculated using residual methyl stearate as an internal standard. The results were summarised in Table 6.

In order to determine the FID detector response factors to individual components of the reaction mixture a mixture of substrate—methyl oleate (MO), desired reaction products: 1-DECENE and 9-DAME, and reaction by-products OD-9-ENE and DIE5TER-C18 diester according to the table below was prepared. The resulting mixture was diluted with toluene to 10 ml and analysed by gas chromatography. The area under the peak (AUP) for each component (mean of seven injections) was divided by the component mass of the analytical sample taking into account its purity and obtaining absolute response factor of a given component Rf. Assuming the response factor of methyl oleate (MO) equal to Rf=1, from the proportions the absolute response factors Rf for remaining components were calculated.

TABLE 6

| Component | Analytical sample mass [mg] | Purity according to GC [%] | Area under the peak AUP [µVxs] | Absolute response factor Rf = AUP/ (mxpurity) | Response factor for MO Rf |
|---|---|---|---|---|---|
| 1-DECENE | 23.91 | 99.9 | 101514.2 | 4249.9 | 0.63 |
| 9-DAME | 28.74 | 98.0 | 112831.5 | 4006.1 | 0.60 |
| OD-9-ENE | 20.65 | 98.0 | 145112.4 | 7170.6 | 1.07 |
| MO | 18.74 | 96.3 | 121077.7 | 6709.2 | 1.00 |
| D1ESTER-C18 | 19.75 | 97.4 | 102791.4 | 5343.6 | 0.80 |

In the further calculations, the area under the peak of a given component on the chromatogram was converted into percentage in the mixture using response factors calculated above.

Reaction selectivity (S) was determined from the formula:

$$S = 100 \times (n1\text{-DECENE} + ns\text{-DAME}) / [(n1\text{-DECENE} + ns\text{-DAME}) + 2 \times (n0D\text{-}9\text{-}ENE + no1ESTER\text{-}C18)],$$

where
n is the number of moles

Reaction yield (Y) was determined from the formula:

Y=Conversion×Selectivity/100

TON=Reaction yield/catalyst amount in ppm×10000.

TABLE 7

Methyl oleate (MO) ethenolysis with 5c-5i and 1d precatalysts application.

| Pre-catalyst | Pre-catalyst amount (ppm) | T (° C.) | Con-version (%) | 9-DAME content in the mixture | Selectivity (%) | Yield (%) | TON |
|---|---|---|---|---|---|---|---|
| 5c | 10 | 50 | 59 | 34 | 89 | 53 | 52782 |
| 5c | 5 | 50 | 41 | 28 | 91 | | 73855 |
| 5d | 10 | 60 | 53 | 31 | 89 | 47 | 46876 |
| 5e | 10 | 50 | 70 | 40 | 88 | 61 | 61361 |
| 5e | 5 | 60 | 48 | 31 | 90 | 43 | 86025 |
| 5f | 10 | 60 | 21 | 16 | 92 | 19 | 18930 |
| 5i | 10 | 65 | 55 | 34 | 87 | 48 | 47638 |
| 1d | 10 | 40 | 61 | 34 | 91 | 56 | 56091 |
| 1d | 5 | 40 | 51 | | 92 | 46 | 92505 |

Example XXXVIII

Application of precatalyst 5c in ring-closing metathesis (RCM) reaction of diallyl tosylamide S2 leading to a cyclic compound P2.

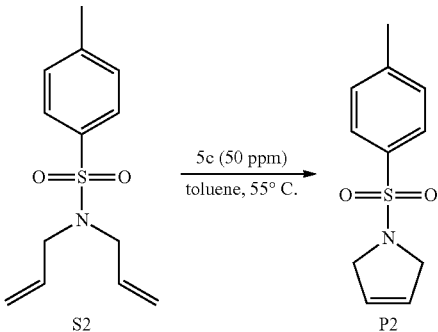

To solution of diallyl tosylamide S2 (205.0 mg, 0.816 mmol) in dry deoxygenated toluene (3 ml) at 55° C. a solution of precatalyst 5c (0.041 mg, 0.041 μmol, 50 ppm) in dry deoxygenated toluene (50 μl) was added. The whole was stirred in argon atmosphere. After 20 minutes a 0.1 ml sample of reaction mixture was collected to which a drop of 0.1 M SnatchCat solution was added to deactivate the catalyst. Conversion of substrate determined by gas chromatography was above 99.5%.

Example XXXIX

Application of precatalyst 5c in ring-closing metathesis (RCM) reaction of compound S3 leading to a cyclic compound P3.

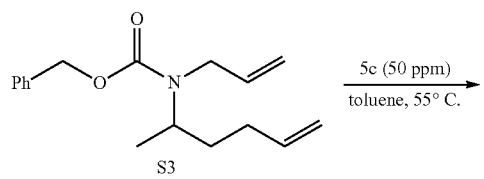

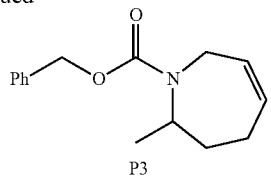

To solution of compound S3 (212.0 mg, 0.776 mmol) in dry deoxygenated toluene (3 ml) at SS° C. solution of precatalyst 5c (0.039 mg, 0.039 μmol, 50 ppm) in dry deoxygenated toluene (50 μl) was added. The whole was stirred in argon atmosphere. After 1 hour a 0.1 ml sample of reaction mixture was collected to which a drop of 0.1 M SnatchCat solution was added to deactivate the catalyst. Conversion of substrate determined by gas chromatography was above 99.5%. No by-products were observed.

$^1$H NMR (CDCl$_3$, 500 MHz): δ=7.39-7.27 (m, SH), 5.74-5.62 (m, 2H), 5.19-5.10 (m, 2H), 4.46-4.06 (m, 2H), 3.64-3.56 (m, 1H), 2.26-2.08 (m, 2H), 1.93-1.67 (m, 2H), 1.15 (dd, J=6.4; 4.5 Hz, 3H) ppm.

$^{13}$C NMR (CDCl$_3$, 125 MHz): δ=156.04, 155.96, 137.2, 137.1, 131.7, 131.4, 128.4, 128.3, 127.8, 127.7, 127.6, 127.4, 66.9, 66.7, 52.5, 52.3, 39.4, 39.1, 34.0, 33.9, 27.1, 26.9, 19.6, 19.1 ppm.

Example XXXX

Application of precatalyst 5c in homometathesis reaction of 9-decenoic acid methyl ester 9-DAME leading to compound DIESTER-C18.

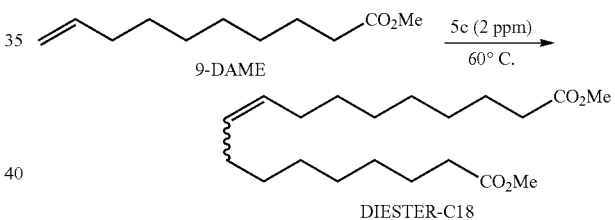

To 9-decenoic acid methyl ester 9-DAME (5.53 g, 30.0 mmol) at 60° C. a solution of precatalyst 5c (0.060 mg, 0.060 μmol, 2 ppm) in dry deoxygenated toluene (50 μl) was added. The whole was stirred in argon atmosphere (argon was bubbled through the reaction mixture). After 2 hours the reaction mixture was cooled to the ambient temperature, 5 drops of 0.1 M SnatchCat solution were added and reaction mixture was stirred for the next 30 minutes.

Figure 2:
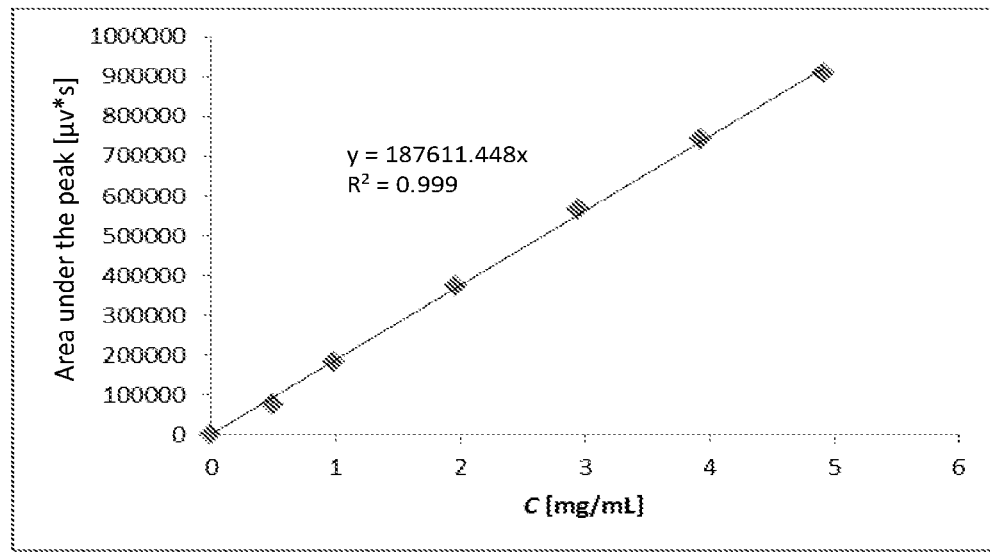
FIG. 2 shows graphs depicting relationship between area under the peak (AUP) on the chromatogram and the concentration (mg/ml) of the analysed compound for reaction of the Example XXXX.
Figure 2:
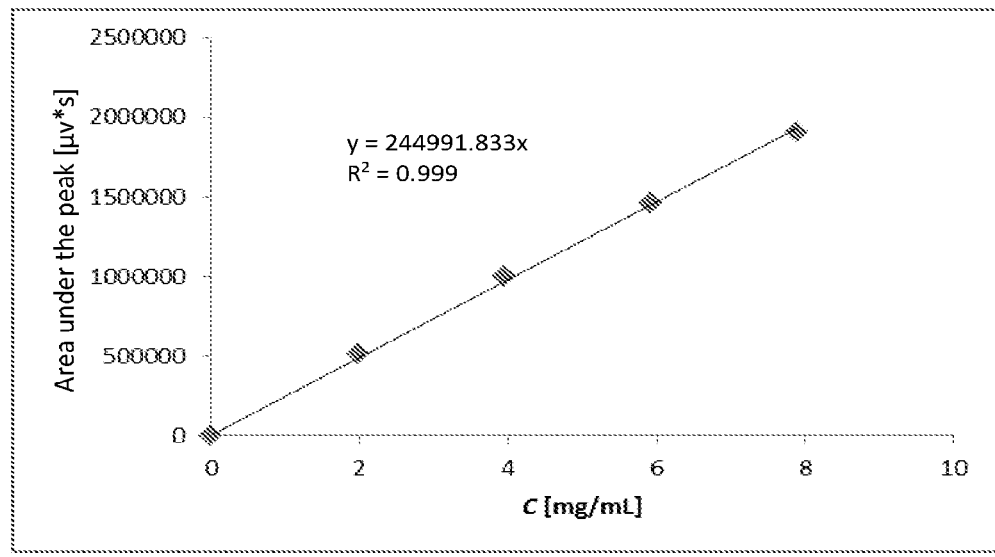

In order to plot standard curves two analytical samples of substrate and product, respectively, were prepared. Analytical samples were diluted to obtain respective standard solution concentrations. Graphs depicting relationship between area under the peak (AUP) on the chromatogram and the concentration (mg/ml) of the analysed compound were shown in the FIG. 2.

28.70 mg of the analytical sample of the post-reaction mixture was prepared and diluted to 10 ml (2.87 mg/ml).

On the chromatogram of such obtained solution AUP for the substrate was 166469.8 μVxs (mean of three injections) and AUP for product was 47666.1 μVxs (mean of three injections), what corresponded to the substrate concentration of 0.89 mg/ml (based on the substrate standard curve) and product concentration of 1.95 mg/ml (based on the product standard curve).

Conversion and yield were determined from the formulas:

Conversion=100%×(1−(0.89/2.87))=68.99%

Yield=100%×1.95/2.87=67.94%.

Selectivity=100%×Yield/Conversion=98.48%.

TON=169850.

A mixture of Ea isomers (1.5:1).

$^1$H NMR (CDCl$_3$, 500 MHz): δ=5.36 (ddd, J=5.3; 3.7; 1.6 Hz, 2H, E), 5.32 (ddd, J=5.7; 4.3; 1.1 Hz, 2H, Z), 3.65 (s, 6H), 2.29 (t, J=7.5 Hz, 4H), 2.03-1.90 (m, 4H), 1.68-1.56 (m, 4H), 1.35-1.23 (m, 16H) ppm.

$^{13}$C NMR (CDCl$_3$, 125 MHz): δ=174.25 (E), 174.24 (Z), 130.3 (E), 129.8 (Z), 51.4, 34.1, 32.5, 29.6 (Z), 29.5 (E), 29.12 (Z), 29.08 (E), 29.07 (E), 29.05 (Z), 28.9, 27.1 (Z), 24.9 (E) ppm.

Example XXXXI

Application of precatalyst 5c in homometathesis reaction of 1-DECENE leading to octadec-9-ene E.

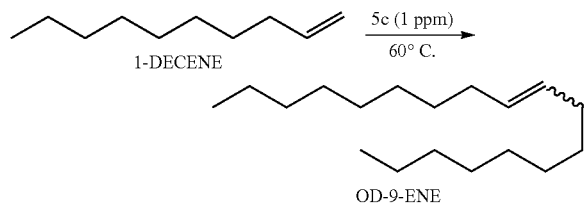

Figure 3:
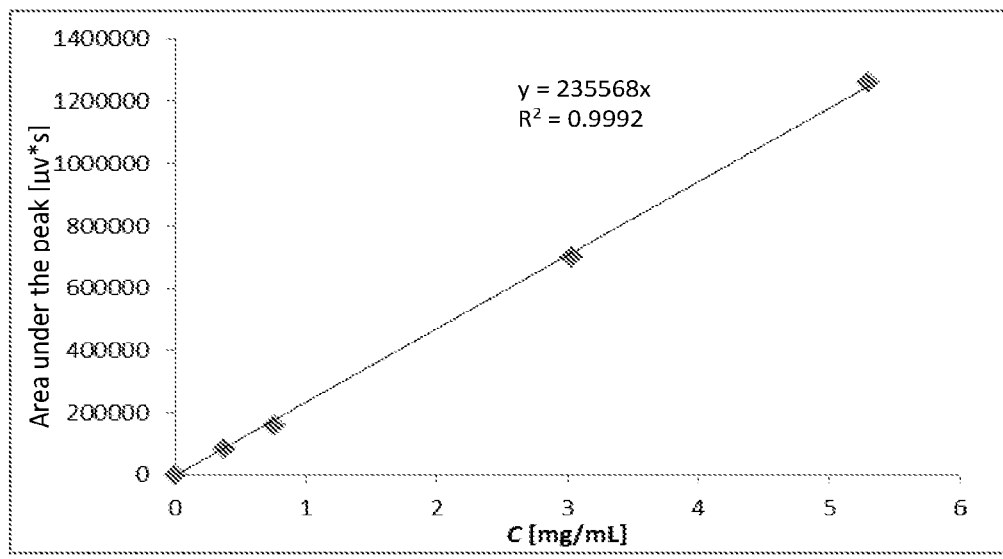
FIG. 3 shows graphs depicting relationship between area under the peak (AUP) on the chromatogram and the concentration (mg/ml) of the analysed compound for reaction of the Example XXXXI.
Figure 3:
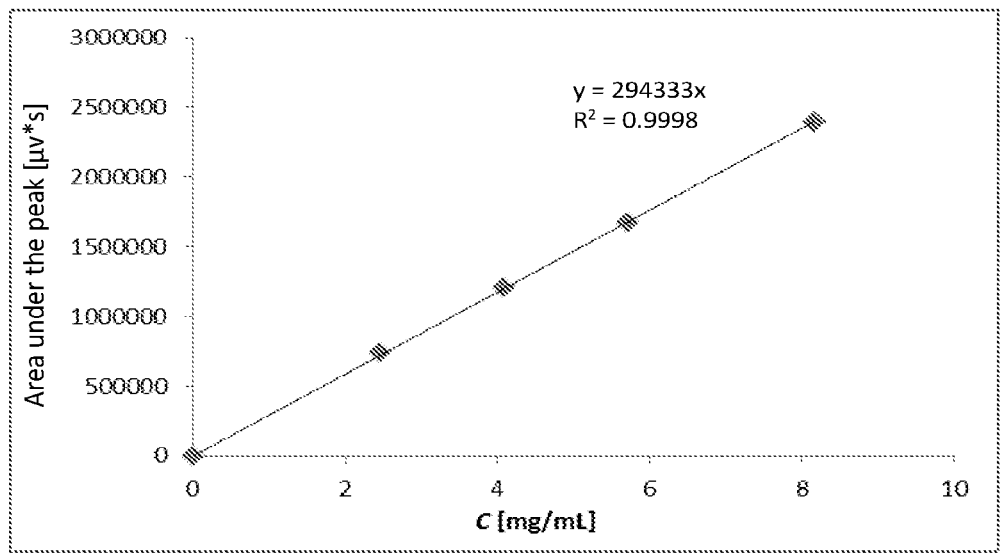

To 1-DECENE (5.22 g, 37.2 mmol) at 60° C. a solution of precatalyst 5c (0.037 mg, 0.037 µmol, 1 ppm) in dry deoxygenated toluene (S0 µl) was added. The whole was stirred in argon atmosphere (argon was bubbled through the reaction mixture). After 2 hours the reaction mixture was cooled to the ambient temperature, 5 drops of 0.1 M Snatch-Cat solution were added and it was stirred for the next 30 minutes. Then two solutions of reaction mixture with known concentration were prepared separately. Conversion (64%) and yield (63%) were determined by gas chromatography using external standard method (calculations are performed analogously to those shown in Example XXXX). Graphs depicting relationship between area under the peak (AUP) on the chromatogram and the concentration (mg/ml) of the analysed compound were shown in the FIG. 3. Reaction selectivity 98%. TON was 316398.

A mixture of E/Z isomers (4:1).

$^1$H NMR (CDCl$_3$, 500 MHz): δ=5.39 (ddd, J=5.3; 3.7; 1.6 Hz, 2H, E), 5.35 (ddd, J=5.7; 4.4; 1.1 Hz, 2H, Z), 2.06-1.91 (m, 4H), 1.38-1.18 (m, 24H), 0, 88 (t, J=6.9 Hz, 6H) ppm.

$^{13}$C NMR (CDCl$_3$, 125 MHz): δ=130.4 (E), 129.9 (Z), 32.6, 31.9, 29.8 (Z), 29.7 (E), 29.53 (Z), 29.51 (E), 29.3, 29.2 (E), 27.2 (Z), 22.7, 14.1 ppm.

Example XXXXII

Application of precatalyst 5c in cross-metathesis reaction of 9-decenoic acid methyl ester 9-DAME with acrylonitrile 56 leading to compound PG.

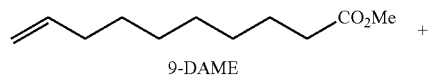

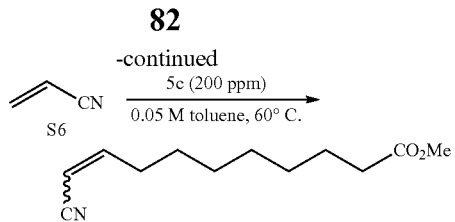

To solution of 9-decenoic acid methyl ester 9-DAME (184.0 mg, 1.0 mmol) in dry deoxygenated toluene (20 ml) acrylonitrile 56 (99 NI, 1.50 mmol, 1.5 molar equivalents) and methyl stearate (10 mg, internal standard) were added at 60° C., following by a solution of precatalyst 5c (0.1 mg, 0.1 Nmol, 100 ppm) in dry deoxygenated toluene (SO NI). Reaction mixture was stirred in argon atmosphere. After 1 hour and then after 2 hours further portions of precatalyst 5c (2×0.05 mg, 0.05 Nmol, SO ppm) in dry deoxygenated toluene (SO NI) were added. Totally 0.2 mg, 0.2 Nmol, 200 ppm precatalyst 5c was used. After another hour 0.1 ml reaction mixture sample was collected to which a drop of 0.1 M SnatchCat solution was added to deactivate the catalyst. Conversion of substrate determined by gas chromatography with internal standard was 87%. Content of the PG product on the chromatogram was 75%.

A mixture of E/Z isomers (1:4).

$^1$H NMR (CDCl$_3$, 500 MHz): δ=6.69 (dt, J=16.4; 7.0 Hz, 1H, E), 6.46 (dt, J=10.9; 7.7 Hz, 1H, Z), 5.30 (dt, J=16.4; 1.7 Hz, 1H, E), 5.29 (dt, J=10.9; 1.3 Hz, 1H, Z), 3.65 (s, 3H, E+3H, Z), 2.40 (dq, J=7.6; 1.3 Hz, 2H, Z), 2.29 (t, J=7.5 Hz, 2H, E+2H, Z), 2.20 (qd, J=7.1; 1.7 Hz 2H, E), 1.64-1.54 (m, 2H, E+2H, Z), 1.50-1.39 (m, 2H, E+2H, Z), 1.36-1.26 (m, 6H, E+6H, Z) ppm.

$^{13}$C NMR (CDCl$_3$, 125 MHz): δ=174.12 (Z), 174.08 (E), 156.0 (E), 155.0 (Z), 117.5 (E), 116.0 (Z), 99.6-33.95 (Z), 33.92 (E), 33.2 (E) 31.7 (Z), 28.87 (Z), 28.85 (E), 28.83 27.5 (E), 24.77 (Z), 24.75 (E) ppm.

Example XXXXIII

Application of precatalyst 5c in cross-metathesis reaction of 9-decenoic acid methyl ester 9-DAME with methyl acrylate 57 leading to compound P7.

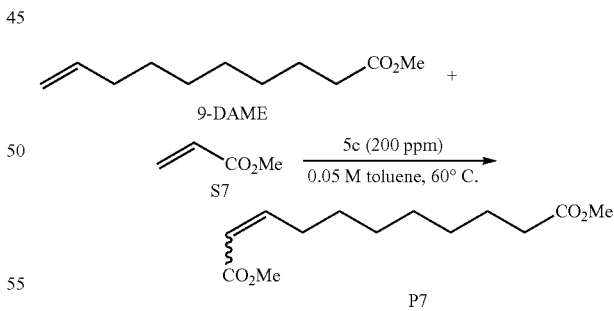

To solution of 9-decenoic acid methyl ester 9-DAME (400.0 mg, 2.17 mmol) in dry deoxygenated toluene (4 ml) methyl acrylate 57 (0.98 ml, 10.9 mmol, 5 molar equivalents), methyl stearate (20 mg, internal standard) were added at 60° C., following by a solution of precatalyst 5c (0.109 mg, 0.109 Nmol, SO ppm) in dry deoxygenated toluene (SO NI). The whole was stirred in argon atmosphere. After 1 hour, 2 hours and 3 hours further portions of precatalyst 5c (3×0.109 mg, 0.109 Nmol, SO ppm) in dry deoxygenated toluene (SO NI) were added. Totally 0.436 mg, 0.436 Nmol, 200 ppm of precatalyst 5c was used. After another hour 0.1 ml reaction mixture sample was collected to which a drop of 0.1 M SnatchCat solution was added to deactivate the catalyst. Conversion of substrate determined by gas chromatography with an internal standard was 99%. Content of product P7 in postreaction mixture was 97%.

A mixture of E/Z isomers (87:13).

Isomer E:

$^1$H NMR (CDCl$_3$ 500 MHz): δ=6.94 (dt, J=15.7; 7.0 Hz, 1H), 5.80 (dt, J=15.6; 1.6 Hz, 1H), 3.71 (s, 3H), 3.65 (s, 3H), 2.28 (t, J=7.5 Hz, 2H), 2.17 (dq, J=7.1; 1.6 Hz, 2H), 1.64-1.56 (m, 2H), 1.47-1.39 (m, 2H), 1.33-1.26 (m, 6H) ppm.

$^{13}$C NMR (CDCl$_3$, 125 MHz): δ=174.2, 167.1, 149.6, 133.4, 120.8, 51.4, 51.3, 34.0, 32.1, 29.0, 28.9, 27.9, 24.8 ppm.

Isomer Z:

$^1$H NMR (CDCl$_3$, 500 MHz): δ=6.22 (dt, J=11.6; 7.5 Hz, 1H), 5.76 (dt, J=11.5; 1.7 Hz, 1H), 3.70 (s, 3H), 3.66 (s, 3H), 2.64 (dq, J=7.5; 1.7 Hz, 2H), 2.30 (t, J=7.5 Hz, 2H), 1.65-1.56 (m, 2H), 1.47-1.39 (m, 2H), 1.34-1.28 (m, 6H) ppm.

$^{13}$C NMR (CDCl$_3$, 125 MHz): δ=174.3, 166.8, 150.8, 119.2, 51.4, 51.0, 34.1, 29.1, 29.0, 28.9, 24.9, 24.8 ppm.

Example XXXXIV

Application of precatalyst 5c in ring-closing metathesis reaction of 58 leading to compound PS having a tetrasubstituted double bond.

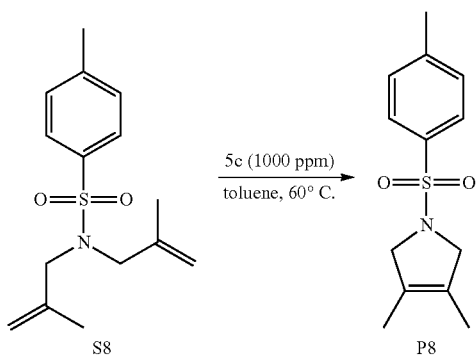

To solution of compound S8 (509.0 mg, 1.82 mmol) in dry deoxygenated toluene (6.8 ml) at 60° C., in argon atmosphere every 10 minutes a solution of precatalyst 5c (0.182 mg, 0.182 μmol, 100 ppm) in dry deoxygenated toluene (50 μl) was added up to a total amount of 1000 ppm of precatalyst 5c (10 portions). The whole was stirred in argon atmosphere for an additional hour. 0.1 ml of the reaction mixture sample was collected to which a drop of 0.1 M SnatchCat solution was added to deactivate the catalyst. Conversion of substrate determined by gas chromatography was 90%. The product was isolated by column chromatography on silica gel. White solid, 361 mg (79%).

$^1$H NMR (CDCl$_3$, 500 MHz): δ=7.70 (d, J=8.2 Hz, 2H), 7.30 (d, J=8.0 Hz, 2H), 3.96 (s, 4H), 2.41 (s, 3H), 1.53 (s, 6H) ppm.

13C NMR (CDCl$_3$, 125 MHz): δ=143.2, 134.2, 129.6, 127.4, 126.1, 58.7, 21.4, 11.0 ppm.

Example XXXXV

Application of precatalyst 5c in homometathesis reaction of methyl oleate MO leading to OD-9-ENE and DIESTER-C18 compounds.

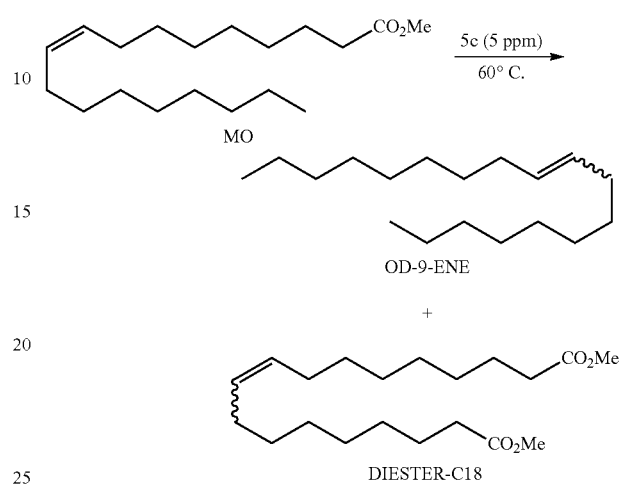

To methyl oleate MO (19.52 g, 65.9 mmol) at 60° C. in argon atmosphere every 30 minutes a solution of precatalyst 5c (0.066 mg, 0.066 μmol, 1 ppm) in dry deoxygenated toluene (SO μl) was added, up to 5 ppm of precatalyst 5c (5 portions). The whole was stirred in argon atmosphere for an additional hour. A drop of reaction mixture was collected and diluted with ethyl acetate to 1 ml, and then a drop of 0.1 M SnatchCat solution was added to deactivate the catalyst. The sample was analysed by gas chromatography. In the chromatogram obtained the OD-9-ENE/MO/DIESTER-C18 area ratio was 21%/57%/22%, respectively.

Example XXXXVI

Application of precatalyst 5c in ring-closing metathesis reaction of compound S9 leading to macrocyclic lactone P9.

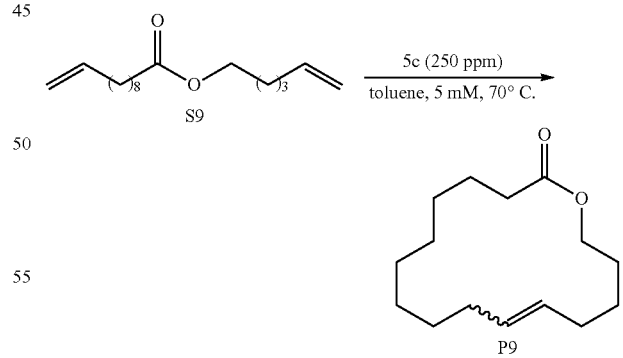

Figure 4:
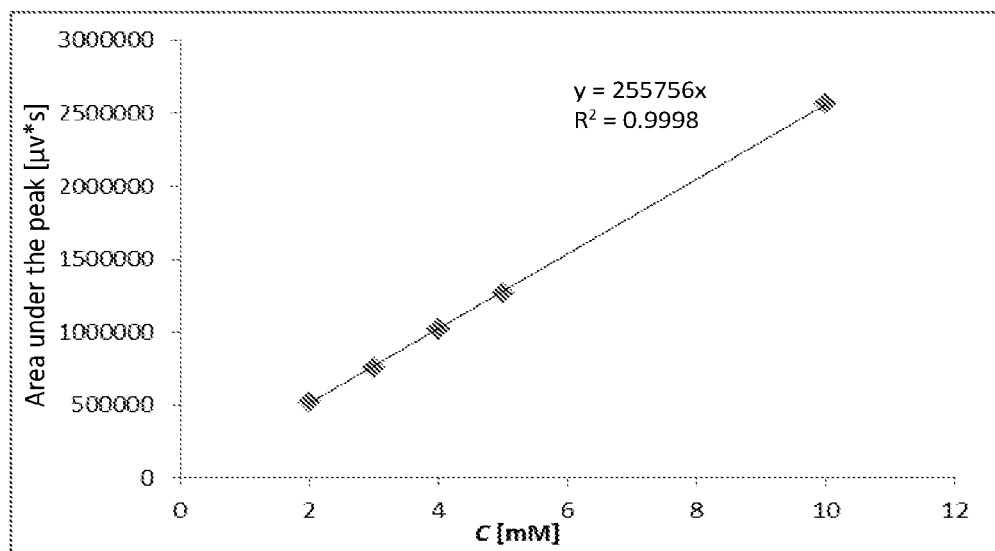
FIG. 4 shows standard curve for product P9 of the Example XXXXVI.

To solution of compound 59 (213.0 mg, 0.799 mmol) in dry deoxygenated toluene (160 ml, Csg=SmM) at 70° C., in argon atmosphere every 15 minutes a solution of precatalyst 5c (0.040 mg, 0.040 μmol, SO ppm) in dry deoxygenated toluene (SO μl) was added up to a total amount of (pre) catalyst 250 ppm (5 portions). The whole was stirred in argon atmosphere for an additional hour. 1 ml of the reaction mixture sample was collected to which a drop of 0.1 M SnatchCat solution was added to deactivate the catalyst. Conversion of substrate determined by gas chromatography with external standard was 95%. E/Z=65:35. Standard curve for product P9 was shown in the FIG. 4.

Postreaction mixture was analysed with GC without further dilutions. Cumulative area under the peaks (E and Z isomers) of the product was 1165868 (mean of three injections). Product concentration in postreaction mixture was 4.56 mM (C=1165868/255756). Yield GC Y=4.56 mM×100%/5 mM=91%.

$^{1}$H NMR (CDCl$_{3}$, 500 MHz): δ=5.43-5.23 (m, 2H), 4.13 (t, J=6.3 Hz, 2H, Z), 4.11 (t, J=7.1 Hz, 2H, E), 2.35-2.27 (m, 2H), 2.07-1.98 (m, 4H), 1.67-1.55 (m, 4H), 1.44-1.16 (m, 12H) ppm.

$^{13}$C NMR (CDCl$_{3}$, 125 MHz): δ=173.8, 131.8 (E), 130.3 (E), 130.1 (Z), 129.5 (Z), 64.1 (Z), 63.9 (E), 34.7 (E), 33.8 (Z), 32.0 (E), 31.9 (E), 29.1 (Z), 28.4 (Z), 28.3 (E), 28.3 (E), 28.2 (E), 28.1 (Z), 28.0 (E), 27.9 (Z), 27.6 (Z), 27.21 (E), 27.18 (Z), 27.1 (Z), 26.6 (Z), 26.5 (E), 26.4 (Z), 25.4 (E), 25.20 (Z), 25.18 (E) ppm.

Example XXXXVII

Preparation method of precatalyst 1d without CuCl.

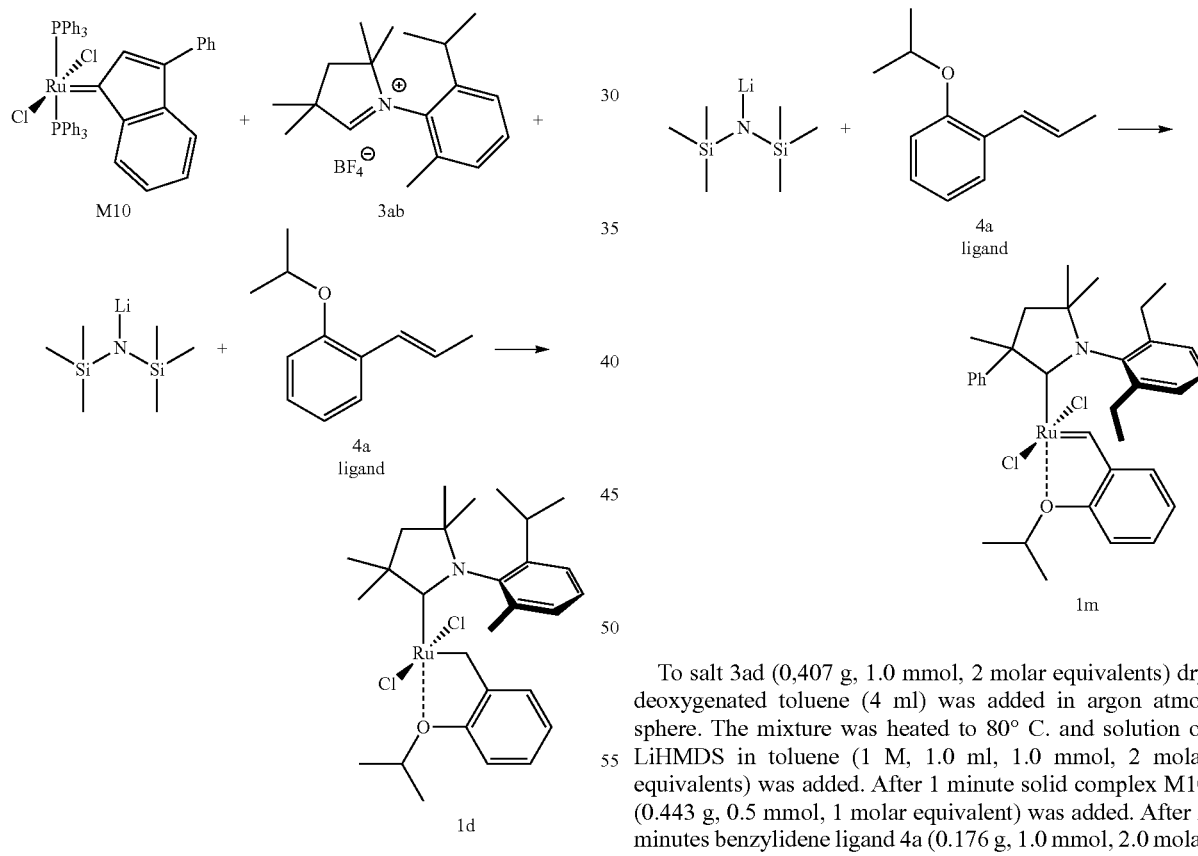

To salt 3ab (0.345 g, 1.0 mmol, 2 molar equivalents) dry deoxygenated toluene (4 ml) was added in argon atmosphere. The mixture was heated to 80° C. and solution of LiHMDS in toluene (1 M, 1.0 ml, 1.0 mmol, 2 molar equivalents) was added. After 1 minute solid complex M10 (0.443 g, 0.5 mmol, 1 molar equivalent) was added. After 2 minutes benzylidene ligand 4a (0.176 g, 1.0 mmol, 2.0 molar equivalents) was added. The whole was stirred for 30 minutes at 105° C. and cooled down to the room temperature. The crude product was isolated by column chromatography on silica gel (eluent: toluene). Green fraction was collected and concentrated to dryness. The residue was dissolved in ethyl acetate and evaporated and the residue was washed with isopropanol and dried under high vacuum giving green crystalline solid—precatalyst 1d (0.130 g, 45%).

Analytical data for product 1d obtained by this method were identical as in Example VII.

Example XXXXVIII

Preparation method of precatalyst 1m without CuCl.

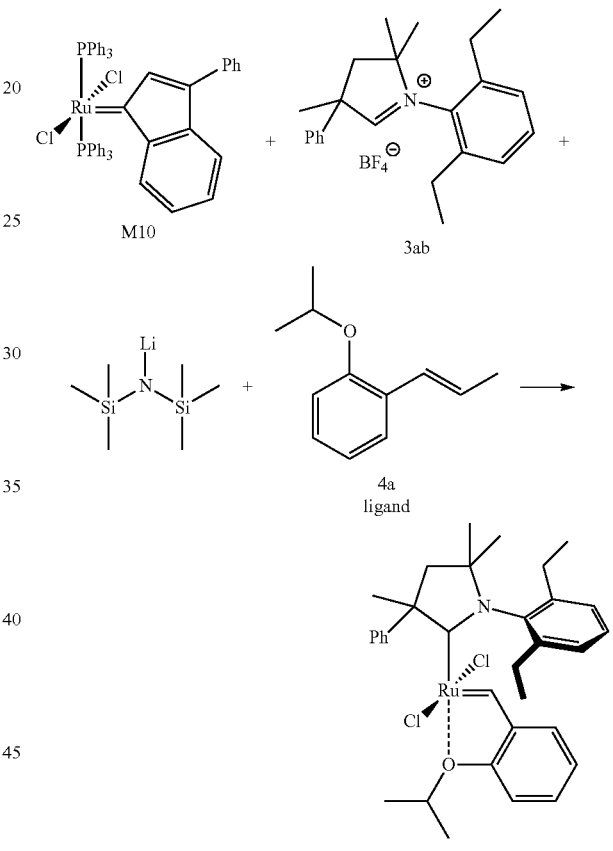

To salt 3ad (0,407 g, 1.0 mmol, 2 molar equivalents) dry deoxygenated toluene (4 ml) was added in argon atmosphere. The mixture was heated to 80° C. and solution of LiHMDS in toluene (1 M, 1.0 ml, 1.0 mmol, 2 molar equivalents) was added. After 1 minute solid complex M10 (0.443 g, 0.5 mmol, 1 molar equivalent) was added. After 2 minutes benzylidene ligand 4a (0.176 g, 1.0 mmol, 2.0 molar equivalents) was added. The whole was stirred for 30 minutes at 105° C. and cooled down to the room temperature. The crude product was isolated by column chromatography on silica gel (eluent: toluene). Green fraction was collected and concentrated to dryness. The residue was dissolved in methylene chloride and excess of isopropanol was added. Methylene chloride was evaporated under reduced pressure, the resulting precipitate was filtrated off and washed with a small amount of isopropanol. It was dried under high vacuum giving green crystalline solid—precatalyst 1m (0.151 g, 47%). A mixture of A:B isomers=1:4.

Due to a very complex $^1$H NMR spectrum only the characteristic benzylidene proton shifts were given: isomer A: singlet 17.88 ppm, isomer B: singlet 16.51 ppm (CaDa).

Example XXXXIX

Preparation method of intermediate 5a from first generation precursor M10

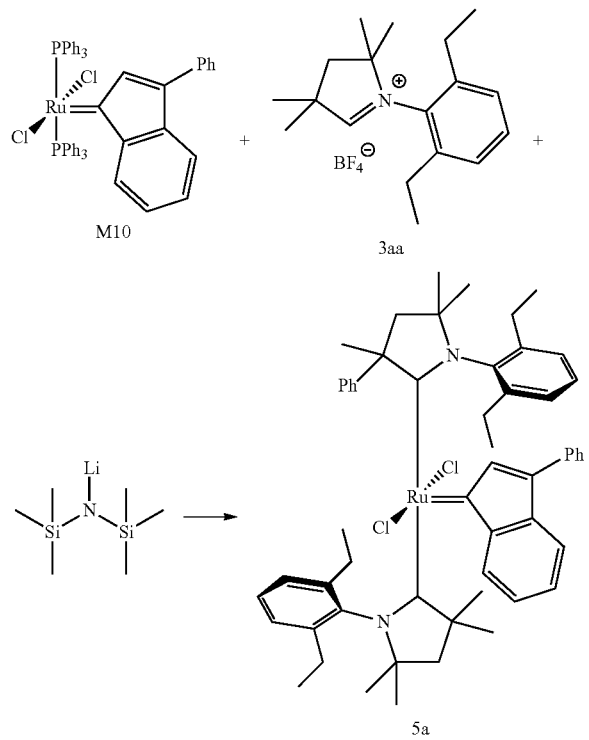

To salt 3aa (10.00 g, 29.0 mmol, 3 molar equivalents) dry deoxygenated toluene (50 ml) was added in argon atmosphere. The mixture was heated to 80° C. and solution of LiHMDS in toluene (1 M, 29.0 ml, 29.0 mmol, 3 molar equivalents) was added. After 1 minute solid complex M10 (8.56 g, 9.66 mmol, 1 molar equivalent) was added. After 5 minutes the mixture was cooled down to the room temperature. Reaction mixture was filtrated through a small amount of silica gel and washed with toluene. The crude product was isolated by column chromatography on silica gel (eluent: ethyl acetate/cyclohexane 1:9 v/v). Red fraction was collected and concentrated to dryness. It was dissolved in n-pentane and slowly concentrated to dryness (the product crystallised during solvent removal). Red crystalline solid was obtained—an intermediate compound 5a (5.02 g, 59%). Comparison with Example XV.

The project leading to this application has received funding from the European Union's Horizon 2020 research and innovation programme under grant agreement No 635405.

What is claimed is:
1. A process for producing a compound represented by the Formula 1,

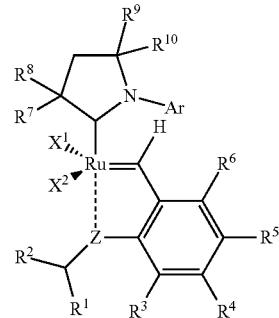

wherein:
$X^1$ and $X^2$ are each independently an anionic ligand selected from halogen, —CN, —SCN, —OR', —SR', —O(C=O)R', —O(SO$_2$)R', and —OSi(R')$_3$ group, wherein R' is $C_1$-$C_{12}$ alkyl, $C_3$-$C_{12}$ cycloalkyl, $C_2$-$C_{12}$ alkenyl, $C_5$-$C_{20}$ aryl, each of which is optionally substituted with at least one $C_1$-$C_{12}$ alkyl, $C_1$-$C_{12}$ perfluoroalkyl, $C_1$-$C_{12}$ alkoxy, $C_5$-$C_{24}$ aryloxy, $C_5$-$C_{20}$ heteroaryloxy, or halogen;

Z is selected from the group consisting of O, S, NR', wherein R' is $C_1$-$C_{12}$ alkyl, $C_3$-$C_{12}$ cycloalkyl, $C_2$-$C_{12}$ alkenyl, $C_5$-$C_{20}$ aryl, which are optionally substituted with at least one $C_1$-$C_{12}$ alkyl, $C_1$-$C_{12}$ perfluoroalkyl, $C_1$-$C_{12}$ alkoxy, $C_5$-$C_{24}$ aryloxy, $C_5$-$C_{20}$ heteroaryloxy, or halogen;

Ar is an aryl group substituted with hydrogen atoms or optionally substituted with at least one $C_1$-$C_{12}$ alkyl, $C_1$-$C_{12}$ perfluoroalkyl, $C_1$-$C_{12}$ alkoxy, $C_5$-$C_{24}$ aryloxy, and $C_5$-$C_{20}$ heteroaryloxy group, or halogen;

$R^1$ and $R^2$ are each independently hydrogen, $C_1$-$C_{25}$ alkyl group, $C_1$-$C_{25}$ alkoxy group, $C_2$-$C_{25}$ alkenyl group, $C_1$-$C_{12}$ perfluoroalkyl, $C_5$-$C_{20}$ aryl, $C_5$-$C_{24}$ aryloxy, $C_5$-$C_{20}$ heteroaryloxy; or $R^1$ and $R^2$ are combined together to form substituted or unsubstituted $C_4$-$C_{10}$ cyclic or $C_4$-$C_{12}$ polycyclic system; or an ester (—COOR'), amide (—CONR'$_2$), formyl (—CHO), ketone (—COR'), and hydroxamic (—CON(OR')(R')) group, in which R' is $C_1$-$C_{12}$ alkyl, $C_3$-$C_{12}$ cycloalkyl, $C_2$-$C_{12}$ alkenyl, $C_5$-$C_{20}$ aryl, each of which is optionally substituted with at least one $C_1$-$C_{12}$ alkyl, $C_1$-$C_{12}$ perfluoroalkyl, $C_1$-$C_{12}$ alkoxy, $C_5$-$C_{24}$ aryloxy, $C_5$-$C_{20}$ heteroaryloxy, or halogen;

$R^3$, $R^4$, $R^5$, $R^6$ are each independently hydrogen, $C_1$-$C_{25}$ alkyl group, $C_1$-$C_{25}$ alkoxy group, or $C_2$-$C_{25}$ alkenyl group; or $R^3$, $R^4$, $R^5$, $R^6$ substituents can be combined together to form a substituted or unsubstituted $C_4$-$C_{10}$ cyclic or $C_4$-$C_{12}$ polycyclic system; or an alkoxy (—OR'), sulfide (—SR'), sulfoxide (—S(O)R'), sulfonium (—S$^+$R'$_2$), sulfone (—SO$_2$R'), sulfonamide (—SO$_2$NR'$_2$), amine (—NR'$_2$), ammonium (—N$^+$R'$_3$), nitro (—NO$_2$), cyano (—CN), phosphonate (—P(O)(OR')$_2$), phosphinate (—P(O)R'(OR')), phosphoninum (—P(OR')$_2$), phosphine (—PR'$_2$), phosphine oxide (—P(O)R'$_2$), phosphonium (—P$^+$R'$_3$), carboxy (—COOH), ester (—COOR'), amide (—CONR'$_2$, or —NR'C(O)R'), formyl (—CHO), or ketone (—COR')

group, wherein R' is $C_1$-$C_5$ alkyl, $C_1$-$C_5$ perfluoroalkyl, $C_5$-$C_{24}$ aryl, $C_7$-$C_{24}$ aralkyl, or $C_5$-$C_{24}$ perfluoroaryl; and $R^7$, $R^8$, $R^9$, and $R^{10}$ are each independently hydrogen atom, or $C_1$-$C_{25}$ alkyl group; or $R^7$ and $R^8$, $R^7$ and $R^9$, $R^8$ and $R^{10}$, or $R^9$ and $R^{10}$ are combined to form a cyclic system; or independently $C_1$-$C_{12}$ alkyl group, $C_3$-$C_{12}$ cycloalkyl, $C_2$-$C_{12}$ alkenyl, $C_5$-$C_{20}$ aryl, $C_1$-$C_5$ perfluoroalkyl, $C_7$-$C_{24}$ aralkyl, $C_5$-$C_{24}$ perfluoroaryl, each of which is optionally substituted with at least one $C_1$-$C_{12}$ alkyl, $C_1$-$C_{12}$ perfluoroalkyl, $C_1$-$C_{12}$ alkoxy, $C_5$-$C_{24}$ aryloxy, $C_5$-$C_{20}$ heteroaryloxy, or halogen;

characterized in that an alkylidene ruthenium complex represented by the Formula 2

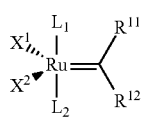

2 wherein:
- $L^1$ and $L^2$ are each a neutral phosphine ligand $P(R')_3$, wherein each R' is independently $C_1$-$C_{12}$ alkyl, $C_3$-$C_{12}$ cycloalkyl, $C_5$-$C_{20}$ aryl, $C_7$-$C_{24}$ aralkyl, $C_5$-$C_{24}$ perfluoroaryl, 5-12-membered heteroaryl; or wherein two R' can be combined together to form a cycloalkyl ring containing phosphorus atom in the ring;
- $X^1$ and $X^2$ are each independently an anionic ligand selected from halogen, —CN, —SCN, —OR', —SR', —O(C═O)R', —O(SO$_2$)R', and —OSi(R')$_3$ group, wherein R' is $C_1$-$C_{12}$ alkyl, $C_3$-$C_{12}$ cycloalkyl, $C_2$-$C_{12}$ alkenyl, $C_5$-$C_{20}$ aryl, each of which is optionally substituted with at least one $C_1$-$C_{12}$ alkyl, $C_1$-$C_{12}$ perfluoroalkyl, $C_1$-$C_{12}$ alkoxy, $C_5$-$C_{24}$ aryloxy, $C_5$-$C_{20}$ heteroaryloxy, or halogen;
- $R^{11}$ and $R^{12}$ are each independently hydrogen, halogen, optionally substituted $C_1$-$C_{25}$ alkyl, optionally substituted $C_1$-$C_{25}$ perfluoroalkyl, optionally substituted $C_2$-$C_{25}$ alkene, optionally substituted $C_3$-$C_7$ cycloalkyl, optionally substituted $C_2$-$C_{25}$ alkenyl, optionally substituted $C_3$-$C_{25}$ cycloalkenyl, optionally substituted $C_2$-$C_{25}$ alkynyl, optionally substituted $C_3$-$C_{25}$ cycloalkynyl, optionally substituted $C_1$-$C_{25}$ alkoxy, optionally substituted $C_5$-$C_{24}$ aryloxy, optionally substituted $C_5$-$C_{20}$ heteroaryloxy, optionally substituted $C_5$-$C_{24}$ aryl, optionally substituted $C_5$-$C_{20}$ heteroaryl, optionally substituted $C_7$-$C_{24}$ aralkyl, optionally substituted $C_5$-$C_{24}$ perfluoroaryl, or optionally substituted 3-12-membered heterocycle; or
- wherein $R^{11}$ and $R^{12}$ substituents are combined together to form a ring selected from the group consisting of $C_3$-$C_7$ cycloalkyl, $C_3$-$C_{25}$ cycloalkenyl, $C_3$-$C_{25}$ cycloalkynyl, $C_5$-$C_{24}$ aryl, $C_5$-$C_{20}$ heteroaryl, $C_5$-$C_{24}$ perfluoroaryl, 3-12-membered heterocycle, each of which is optionally substituted independently with one or more substituents selected from the group consisting of hydrogen, halogen, $C_1$-$C_{25}$ alkyl, $C_1$-$C_{25}$ perfluoroalkyl, $C_2$-$C_{25}$ alkene, $C_3$-$C_7$ cycloalkyl, $C_2$-$C_{25}$ alkenyl, $C_3$-$C_{25}$ cycloalkenyl, $C_2$-$C_{25}$ alkynyl, $C_3$-$C_{25}$ cycloalkynyl, $C_1$-$C_{25}$ alkoxy, $C_5$-$C_{24}$ aryloxy, $C_5$-$C_{20}$ heteroaryloxy, $C_5$-$C_{24}$ aryl, $C_5$-$C_{20}$ heteroaryl, $C_7$-$C_{24}$ aralkyl, $C_5$-$C_{24}$ perfluoroaryl, or 3-12-membered heterocycle;

is reacted with a carbene represented by the Formula 3

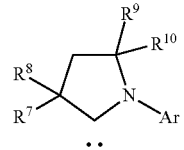

3 wherein:
- Ar is an aryl group substituted with hydrogen atoms or optionally substituted with at least one $C_1$-$C_{12}$ alkyl, $C_1$-$C_{12}$ perfluoroalkyl, $C_1$-$C_{12}$ alkoxy, $C_5$-$C_{24}$ aryloxy, and $C_5$-$C_{20}$ heteroaryloxy group, or halogen;
- $R^7$, $R^8$, $R^9$, and $R^{10}$ are each independently hydrogen atom, or $C_1$-$C_{25}$ alkyl group; or $R^7$ and $R^8$, $R^7$ and $R^9$, $R^8$ and $R^{10}$, or $R^9$ and $R^{10}$ are combined to form a cyclic system; or independently $C_1$-$C_{12}$ alkyl group, $C_3$-$C_{12}$ cycloalkyl, $C_2$-$C_{12}$ alkenyl, $C_5$-$C_{20}$ aryl, $C_1$-$C_5$ perfluoroalkyl, $C_7$-$C_{24}$ aralkyl, $C_5$-$C_{24}$ perfluoroaryl, each of which is optionally substituted with at least one $C_1$-$C_{12}$ alkyl, $C_1$-$C_{12}$ perfluoroalkyl, $C_1$-$C_{12}$ alkoxy, $C_5$-$C_{24}$ aryloxy, $C_5$-$C_{20}$ heteroaryloxy, or halogen;

thus formed reaction mixture is then contacted with a compound represented by the Formula 4

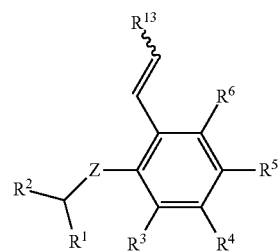

4 wherein:
- Z is selected from the group consisting of O, S, NR', wherein R' is $C_1$-$C_{12}$ alkyl, $C_3$-$C_{12}$ cycloalkyl, $C_2$-$C_{12}$ alkenyl, $C_5$-$C_{20}$ aryl, which are optionally substituted with at least one $C_1$-$C_{12}$ alkyl, $C_1$-$C_{12}$ perfluoroalkyl, $C_1$-$C_{12}$ alkoxy, $C_5$-$C_{24}$ aryloxy, $C_5$-$C_{20}$ heteroaryloxy, or halogen;
- $R^1$ and $R^2$ are each independently hydrogen, $C_1$-$C_{25}$ alkyl group, $C_1$-$C_{25}$ alkoxy group, $C_2$-$C_{25}$ alkenyl group, $C_1$-$C_{12}$ perfluoroalkyl, $C_5$-$C_{20}$ aryl, $C_5$-$C_{24}$ aryloxy, $C_5$-$C_{20}$ heteroaryloxy; or $R^1$ and $R^2$ are combined together to form substituted or unsubstituted $C_4$-$C_{10}$ cyclic or $C_4$-$C_{12}$ polycyclic system; or an ester (—COOR'), amide (—CONR'$_2$), formyl (—CHO), ketone (—COR'), and hydroxamic (—CON(OR')(R')) group, in which R' is $C_1$-$C_{12}$ alkyl, $C_3$-$C_{12}$ cycloalkyl, $C_2$-$C_{12}$ alkenyl, $C_5$-$C_{20}$ aryl, each of which is optionally substituted with at least one $C_1$-$C_{12}$ alkyl, $C_1$-$C_{12}$ perfluoroalkyl, $C_1$-$C_{12}$ alkoxy, $C_5$-$C_{24}$ aryloxy, $C_5$-$C_{20}$ heteroaryloxy, or halogen;
- $R^3$, $R^4$, $R^5$, $R^6$ are each independently hydrogen, $C_1$-$C_{25}$ alkyl group, $C_1$-$C_{25}$ alkoxy group, or $C_2$-$C_{25}$ alkenyl group; or $R^3$, $R^4$, $R^5$, $R^6$ substituents can be combined together to form a substituted or unsubstituted $C_4$-$C_{10}$ cyclic or $C_4$-$C_{12}$ polycyclic system; or an alkoxy (—OR'), sulfide (—SR'), sulfoxide (—S(O)R'), sulfonium (—S⁺R'₂), sulfone (—SO₂R'), sulfonamide (—SO₂NR'₂), amine (—NR'₂), ammonium (—N⁺R'₃), nitro (—NO₂), cyano (—CN), phosphonate (—P(O)(OR')₂), phosphinate (—P(O)R'(OR')), phosphoninum (—P(OR')₂), phosphine (—PR'₂), phosphine oxide (—P(O)R'₂), phosphonium (—P⁺R'₃), carboxy (—COOH), ester (—COOR'), amide (—CONR'₂, or —NR'C(O)R'), formyl (—CHO), or ketone (—COR') group, wherein R' is $C_1$-$C_5$ alkyl, $C_1$-$C_5$ perfluoroalkyl, $C_5$-$C_{24}$ aryl, $C_7$-$C_{24}$ aralkyl, or $C_5$-$C_{24}$ perfluoroaryl; and $R^{13}$ is hydrogen, halogen, $C_1$-$C_{25}$ alkyl group, $C_1$-$C_{25}$ alkoxy group, $C_2$-$C_{25}$ alkenyl group, $C_1$-$C_{12}$ perfluoroalkyl, $C_5$-$C_{20}$ aryl, $C_5$-$C_{24}$ aryloxy, $C_5$-$C_{20}$ heteroaryloxy; or are combined together to form a substituted or unsubstituted $C_4$-$C_{10}$ cyclic or $C_4$-$C_{12}$ polycyclic system;

to form the compound represented by the Formula 1.

2. The process according to claim 1, characterized in that the reaction mixture is contacted with the compound represented by the Formula 4 in the presence of phosphine ligand scavenger $PR'_3$ or cyclic alkyl amino carbene ligand scavenger.

3. The process according to claim 2, characterized in that a compound selected from copper(I) salts or HCl is used as phosphine ligand scavenger $PR'_3$ or cyclic alkyl amino carbene ligand scavenger.

4. The process according to claim 1, characterized in that carbenes represented by the Formula 3 are provided to the reaction medium by their generation in situ from suitable carbene precursors, cyclic alkyl amino carbene salts represented by the Formula 3a,

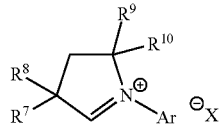

3a wherein:
Ar is an aryl group substituted with hydrogen atoms or optionally substituted with at least one $C_1$-$C_{12}$ alkyl, $C_1$-$C_{12}$ perfluoroalkyl, $C_1$-$C_{12}$ alkoxy, $C_5$-$C_{24}$ aryloxy, and $C_5$-$C_{20}$ heteroaryloxy group, or halogen;

$R^7$, $R^8$, $R^9$, and $R^{10}$ are each independently hydrogen atom, or $C_1$-$C_{25}$ alkyl group; or $R^7$ and $R^8$, $R^7$ and $R^9$, $R^8$ and $R^{10}$, or $R^9$ and $R^{10}$ are combined to form a cyclic system; or independently $C_1$-$C_{12}$ alkyl group, $C_3$-$C_{12}$ cycloalkyl, $C_2$-$C_{12}$ alkenyl, $C_5$-$C_{20}$ aryl, $C_1$-$C_5$ perfluoroalkyl, $C_7$-$C_{24}$ aralkyl, $C_5$-$C_{24}$ perfluoroaryl, each of which is optionally substituted with at least one $C_1$-$C_{12}$ alkyl, $C_1$-$C_{12}$ perfluoroalkyl, $C_1$-$C_{12}$ alkoxy, $C_5$-$C_{24}$ aryloxy, $C_5$-$C_{20}$ heteroaryloxy, or halogen;

$X^-$ is a halide anion, or $BF_4^-$, $PF_6^-$, $ClO_4^-$, $CF_3SO_2O^-$; involving contacting compound represented by the Formula 3a with suitable base selected from potassium N,N'-bis(trimethylsilyl)amide, lithium N,N'-bis(trimethylsilyl)amide, sodium N,N'-bis(trimethylsilyl)amide, potassium tert-amylate, potassium tert-butoxide, sodium hydride.

5. The process according to claim 4 wherein carbene precursors represented by the Formula 3a are contacted with a base such as alkali metal N,N'-bis(trimethylsilyl)amide.

6. The process according to claim 1, characterized in that the alkylidene ruthenium complex represented by the Formula 2 is reacted with a carbene represented by the Formula 3 to form an intermediate represented by the Formula 5

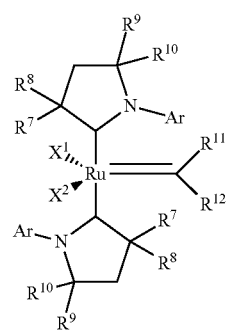

5 wherein:
$X^1$ and $X^2$ are each independently an anionic ligand selected from halogen, —CN, —SCN, —OR', —SR', —O(C=O)R', —O(SO₂)R', and —OSi(R')₃ group, wherein R' is $C_1$-$C_{12}$ alkyl, $C_3$-$C_{12}$ cycloalkyl, $C_2$-$C_{12}$ alkenyl, $C_5$-$C_{20}$ aryl, each of which is optionally substituted with at least one $C_1$-$C_{12}$ alkyl, $C_1$-$C_{12}$ perfluoroalkyl, $C_1$-$C_{12}$ alkoxy, $C_5$-$C_{24}$ aryloxy, $C_5$-$C_{20}$ heteroaryloxy, or halogen;

Ar is an aryl group substituted with hydrogen atoms or optionally substituted with at least one $C_1$-$C_{12}$ alkyl, $C_1$-$C_{12}$ perfluoroalkyl, $C_1$-$C_{12}$ alkoxy, $C_5$-$C_{24}$ aryloxy, and $C_5$-$C_{20}$ heteroaryloxy group, or halogen;

$R^7$, $R^8$, $R^9$, and $R^{10}$ are each independently hydrogen atom, or $C_1$-$C_{25}$ alkyl group; or $R^7$ and $R^8$, $R^7$ and $R^9$, $R^8$ and $R^{10}$, or $R^9$ and $R^{10}$ are combined to form a cyclic system; or independently $C_1$-$C_{12}$ alkyl group, $C_3$-$C_{12}$ cycloalkyl, $C_2$-$C_{12}$ alkenyl, $C_5$-$C_{20}$ aryl, $C_1$-$C_5$ perfluoroalkyl, $C_7$-$C_{24}$ aralkyl, $C_5$-$C_{24}$ perfluoroaryl, each of which is optionally substituted with at least one $C_1$-$C_{12}$ alkyl, $C_1$-$C_{12}$ perfluoroalkyl, $C_1$-$C_{12}$ alkoxy, $C_5$-$C_{24}$ aryloxy, $C_5$-$C_{20}$ heteroaryloxy, or halogen; and $R^{11}$ and $R^{12}$ are each independently hydrogen, halogen, optionally substituted $C_1$-$C_{25}$ alkyl, optionally substituted $C_1$-$C_{25}$ perfluoroalkyl, optionally substituted $C_2$-$C_{25}$ alkene, optionally substituted $C_3$-$C_7$ cycloalkyl, optionally substituted $C_2$-$C_{25}$ alkenyl, optionally substituted $C_3$-$C_{25}$ cycloalkenyl, optionally substituted $C_2$-$C_{25}$ alkynyl, optionally substituted $C_3$-$C_{25}$ cycloalkynyl, optionally substituted $C_1$-$C_{25}$ alkoxy, optionally substituted $C_5$-$C_{24}$ aryloxy, optionally substituted $C_5$-$C_{20}$ heteroaryloxy, optionally substituted $C_5$-$C_{24}$ aryl, optionally substituted $C_5$-$C_{20}$ heteroaryl, optionally substituted $C_7$-$C_{24}$ aralkyl, optionally substituted $C_5$-$C_{24}$ perfluoroaryl, or optionally substituted 3-12-membered heterocycle; or wherein $R^{11}$ and $R^{12}$ substituents are combined together to form a ring selected from the group consisting of $C_3$-$C_7$ cycloalkyl, $C_3$-$C_{25}$ cycloalkenyl, $C_3$-$C_{25}$ cycloalkynyl, $C_5$-$C_{24}$ aryl, $C_5$-$C_{20}$ heteroaryl, $C_5$-$C_{24}$ perfluoroaryl, 3-12-membered heterocycle, each of which is optionally substituted independently with one or more substituents selected from the group consisting of hydrogen, halogen, $C_1$-$C_{25}$ alkyl, $C_1$-$C_{25}$ perfluoroalkyl, $C_2$-$C_{25}$ alkene, $C_3$-$C_7$ cycloalkyl, $C_2$-$C_{25}$ alkenyl, $C_3$-$C_{25}$ cycloalkenyl, $C_2$-$C_{25}$ alkynyl, $C_3$-$C_{25}$ cycloalkynyl, $C_1$-$C_{25}$ alkoxy, $C_5$-$C_{24}$ aryloxy, $C_5$-$C_{20}$ heteroaryloxy, $C_5$-$C_{24}$ aryl, $C_5$-$C_{20}$ heteroaryl, $C_7$-$C_{24}$ aralkyl, $C_5$-$C_{24}$ perfluoroaryl, or 3-12-membered heterocycle;

which then is contacted with the compound represented by the Formula 4

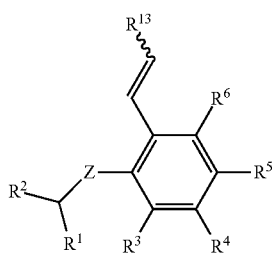

4 wherein:
Z is selected from the group consisting of O, S, NR', wherein R' is $C_1$-$C_{12}$ alkyl, $C_3$-$C_{12}$ cycloalkyl, $C_2$-$C_{12}$ alkenyl, $C_5$-$C_{20}$ aryl, which are optionally substituted with at least one $C_1$-$C_{12}$ alkyl, $C_1$-$C_{12}$ perfluoroalkyl, $C_1$-$C_{12}$ alkoxy, $C_5$-$C_{24}$ aryloxy, $C_5$-$C_{20}$ heteroaryloxy, or halogen;

$R^1$ and $R^2$ are each independently hydrogen, $C_1$-$C_{25}$ alkyl group, $C_1$-$C_{25}$ alkoxy group, $C_2$-$C_{25}$ alkenyl group, $C_1$-$C_{12}$ perfluoroalkyl, $C_5$-$C_{20}$ aryl, $C_5$-$C_{24}$ aryloxy, $C_5$-$C_{20}$ heteroaryloxy; or $R^1$ and $R^2$ are combined together to form substituted or unsubstituted $C_4$-$C_{10}$ cyclic or $C_4$-$C_{12}$ polycyclic system; or an ester (—COOR'), amide (—CONR'$_2$), formyl (—CHO), ketone (—COR'), and hydroxamic (—CON(OR')(R')) group, in which R' is $C_1$-$C_{12}$ alkyl, $C_3$-$C_{12}$ cycloalkyl, $C_2$-$C_{12}$ alkenyl, $C_5$-$C_{20}$ aryl, each of which is optionally substituted with at least one $C_1$-$C_{12}$ alkyl, $C_1$-$C_{12}$ perfluoroalkyl, $C_1$-$C_{12}$ alkoxy, $C_5$-$C_{24}$ aryloxy, $C_5$-$C_{20}$ heteroaryloxy, or halogen;

$R^3$, $R^4$, $R^5$, $R^6$ are each independently hydrogen, $C_1$-$C_{25}$ alkyl group, $C_1$-$C_{25}$ alkoxy group, or $C_2$-$C_{25}$ alkenyl group; or $R^3$, $R^4$, $R^5$, $R^6$ substituents can be combined together to form a substituted or unsubstituted $C_4$-$C_{10}$ cyclic or $C_4$-$C_{12}$ polycyclic system; or an alkoxy (—OR'), sulfide (—SR'), sulfoxide (—S(O)R'), sulfonium (—S$^+$R'$_2$), sulfone (—SO$_2$R'), sulfonamide (—SO$_2$NR'$_2$), amine (—NR'$_2$), ammonium (—N$^+$R'$_3$), nitro (—NO$_2$), cyano (—CN), phosphonate (—P(O)(OR')$_2$), phosphinate (—P(O)R'(OR')), phosphoninum (—P(OR')$_2$), phosphine (—PR'$_2$), phosphine oxide (—P(O)R'$_2$), phosphonium (—P$^+$R'$_3$), carboxy (—COOH), ester (—COOR'), amide (—CONR'$_2$, or —NR'C(O)R'), formyl (—CHO), or ketone (—COR') group, wherein R' is $C_1$-$C_5$ alkyl, $C_1$-$C_5$ perfluoroalkyl, $C_5$-$C_{24}$ aryl, $C_7$-$C_{24}$ aralkyl, or $C_5$-$C_{24}$ perfluoroaryl; and $R^{13}$ is hydrogen, halogen, $C_1$-$C_{25}$ alkyl group, $C_1$-$C_{25}$ alkoxy group, $C_2$-$C_{25}$ alkenyl group, $C_1$-$C_{12}$ perfluoroalkyl, $C_5$-$C_{20}$ aryl, $C_5$-$C_{24}$ aryloxy, $C_5$-$C_{20}$ heteroaryloxy; or are combined together to form a substituted or unsubstituted $C_4$-$C_{10}$ cyclic or $C_4$-$C_{12}$ polycyclic system;

to form the compound represented by the Formula 1.

7. The process according to claim 6, characterized in that the reaction of compound 5 with compound 4 is conducted in the presence of a phosphine ligand scavenger PR'$_3$ or cyclic alkyl amino carbene ligand scavenger.

8. The process according to claim 1, characterized in that all reaction steps are conducted in a polar or nonpolar solvent over a period of 1 minute to 24 hours.

9. The process of claim 1 for producing a compound represented by the Formula 1,

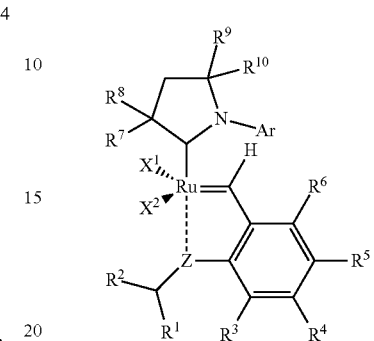

1 wherein:
$X^1$ and $X^2$ are each halogen;
Z is O;
Ar is an aryl group substituted with hydrogen atoms or optionally substituted with at least one $C_1$-$C_{12}$ alkyl;
$R^1$ and $R^2$ are each independently hydrogen or a $C_1$-$C_{25}$ alkyl group; or $R^1$ and $R^2$ are combined together to form substituted or unsubstituted $C_4$-$C_{10}$ cyclic or $C_4$-$C_{12}$ polycyclic system; or an ester (—COOR'), amide (—CONR'$_2$), or hydroxamic (—CON(OR')(R')) group, wherein each R' is independently $C_1$-$C_{12}$ alkyl;
$R^3$, $R^4$, $R^5$, $R^6$ are each independently hydrogen or a $C_1$-$C_{25}$ alkyl group; or $R^3$, $R^4$, $R^5$, $R^6$ substituents can be combined together to form a substituted or unsubstituted $C_4$-$C_{10}$ cyclic or $C_4$-$C_{12}$ polycyclic system; or nitro (—NO$_2$) group; and
$R^7$, $R^8$, $R^9$, and $R^{10}$ are each independently hydrogen atom, or $C_1$-$C_{25}$ alkyl group; or $R^7$ and $R^8$, $R^7$ and $R^9$, $R^8$ and $R^{10}$, or $R^9$ and $R^{10}$ are combined to form a cyclic system;

characterized in that the alkylidene ruthenium complex represented by the Formula 2

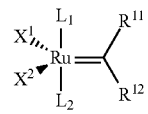

2 wherein:
$L^1$ and $L^2$ are each a neutral phosphine ligand P(R'')$_3$, wherein each R'' is independently $C_1$-$C_{12}$ alkyl, $C_5$-$C_{20}$ aryl, or $C_7$-$C_{24}$ aralkyl;
$X^1$ and $X^2$ are each halogen;
$R^{11}$ and $R^{12}$ are each independently hydrogen, optionally substituted $C_1$-$C_{25}$ alkyl, optionally substituted $C_5$-$C_{24}$ aryl, optionally substituted $C_5$-$C_{20}$ heteroaryl, optionally substituted $C_7$-$C_{24}$ aralkyl, optionally substituted $C_5$-$C_{24}$ perfluoroaryl, or optionally substituted 3-12-membered heterocycle; or
wherein $R^{11}$ and $R^{12}$ substituents are combined together to form a ring selected from the group consisting of $C_3$-$C_7$ cycloalkyl, $C_3$-$C_{25}$ cycloalkenyl, $C_3$-$C_{25}$ cycloalkynyl, $C_5$-$C_{24}$ aryl, $C_5$-$C_{20}$ heteroaryl, each of which is optionally substituted independently with one or more substituents selected from the group consisting of hydrogen, halogen, $C_1$-$C_{25}$ alkyl, $C_5$-$C_{24}$ aryl, or $C_7$-$C_{24}$ aralkyl;

is reacted with a carbene represented by the Formula 3

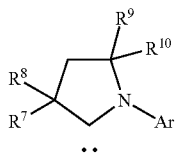

3 wherein:
Ar is an aryl group substituted with hydrogen atoms or optionally substituted with at least one $C_1$-$C_{12}$ alkyl; and
$R^7$, $R^8$, $R^9$, and $R^{10}$ are each independently hydrogen atom, or $C_1$-$C_{25}$ alkyl group; or $R^7$ and $R^8$, $R^7$ and $R^9$, $R^8$ and $R^{10}$, or $R^9$ and $R^{10}$ are combined to form a cyclic system;

thus formed reaction mixture is then contacted with the compound represented by the Formula 4

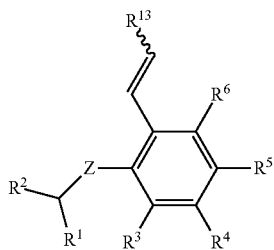

4 wherein:
Z is O;
$R^1$ and $R^2$ are each independently hydrogen or a $C_1$-$C_{25}$ alkyl group; or $R^1$ and $R^2$ are combined together to form substituted or unsubstituted $C_4$-$C_{10}$ cyclic or $C_4$-$C_{12}$ polycyclic system; or an ester (—COOR'), amide (—CONR'$_2$), or hydroxamic (—CON(OR')(R')) group, wherein each R' is independently $C_1$-$C_{12}$ alkyl;
$R^3$, $R^4$, $R^5$, $R^6$ are each independently hydrogen or a $C_1$-$C_{25}$ alkyl group; or $R^3$, $R^4$, $R^5$, $R^6$ substituents can be combined together to form a substituted or unsubstituted $C_4$-$C_{10}$ cyclic or $C_4$-$C_{12}$ polycyclic system; or nitro (—NO$_2$) group; and
$R^{13}$ is hydrogen or an $C_1$-$C_{25}$ alkyl group;

to form the compound represented by the Formula 1.

10. The process according to claim 9, characterized in that a carbene represented by the Formula 3 is provided to the reaction medium by generation in situ from suitable carbene precursors represented by the Formula 3a,

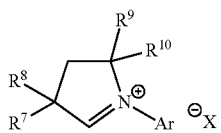

3a wherein:
Ar is an aryl group substituted with hydrogen atoms or optionally substituted with at least one $C_1$-$C_{12}$ alkyl;
$R^7$, $R^8$, $R^9$, and $R^{10}$ are each independently hydrogen atom, or $C_1$-$C_{25}$ alkyl group; or $R^7$ and $R^8$, $R^7$ and $R^9$, $R^8$ and $R^{10}$, or $R^9$ and $R^{10}$ are combined to form a cyclic system; and
$X^-$ is a halide anion or $BF_4$, involving contacting compound represented by the Formula 3a with suitable base selected from potassium N,N'-bis(trimethylsilyl)amide, lithium N,N'-bis(trimethylsilyl)amide, sodium N,N'-bis(trimethylsilyl)amide, potassium tert-amylate, potassium tert-butoxide, or sodium hydride.

11. The process according to claim 1, characterized in that the alkylidene ruthenium complex represented by the Formula 2 is reacted with a carbene represented by the Formula 3 to form an intermediate represented by the Formula 5

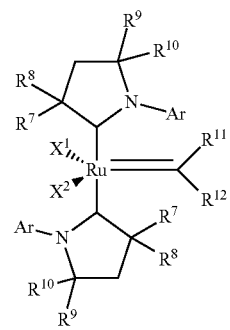

5 wherein:
$X^1$ and $X^2$ are each halogen;
Ar is an aryl group substituted with hydrogen atoms or optionally substituted with at least one $C_1$-$C_{12}$ alkyl; and
$R^7$, $R^8$, $R^9$, and $R^{10}$ are each independently hydrogen atom, or $C_1$-$C_{25}$ alkyl group; or $R^7$ and $R^8$, $R^7$ and $R^9$, $R^8$ and $R^{10}$, or $R^9$ and $R^{10}$ are combined to form a cyclic system;

which then is contacted with the compound represented by the Formula 4

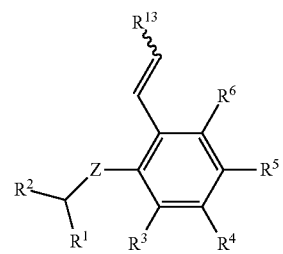

4 wherein:
Z is O;
$R^1$ and $R^2$ are each independently hydrogen or a $C_1$-$C_{25}$ alkyl group; or $R^1$ and $R^2$ are combined together to form substituted or unsubstituted $C_4$-$C_{10}$ cyclic or $C_4$-$C_{12}$ polycyclic system; or an ester (—COOR'), amide (—CONR'$_2$), or hydroxamic (—CON(OR')(R')) group, wherein each R' is independently $C_1$-$C_{12}$ alkyl;
$R^3$, $R^4$, $R^5$, $R^6$ are each independently hydrogen or a $C_1$-$C_{25}$ alkyl group; or $R^3$, $R^4$, $R^5$, $R^6$ substituents can be combined together to form a substituted or unsubstituted $C_4$-$C_{10}$ cyclic or $C_4$-$C_{12}$ polycyclic system; or nitro (—$NO_2$) group; and $R^{13}$ is hydrogen or an $C_1$-$C_{25}$ alkyl group;

to form the compound represented by the Formula 1.

* * * * *